US011708559B2

(12) United States Patent
Chou et al.

(10) Patent No.: US 11,708,559 B2
(45) Date of Patent: Jul. 25, 2023

(54) ENGINEERED RED BLOOD CELLS HAVING RARE ANTIGEN PHENOTYPES

(71) Applicants: THE CHILDREN'S HOSPITAL OF PHILADELPHIA, Philadelphia, PA (US); NEW YORK BLOOD CENTER, INC., New York, NY (US)

(72) Inventors: Stella Chou, Bryn Mawr, PA (US); Connie Westhoff, New York, NY (US)

(73) Assignees: The Children's Hospital of Philadelphia, Philadelphia, PA (US); New York Blood Center, Inc., New York, NY (US)

( * ) Notice: Subject to any disclaimer, the term of this patent is extended or adjusted under 35 U.S.C. 154(b) by 228 days.

(21) Appl. No.: 16/757,815

(22) PCT Filed: Oct. 29, 2018

(86) PCT No.: PCT/US2018/057932
§ 371 (c)(1),
(2) Date: Apr. 21, 2020

(87) PCT Pub. No.: WO2019/084531
PCT Pub. Date: May 2, 2019

(65) Prior Publication Data
US 2021/0355440 A1 Nov. 18, 2021

Related U.S. Application Data

(60) Provisional application No. 62/578,768, filed on Oct. 30, 2017, provisional application No. 62/578,263, filed on Oct. 27, 2017.

(51) Int. Cl.
*A61K 39/00* (2006.01)
*A61K 39/12* (2006.01)
*A61K 39/145* (2006.01)
*C12N 7/00* (2006.01)
*A61K 35/17* (2015.01)
*C12N 5/078* (2010.01)
*A61K 35/14* (2015.01)
*C12N 9/22* (2006.01)
*C12N 15/11* (2006.01)
*G01N 33/68* (2006.01)
*G01N 33/80* (2006.01)

(52) U.S. Cl.
CPC ............ *C12N 5/0634* (2013.01); *A61K 35/14* (2013.01); *C12N 9/22* (2013.01); *C12N 15/111* (2013.01); *G01N 33/6854* (2013.01); *C12N 2310/20* (2017.05); *C12N 2510/00* (2013.01); *G01N 33/80* (2013.01)

(58) Field of Classification Search
CPC ....... A61K 39/12; A61K 39/145; A61P 31/16; C12N 2760/16134; C12N 7/00
See application file for complete search history.

(56) References Cited

U.S. PATENT DOCUMENTS

| 5,811,301 A | 9/1998 | Cameron |
| 9,169,462 B2 | 10/2015 | Refaeli et al. |
| 9,200,253 B1 | 12/2015 | Heidaran et al. |
| 9,255,248 B2 | 2/2016 | Abbot et al. |
| 2010/0047217 A1 | 2/2010 | Refael et al. |
| 2014/0024118 A1* | 1/2014 | Nakamura ............. C12N 15/86 435/372 |
| 2016/0060601 A1 | 3/2016 | Nishino et al. |
| 2016/0139124 A1 | 5/2016 | Newman |
| 2016/0257932 A1 | 9/2016 | Kahvejian et al. |

FOREIGN PATENT DOCUMENTS

| CA | 2516123 | 8/2004 |
| WO | WO 2005/118780 | 12/2005 |
| WO | WO 2015/032340 | 3/2015 |
| WO | WO 2016/085934 | 6/2016 |

OTHER PUBLICATIONS

Kim et al., "Rh D blood group conversion using transcription activator-like effector nucleases", Nature Communications, 2015:1-12.*
Faria et al., Molecular analysis of the GYPB gene to infer S, s, and U phenotypes in an admixed population of Minas Gerais, Brazil, Rev Bras Hematol Hemoter, 2012, 34(3):212-216.*
Chen et al., "The RHCE Allele ceSL: The Second Example for D Antigen Expression Without D-specific Amino Acids," *Transfusion*, 46(5):766-772, 2006.
Chou and Friedman, "Transfusion Practices for Patients with Sickle Cell Disease at the Children's Hospital of Philadelphia," *Immunohematology*, 28(1):27-30, 2012.
Chou et al., "High Prevalence of Red Blood Cell Alloimmunization in Sickle Cell Disease Despite Transfusion from Rh-matched Minority Donors," *Blood*, 122:1062-1071, 2013.
Chou et al., "RH Genotype Matching for Transfusion Support in Sickle Cell Disease," *Blood*, 132(11):1198-1207, 2018.
Daniels et al., "The VS and V Blood Group Polymorphisms in Africans: A Serologic and Molecular Analysis," *Transfusion*, 38(10):951-958, 1998.
Denomme et al., "The Rh System," in Fung et al., (eds): AABB Technical Manual, 18th Ed., Bethesda: AABB Press, pp. 317-336, 2014.
Faria et al., "Molecular Analysis of the GYPB Gene to Infer S, S, and U Phenotypes in an Admixed Population of Minas Gerais, Brazil," *Rev. Bras. Hematol. Hemoter.*, 34(3):212-216, 2012.

(Continued)

*Primary Examiner* — Barry A Chestnut
(74) *Attorney, Agent, or Firm* — Parker Highlander PLLC

(57) ABSTRACT

Provided herein are engineered red blood cells expressing rare blood antigen group profiles, and methods of making use the same, are described. Also provided are recombinant reagent red blood cells that express or lack the expression of at least one protein (e.g., a blood group antigen) on its surface and uses thereof.

20 Claims, 26 Drawing Sheets
Specification includes a Sequence Listing.

(56) References Cited

OTHER PUBLICATIONS

Flegel et al., "The RHCE Allele ceCF: The Molecular Basis of Crawford (RH43)," *Transfusion*, 46(8):1334-1342, 2006.

Hawksworth et al., "Enhancement of Red Blood Cell Transfusion Compatibility Using CRISPR-mediated Erythroblast Gene Editing," *EMBO Mol. Med.*, 10(6): e8454, 2018.

Hipsky et al., "Molecular Basis of the Rare Gene Complex, DIVa(C)-, Which Encodes Four Low-Prevalence Antigens in the Rh Blood Group System," *Vox Sang*, 102(2):167-170, 2012.

Kim et al., "Rh D Blood Group Conversion Using Transcription Activator-Like Effector Nucleases," *Nat. Commun.*, 6(7451):1-12, 2015.

Noizat-Pirenne and Tournamille, "Relevance of RH Variants in Transfusion of Sickle Cell Patients," *Transfus. Clin. Biol.*, 18(5-6):527-535, 2011.

PCT International Search Report and Written Opinion issued in International Application No. PCT/US2018/057932, dated Apr. 1, 2019.

PCT Invitation to Pay Additional Fees issued in International Application No. PCT/US2018/057932, dated Feb. 8, 2019.

Tiyaboonchai et al., "Utilization of the AAVS1 safe harbor locus for hematopoietic specific transgene expression and gene knockdown in human ES cells," *Stem Cell Research*, 12:630-637, 2014.

Vege et al., "E Antigen Typing Discrepancy Reveals a Novel 674C>G Change (Ser225Cys) on RhCe Responsible for Expression of Some E Epitopes Transfusion," *Transfusion*, 52, 34A supplement. Abstract, 2012.

Wagner et al., "The DAU Allele Cluster of the RHD Gene," *Blood*, 100(1):306-311, 2002.

Westhoff et al., "DIIIa and DIII Type 5 Are Encoded by the Same Allele and Are Associated With Altered RHCE*ce Alleles: Clinical Implications," *Transfusion*, 50(6):1303-1311, 2010.

Westhoff et al., "RHCE*ceTI encodes partial c and partial e and is often in cis to RHD*DIVa," Transfusion, 53(4):741-6, 2012.

Yawn et al., "Management of Sickle Cell Disease: Summary of the 2014 Evidence-Based Report by Expert Panel Members," JAMA, 312(10): 1033-1048, 2014.

Yazdanbakhsh et al., "High-level, stable expression of blood group antigens in a heterologous system," *Am. J. Hematology*, 63(3):114-124, 2000.

* cited by examiner

| | Rh | | | | | | Kell | | Duffy | | Kidd | | Lewis | | MNS | | | | | SERUM |
|---|---|---|---|---|---|---|---|---|---|---|---|---|---|---|---|---|---|---|---|---|
| | D | C | E | c | e | hr^B | K | k | Fy^a | Fy^b | Jk^a | Jk^b | Le^a | Le^b | M | N | S | s | U | Gel |
| I | + | + | 0 | 0 | + | + | 0 | + | 0 | + | 0 | + | 0 | + | + | 0 | + | 0 | + | 3+ |
| II | + | 0 | + | + | 0 | + | 0 | + | + | 0 | + | 0 | + | 0 | 0 | + | + | + | + | 3+ |
| III | 0 | 0 | 0 | + | + | + | + | + | 0 | + | 0 | + | 0 | + | + | + | 0 | + | + | 3+ |
| Auto-control | | | | | | | | | | | | | | | | | | | | 2+ |
| Rh-null | 0 | 0 | 0 | 0 | 0 | + | 0 | + | + | 0 | 0 | + | 0 | + | 0 | + | 0 | + | + | 0 |
| D-- | + | 0 | 0 | 0 | 0 | + | 0 | + | + | 0 | 0 | + | 0 | + | 0 | + | 0 | + | + | 0 |
| U- | + | 0 | 0 | + | + | 0 | 0 | + | + | 0 | 0 | + | 0 | + | 0 | + | 0 | + | 0 | 0 |

FIG. 1

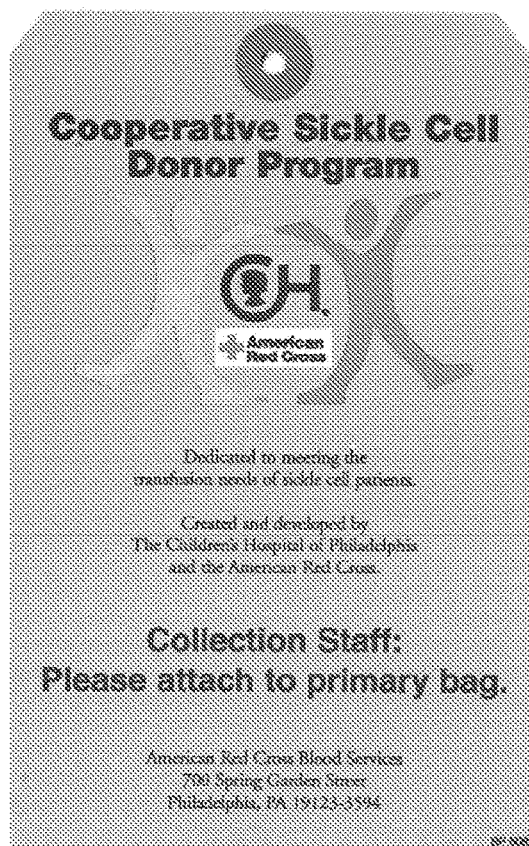
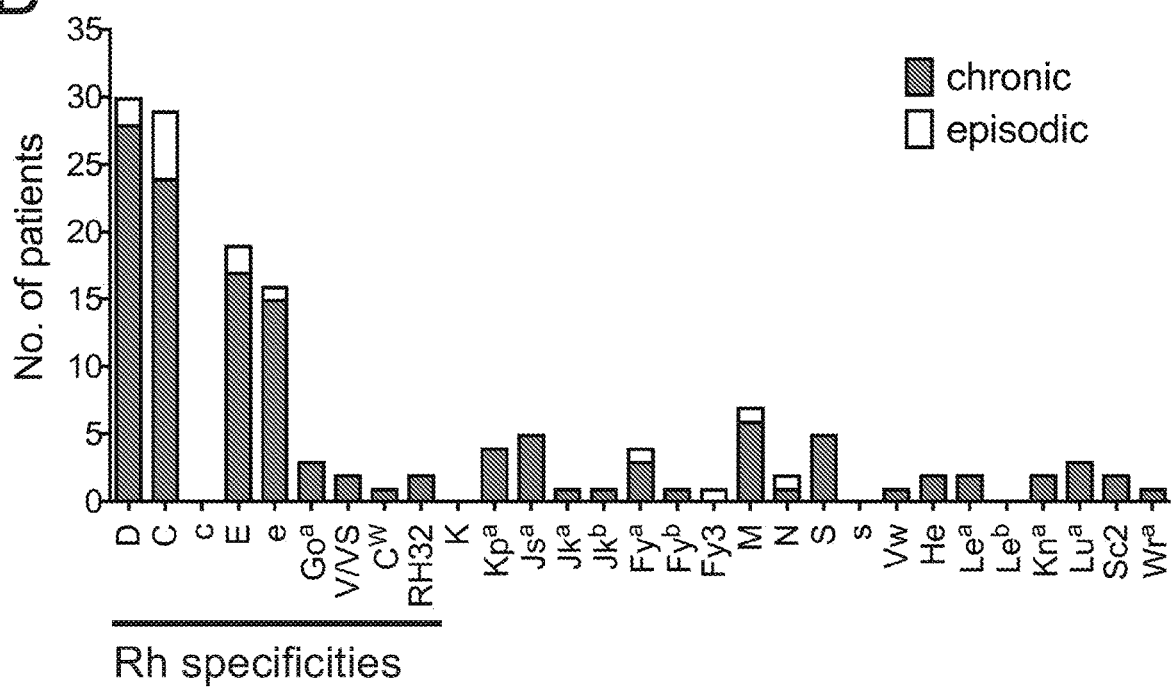
FIGS. 3A-B

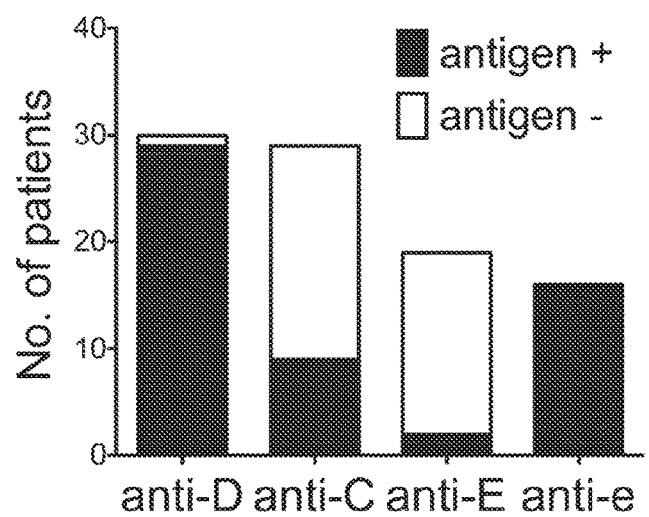
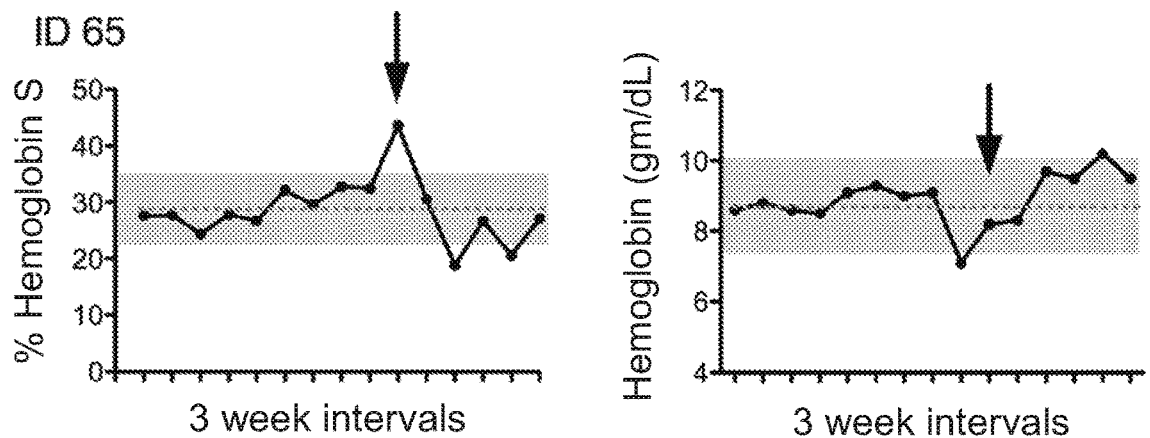
FIGS. 3C-D

| RHD | Patients | AA donors |
|---|---|---|
| Deleted D | 0.129 | 0.117 |
| RHDψ | 0.029 | 0.038 |
| DIIIa-CE(4-7)-D | 0.031 | 0.026 |
| RHD conventional | 0.545 | 0.598 |
| DAU0 | 0.165 | 0.141 |
| DAU3 | 0.016 | 0.021 |
| DAU4 | 0.001 | 0.003 |
| DAU5 | 0.013 | 0.008 |
| DIIIa | 0.014 | 0.009 |
| DIVa | 0.018 | 0.014 |
| DAR | 0.004 | 0.006 |
| Weak partial D 4.0 | 0.030 | 0.009 |
| Other variant | 0.006 | 0.008 |

| RHCE*ce | Patients | AA donors |
|---|---|---|
| ce conventional | 0.246 | 0.221 |
| ce(48C) | 0.193 | 0.192 |
| ce(733G) | 0.132 | 0.139 |
| ce(48C,733G) | 0.072 | 0.058 |
| ce(254G) | 0.046 | 0.058 |
| ceS | 0.042 | 0.058 |
| ceTI | 0.023 | 0.031 |
| ceMO | 0.009 | 0.015 |
| ceCF | 0.004 | 0.007 |
| ceAR | 0.002 | 0.002 |
| ceEK | 0.004 | 0.002 |
| Other variant | 0.006 | 0.049 |

| RHCE*Ce | Patients | AA donors |
|---|---|---|
| Ce conventional | 0.119 | 0.136 |
| CeRN | 0.003 | 0.002 |

| RHCE*cE | Patients | AA donors |
|---|---|---|
| cE conventional | 0.093 | 0.093 |
| Other variant | 0.005 | 0.001 |

FIG. 4

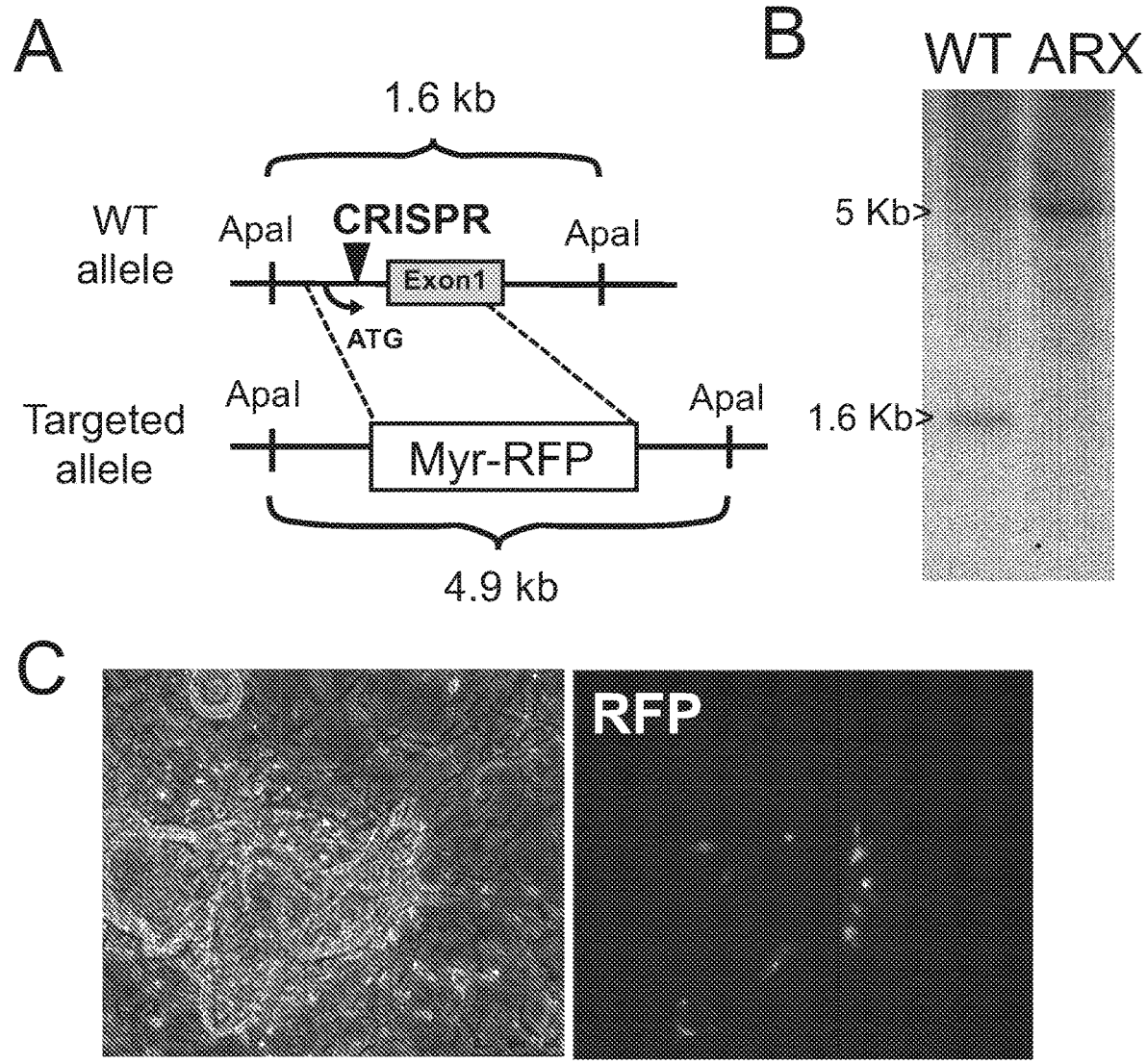
FIGS. 5A-C

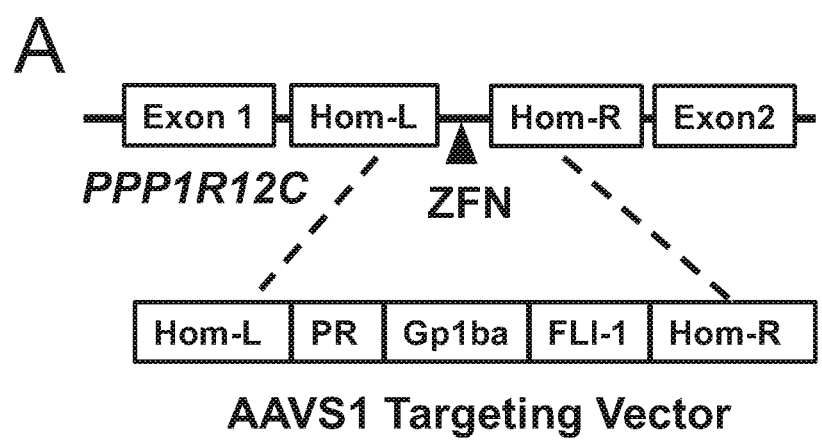
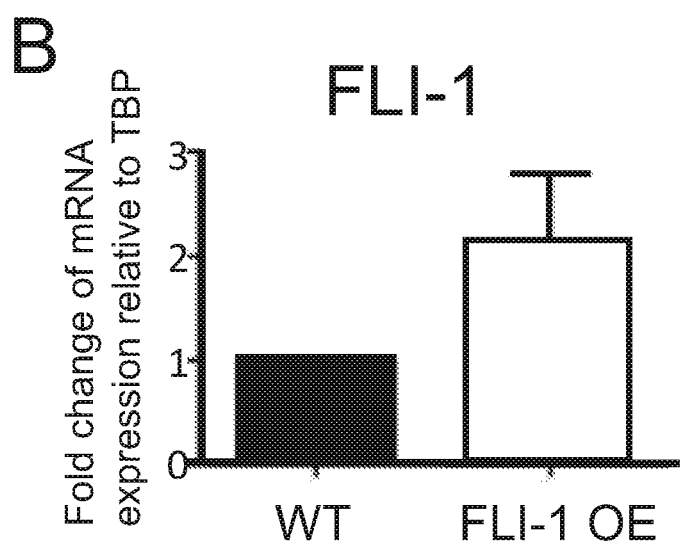
FIGS. 6A-B

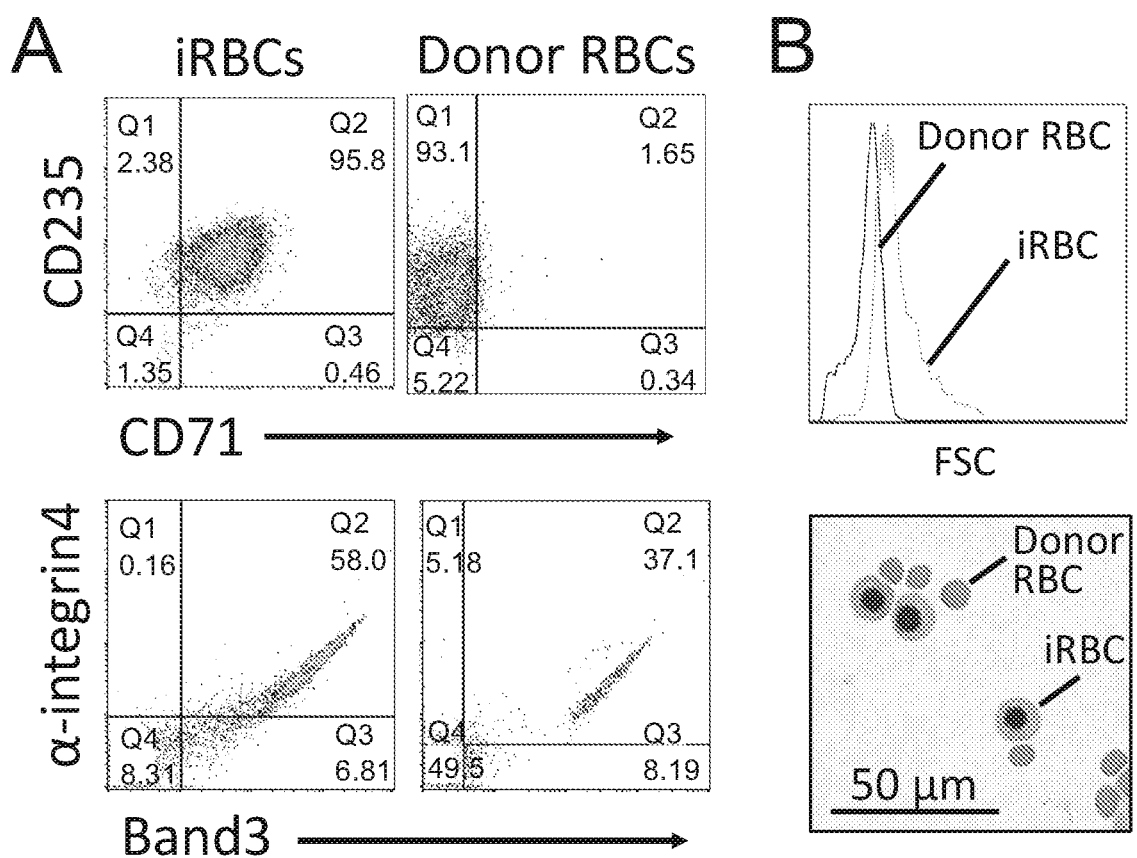
FIGS. 8A-B

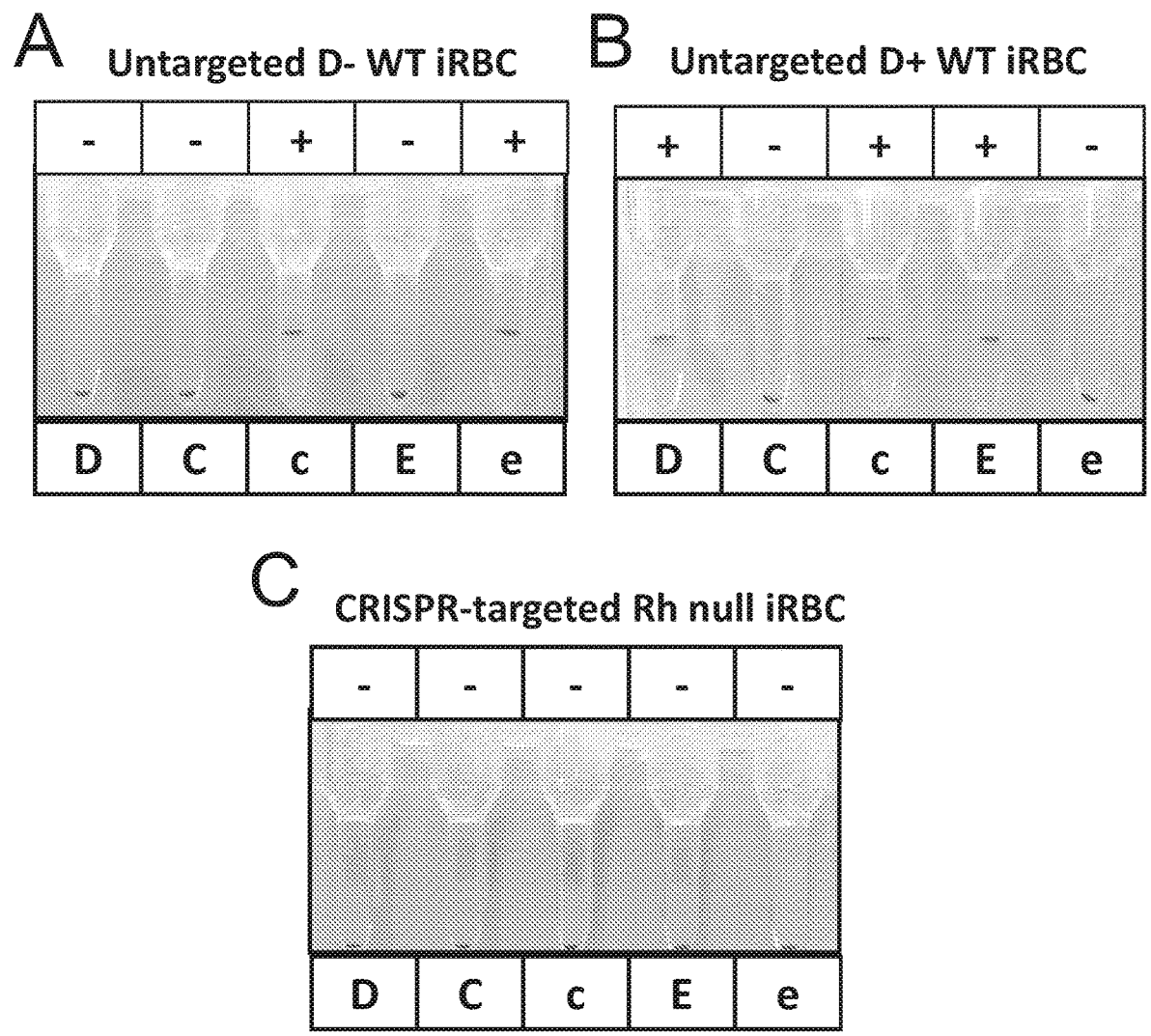
FIGS. 9A-C

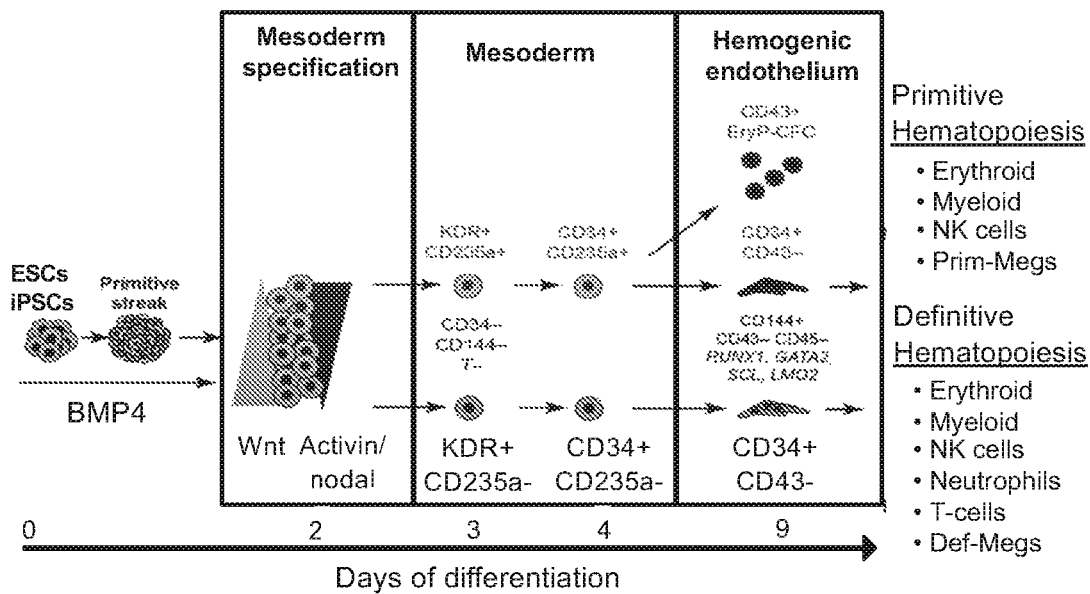
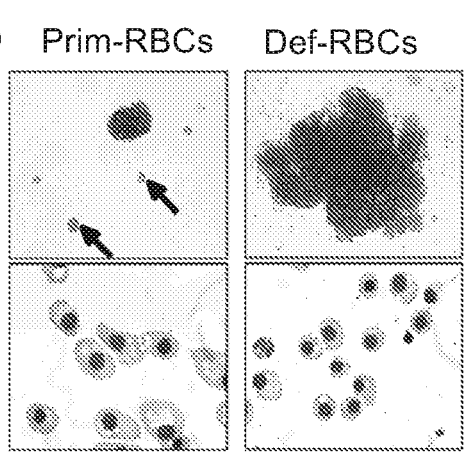
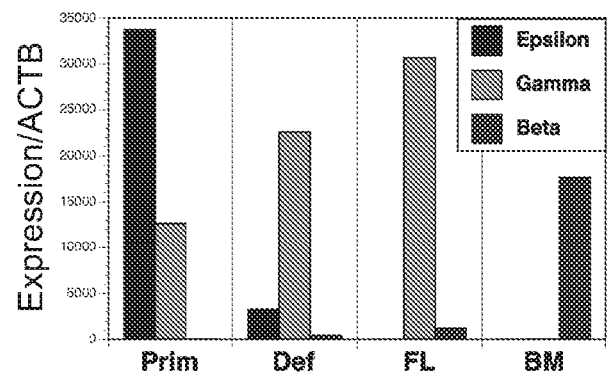
FIGS. 10A-C

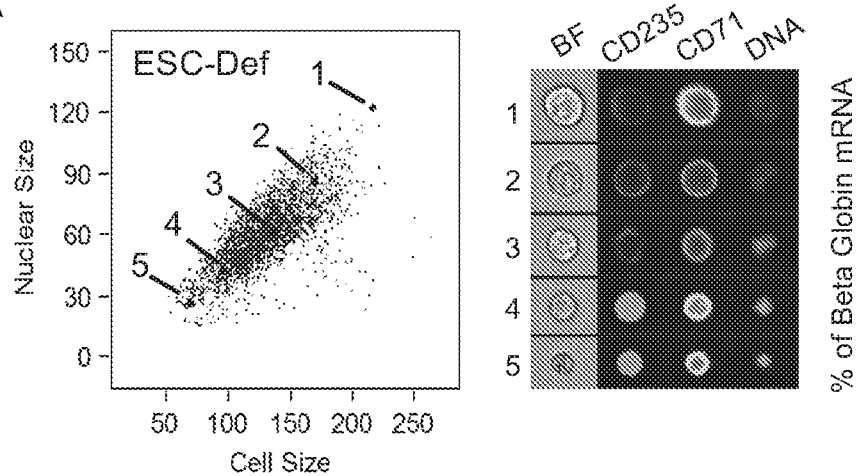
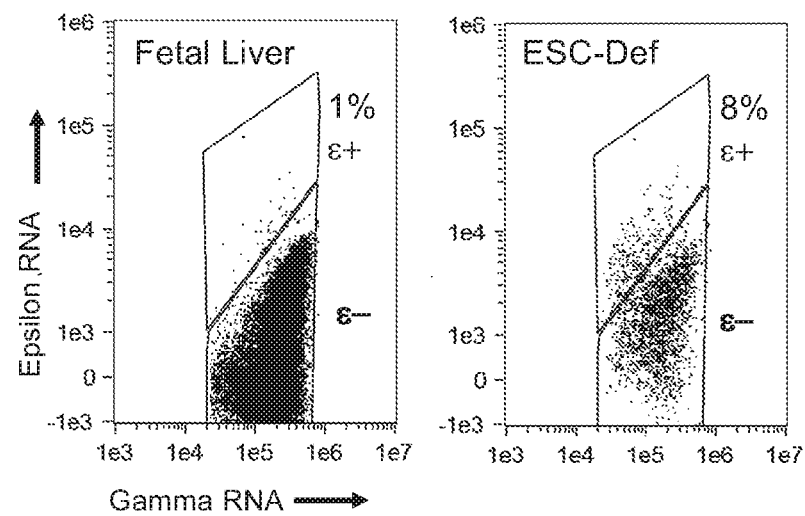
FIGS. 11A-B

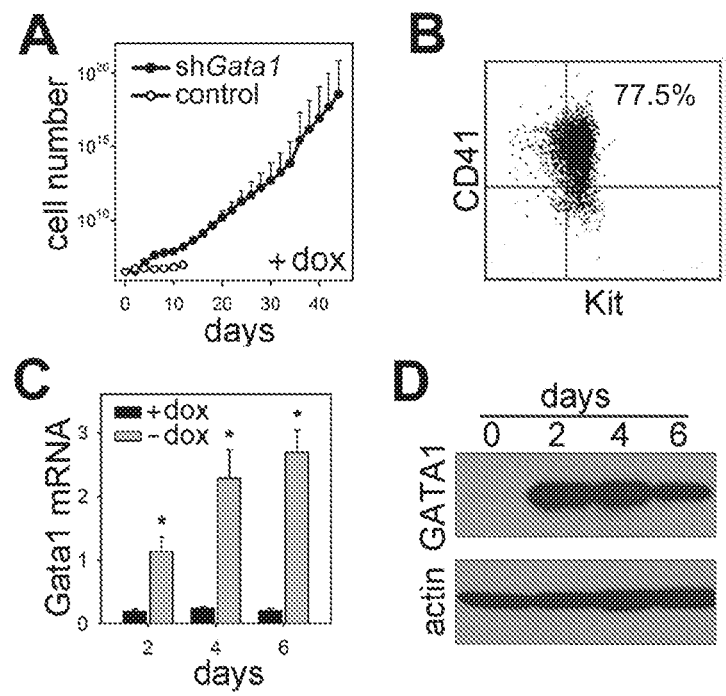
FIGS. 13A-D
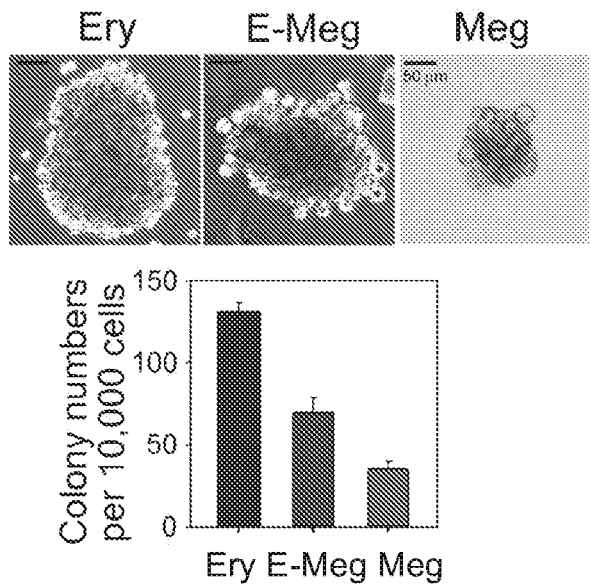
FIG. 14

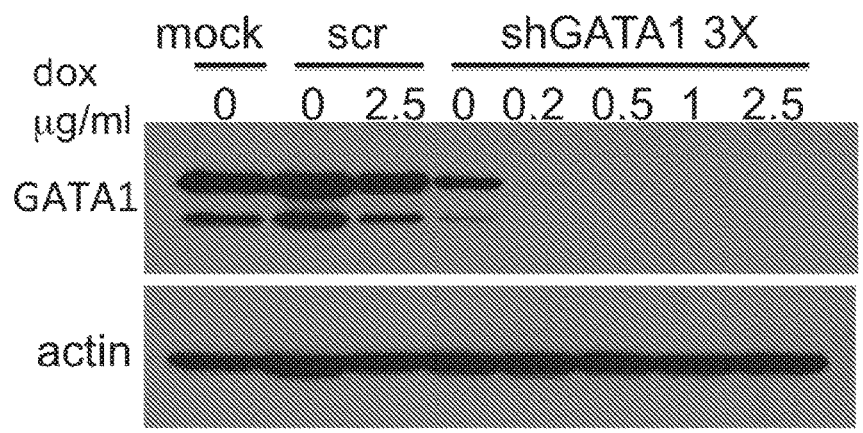
FIG. 17
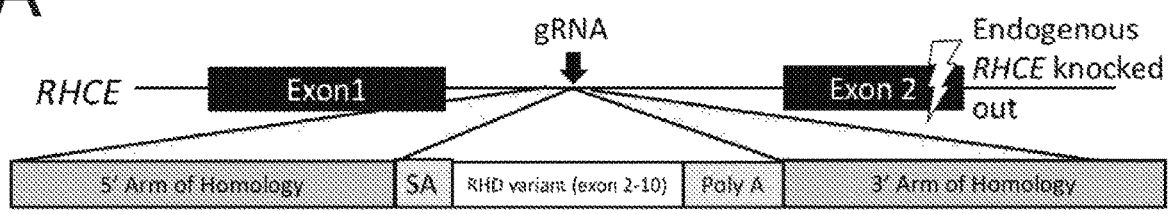
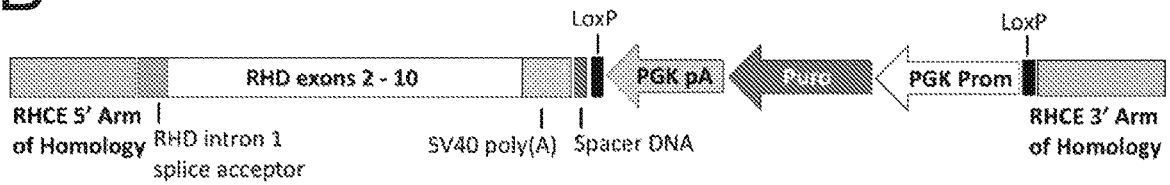
FIGS. 18A-B

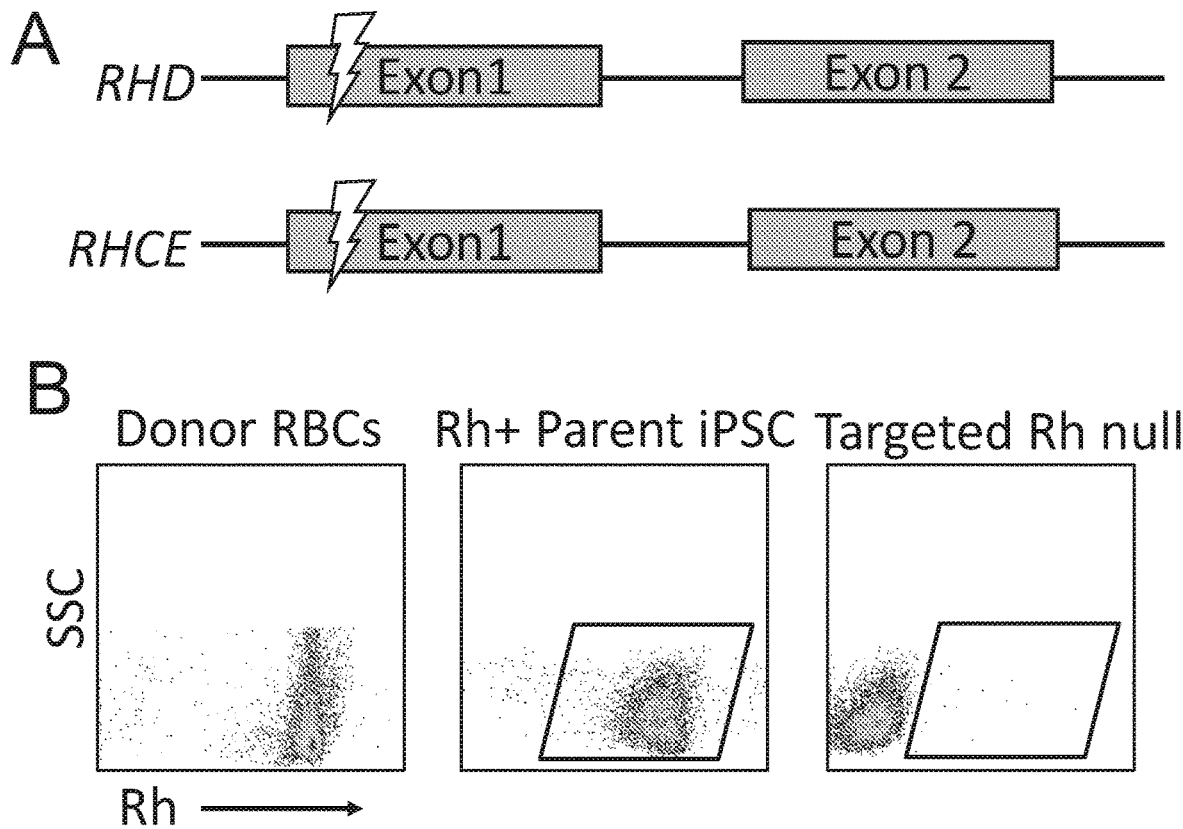
FIGS. 19A-B
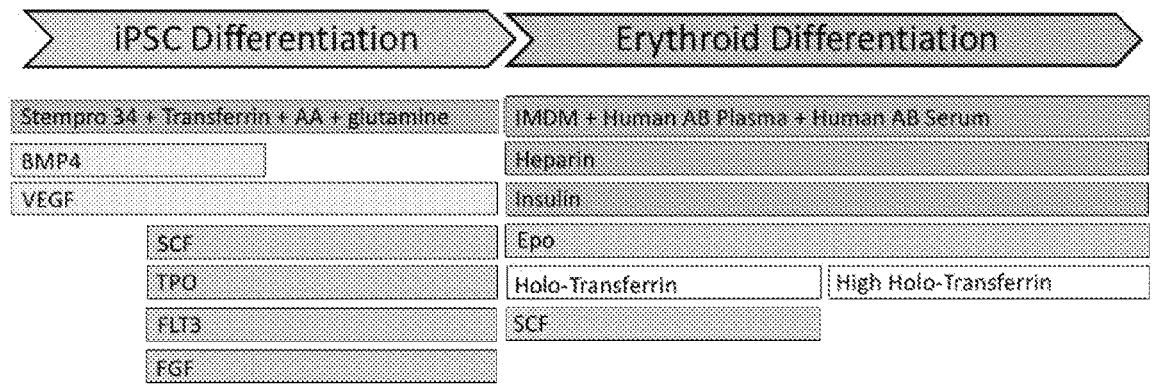
FIG. 20

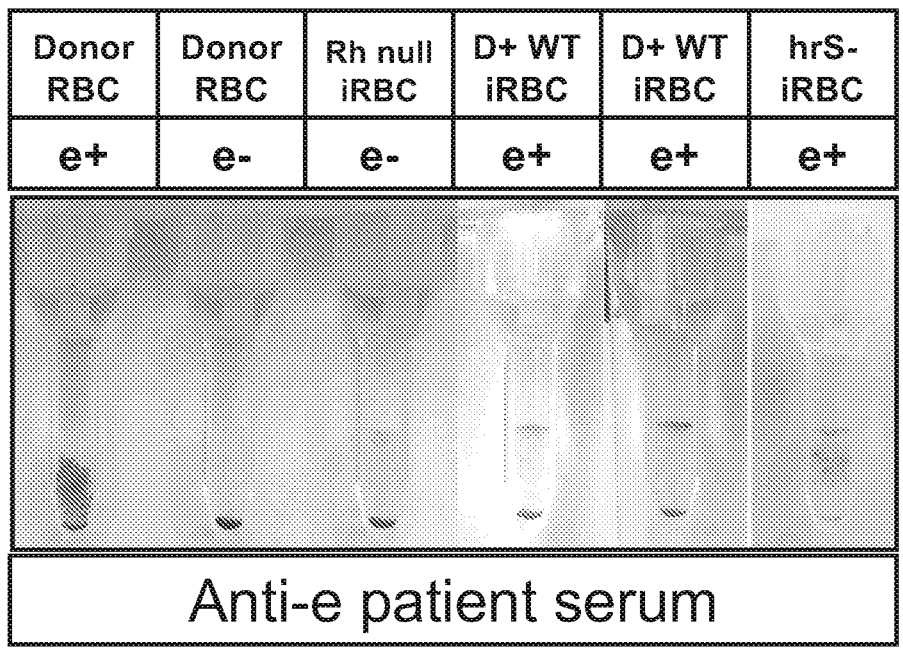
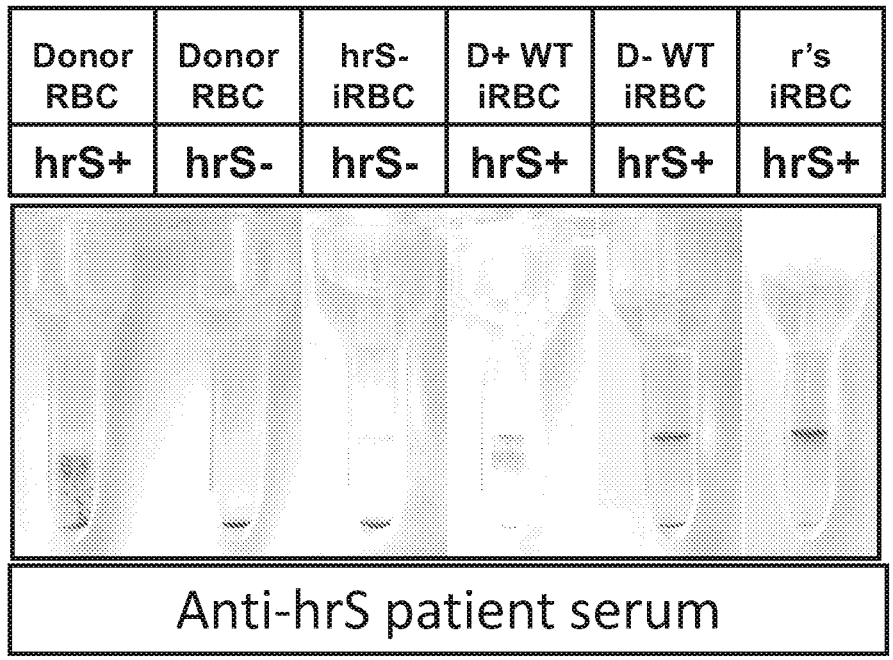
FIGS. 21A-B

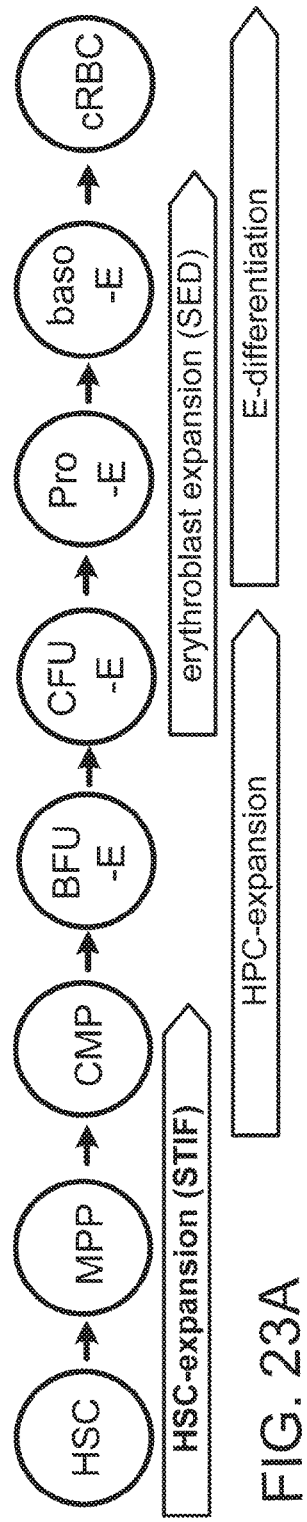
FIG. 23A
FIG. 23B
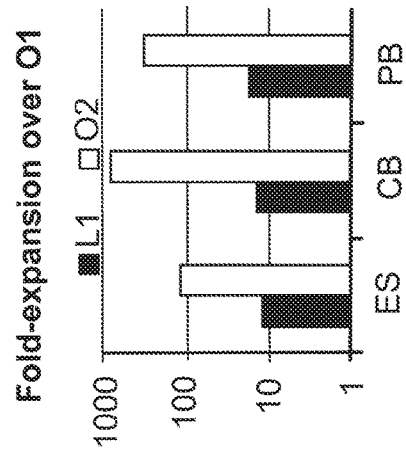
FIG. 23D
| | HSC-Expansion | HPC-expansion | E-diffe-rentiation | Cell yield | | |
|---|---|---|---|---|---|---|
| | | | | H1 ES | CB | PB |
| O1 | | | | 4.7E+02 ± 2.6E+02 | 2.5E+04 ± 1.5E+04 | 1.8E+04 ± 1.5E+04 |
| L1 | | | | 5.8E+03 ± 1.0E+03 | 3.5E+05 | 3.4E+05 ± 1.5E+04 |
| O2 | | | | 1.0E+04 ± 5.3E+03 | 2.0E+06 ± 1.2E+06 | 9.2E+05 ± 2.9E+05 |
FIG. 23C

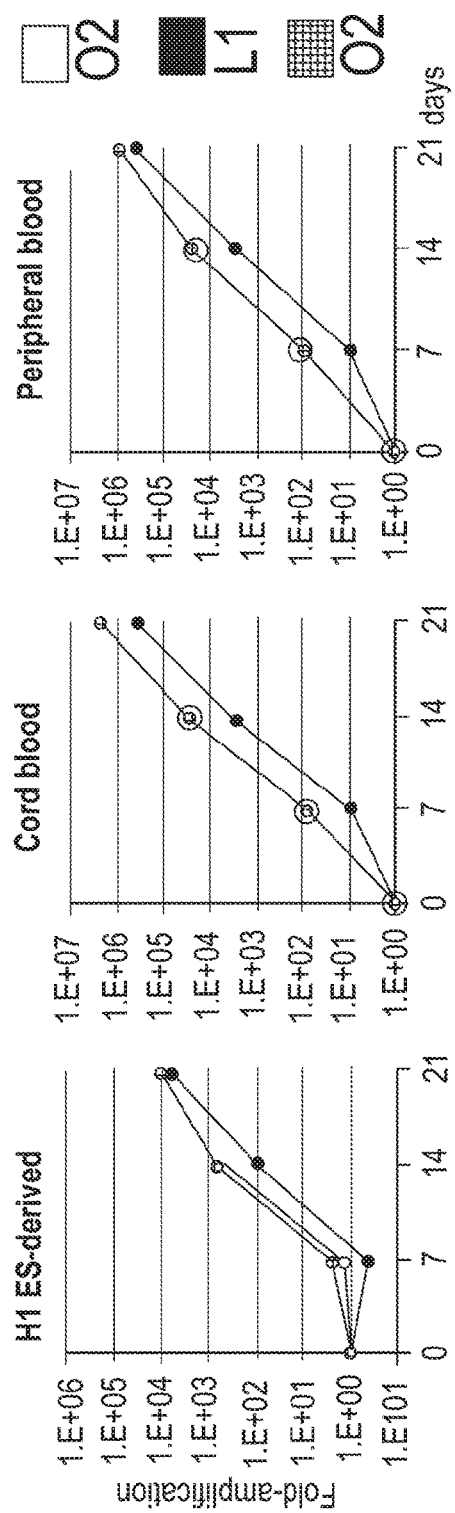
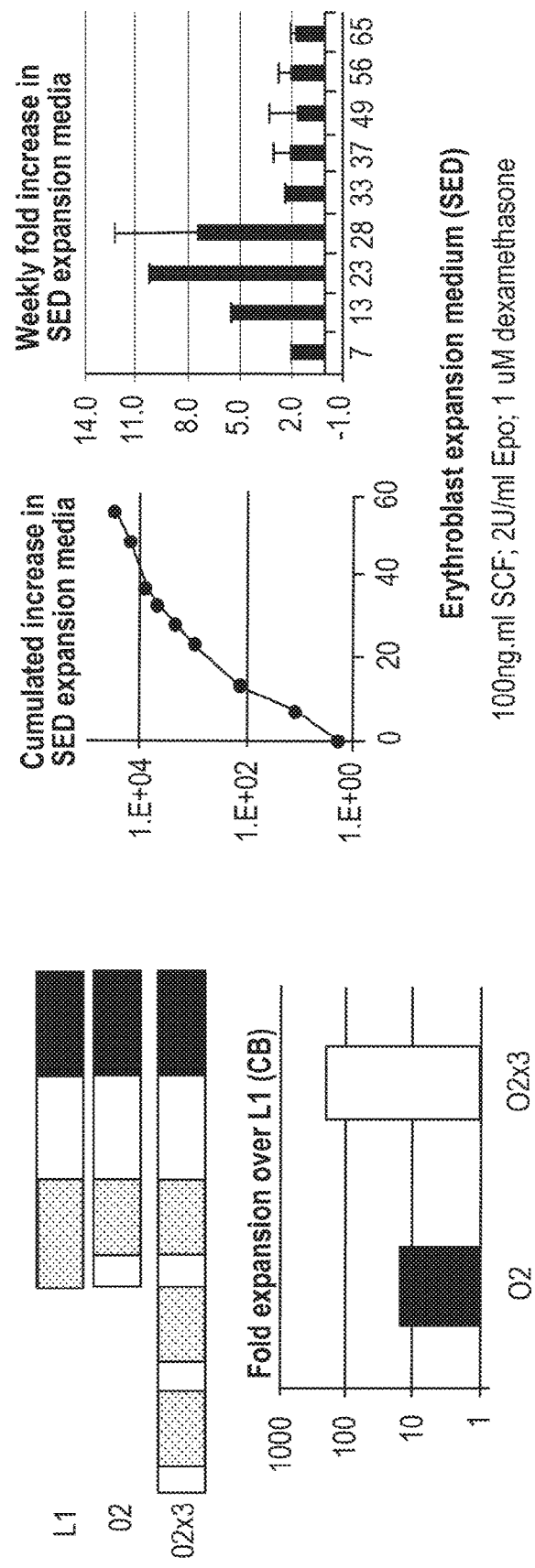
FIG. 23E
FIG. 23F
FIG. 23G

SEQUENCE LISTING

```
<160> NUMBER OF SEQ ID NOS: 3

<210> SEQ ID NO 1
<211> LENGTH: 47
<212> TYPE: DNA
<213> ORGANISM: Artificial Sequence
<220> FEATURE:
<223> OTHER INFORMATION: Synthetic primer

<400> SEQUENCE: 1
catgttcaac acctactatg ctctagcagt cagtgtggtg acagcca        47

<210> SEQ ID NO 2
<211> LENGTH: 47
<212> TYPE: DNA
<213> ORGANISM: Artificial Sequence
<220> FEATURE:
<223> OTHER INFORMATION: Synthetic primer

<400> SEQUENCE: 2
catgttcaac acctactatg ctgtagcagt cagtgtggtg acagcca        47

<210> SEQ ID NO 3
<211> LENGTH: 47
<212> TYPE: DNA
<213> ORGANISM: Artificial Sequence
<220> FEATURE:
<223> OTHER INFORMATION: Synthetic primer

<400> SEQUENCE: 3
catgttcaac acctactatg ctgttgcagt gtcagttgtg acagcca        47
```

ENGINEERED RED BLOOD CELLS HAVING RARE ANTIGEN PHENOTYPES

PRIORITY CLAIM

This application is a national phase application under 35 U.S.C, § 371 of International Application No. PCT/US2018/057932, filed Oct. 29, 2018, which claims benefit of priority to U.S. Provisional Patent Application No. 62/578,263, filed Oct. 27, 2017, and U.S. Provisional Patent Application No. 62/578,768, filed Oct. 30, 2017, the entire contents of each application being hereby incorporated by reference.

Pursuant to 37 C.F.R. 1.821(c), a sequence listing is submitted herewith as an ASCII compliant text file named "CHOPP0014US_ST25.txt", created on Apr. 20, 2020 and having a size of ~1 kilobytes. The content of the aforementioned file is hereby incorporated by reference in its entirety.

GOVERNMENT SUPPORT

This invention was made with government support under grant nos. HL130764-01 and HL134696-01 awarded by the National Institutes of Health. The government has certain rights in the invention.

I. TECHNICAL FIELD

The present disclosure relates to the fields of molecular biology, medicine and immunology, More specifically, it relates to engineered red blood cells having rare antigen phenotypes and/or the production of recombinant reagent red blood cells that do not express at least one antigen on its surface or express rare or unique combinations of antigens not found in natural human populations and uses of the same, e.g., their use in testing for blood type antibody reactivity in transfusion settings.

II. BACKGROUND

Transfusion of red blood cells (RBCs) is routinely used for many clinical and surgical applications. RBC transfusions were developed over 80 years ago, before all other cellular therapies, and are one of the most frequently used life-saving medical procedures. Blood transfusions are also a primary treatment for blood loss and hereditary anemia, including $\vartheta$-thalassemia major and sickle cell disease (SCD). According to the American Association of Blood Banks, 29 million units of blood components are transfused annually in the United States. This procedure has saved many lives. The demand for such transfusions continues to increase with advances in medical treatments and an aging population.

There are more than 30,000 patients transfused at least 6 times a year in the U.S. for chronic anemia and many are allo-immunized. Antibody screening against commercial reagent cells is performed prior to each transfusion. The current estimated cost for antibody identification in allo-immunized patients prior to transfusion is $100 to $200 million per year in the United States. Referral laboratory testing and performing multiple adsorptions to detect underlying alloantibodies contributes significantly ($500 to $2,000/per event) to this cost. Development of novel reagent red cells could reduce these costs by approximately 70% while improving safety.

Unfortunately, a major challenge is the high rate of alloimmunization (antibody formation against transfused red blood cells) that occurs in transfused patients. Genetic diversity in blood group antigens in patients of African descent (relevant for treatment of sickle cell disease), as compare to the primarily European-based blood donor pool, contributes to this high incidence and complexity of antibodies found in patients with sickle cell disease. At present, there is no ready solution to this challenging problem.

In order to better manage transfusion alloimmune responses, it would be most useful to be able to easily screen patients for alloimmunity, with an eye towards using such information to avoid use of blood products more likely to trigger dangerous reactions. In particular, a panel of rare blood types that would permit rapid screening.

SUMMARY

A major problem for transfusion therapy for chronic anemia is the high degree of genetic diversity in blood group antigens in people of Asian and African backgrounds compared to white Europeans, who are the majority of blood donors. These polymorphic antigens on RBCs contribute to the high incidence of allo-immunization and presence of multiple antibodies in the serum of these patients. Identifying the specificity of these antibodies and determining if they are auto- or allo-antibodies is critical for providing compatible blood or blood products. However, the current process can be complex, often involves costly reference laboratory testing, lacks standardization, and is hampered by the lack of suitable reagent RBCs for timely provision of blood products.

Recombinant reagent cultured red blood cells (cRBCs) will facilitate antibody identification in allo-immunized multiply transfused patients, and streamline and standardize testing.

The present disclosure is based, at least in part, on the generation of a novel and improved system for displaying recombinant proteins on the surface of eukaryotic cells (e.g., mammalian cells, e.g., reagent red blood cells). As elaborated on below and exemplified in the working examples, the system offers several benefits over those previously described.

Thus, in accordance with the present disclosure, there is provided a plurality of antigenically distinct engineered red blood cells (RBCs), wherein said plurality of RBCs exhibit distinct blood antigen group profiles, including at least two rare blood antigen groups. The plurality of RBCs may exhibit at least three, four, five, six, seven, eight, nine, ten or fifteen distinct blood antigen groups. The plurality of RBCs may be immortalized from naturally-occurring isolated RBCs, such as by transfecting a naturally-occurring RBC with a construct expressing a transforming oncoprotein. The plurality of RBCs may be produced from induced pluripotent stem cells, such as those produced from induced pluripotent stem cells using CRISPR to insert, delete or disrupt a coding sequence for one or more blood antigens.

The plurality of RBCs may comprise two or more of the following blood antigen group profiles: Rh null, D -/-, U/S/s antigen negative (glycophorin B null), RHCE negative, positive for low prevalence RhD antigens, Dombrok (Do) null, and Lutheran null. The plurality of RBCs may further comprise one or more of Kell positive, Kidd positive, Duffy positive and MNS antigen positive. The plurality of RBCs may comprise three, four, five or all six blood antigen group profiles.

In another embodiment there is provided a plurality of antigenically distinct induced pluripotent stem cells (IPSCs), wherein said plurality of IPSCs exhibit distinct blood antigen group profiles, including at least two rare blood antigen groups. The plurality of IPSCs may exhibit at least three, four, five, six, seven, eight, nine, ten or fifteen distinct blood antigen groups. The plurality of IPSCs may be produced from induced pluripotent stem cells using CRISPR to insert, delete or disrupt a coding sequence for one or more blood antigens. The plurality of IPSCs may comprise two or more of the following blood antigen group profiles: Rh null, D −/−, U/S/s antigen negative (glycophorin B null), RHCE negative, positive for low prevalence RhD antigens, Dombrok (Do) null, and Lutheran null. The plurality of IPSCs may further comprise one or more of Kell positive, Kidd positive, Duffy positive and MNS antigen positive. The IPSCs may comprise three, four, five or all six blood antigen group profiles.

In yet another embodiment, there is provided a plurality of antigenically distinct engineered erythroblasts, wherein said plurality of erythroblasts exhibit distinct blood antigen group profiles, including at least two rare blood antigen groups. The plurality of erythroblasts may exhibit at least three, four, five, six, seven, eight, nine, ten or fifteen distinct blood antigen groups. The plurality of erythroblasts may be produced from induced pluripotent stem cells. The plurality of erythroblastis may comprise two or more of the following blood antigen group profiles: Rh null, D −/−, U/S/s antigen negative (glycophorin B null), RHCE negative, positive for low prevalence RhD antigens, Dombrok (Do) null, and Lutheran null, and optionally further comprise one or more of Kell positive, Kidd positive, Duffy positive and MNS antigen positive. The plurality of erythroblasts may comprise three, four, five or all six blood antigen group profiles.

In still yet another embodiment, there is provided a method of identifying blood antigen group-specific antibodies in a subject comprising (a) obtaining a subject sample comprising antibodies; (b) contacting said sample with the plurality of antigenically distinct engineered RBCs as described above; and (c) identifying binding of said antibodies to one or more of said antigenically distinct engineered RBCs. Step (c) may comprise an agglutination assay, such as a gel card assay, or step (c) may comprise an ELISA, an RIA or flow cytometry.

The subject may be a human subject. The subject may suffer from a disease treating by blood transfusion, such as sickle cell disease, thalassemia, a hemoglobinopathy, congenital anemias (e.g., pyruvate kinase deficiency; blackfan anemia), bone marrow failure syndromes, myelodysplastic syndromes, multiple myeloma, or cancer. The sample may be whole blood, plasma, or serum. The subject may have previously had a blood transfusion or a pregnancy. The subject may not have previously had a blood transfusion or a pregnancy.

In still a further embodiment, there is provided a method of producing an engineered red blood cell (RBC) comprising (a) providing an induced pluripotent stem cell (iPSC); (b) modifying said iPSC to express a blood group antigen and/or not express a blood group antigen; and (c) inducing differentiation of said iPSC into an erythroblast and thereafter into a mature RBC. The method may further comprise causing said RBC to become enucleated. The RBC may be Rh null, D −/−, U/S/s antigen negative (glycophorin B null), RHCE negative, positive for low prevalence RhD antigens, Dombrok (Do) null, or Lutheran null. Modifying may comprise use of CRISPR to insert, delete or disrupt a coding sequence for one or more blood antigens.

Provided herein are recombinant red blood cells, wherein the recombinant red blood cells have a surface phenotype selected from the group consisting of: (i) D$^-$, C$^-$, E$^-$, c$^-$, e$^-$; (ii) D$^+$, C$^-$, E$^-$, c$^-$, e$^-$; (iii) D$^-$, U$^-$, S$^-$, s$^-$; (iv) D$^-$, hrB$^-$, VS$^+$; (v) D$^-$, hrB$^-$, hrS$^-$; (vi) C$^-$, E$^-$, c$^-$, e$^-$; (vii) D$^+$, C$^-$, E$^-$, c$^-$, e$^-$, Go(a)$^+$; (viii) D$^+$, C$^-$, E$^-$, c$^-$, e$^-$, DAK$^+$; (ix) D$^-$, Doa$^-$, Dob$^-$; (x) Lua$^-$ b$^-$; (xi) CD47$^-$; and (xii) any combination of two or more of the surface phenotypes of (i) to (xi).

Provided herein are recombinant red blood cells, wherein the recombinant red blood cells are characterized by the absence of at least one or more cell surface antigens on its surface selected from the group consisting of: a C antigen, an E antigen, a c antigen, an e antigen, a U antigen, an S antigen, an s antigen, an hrB antigen, a Lua antigen, a Lub antigen and a CD47 antigen.

In some embodiments, the recombinant red blood cell is characterized by the absence of at least ten of the one or more cell surface antigens.

In some embodiments, the recombinant red blood cell is characterized by the absence of at least eight of the one or more cell surface antigens.

In some embodiments, the recombinant red blood cell is characterized by the absence of at least four of the one or more cell surface antigens.

In some embodiments, the recombinant red blood cell is characterized by the absence of at least two of the one or more cell surface antigens.

In some embodiments of any of the recombinant red blood cells described herein, the recombinant red blood cell is further characterized by the absence of a D antigen on its cell surface.

In some embodiments of any of the recombinant red blood cells described herein, the recombinant red blood cell is further characterized by the presence of a D antigen on its cell surface.

In some embodiments of any of the recombinant red blood cells described herein, the recombinant red blood cell is further characterized by the presence of a Go(a) antigen on its cell surface.

In some embodiments of any of the recombinant red blood cells described herein, the recombinant red blood cell is further characterized by the presence of a DAK antigen on its cell surface.

In some embodiments of any of the recombinant red blood cells described herein, the recombinant red blood cell is characterized by the absence of a Doa antigen and a Dob antigen on its cell surface.

Also provided herein are kits that include: a solid support; a first reagent red blood cell characterized by the presence of one or more cell surface antigens on its surface; and a second reagent red blood cell characterized by the absence of at least one of the one or more cell surface antigens on its surface; wherein: the one or more cell surface antigens are selected from the group consisting of: a C antigen, an E antigen, a c antigen, an e antigen, a U antigen, an S antigen, an s antigen, an hrB antigen, a Lua antigen, a Lub antigen and a CD47 antigen; and the first reagent red blood cell and the second reagent red blood cell have the same surface phenotype, except for the at least one cell surface antigen.

In some embodiments of any of the kits described herein, the kit further includes one or more additional reagent red blood cell, wherein: each additional reagent red blood cell has a surface phenotype that is characterized, at least in part, by the absence of one or more cell surface antigens; and each reagent red blood cell present in the kit has a different surface phenotype as compared to all the other reagent red blood cells in the kit.

In some embodiments, the kit includes at least 10 additional reagent red blood cells.

In some embodiments, the second reagent red blood cell is characterized by the absence of a C antigen, an E antigen, a c antigen, and an e antigen on its cell surface.

In some embodiments, the second reagent red blood cell is further characterized by the absence of a D antigen on its cell surface.

In some embodiments, the second reagent red blood cell is further characterized by the presence of a D antigen on its cell surface.

In some embodiments, the second reagent red blood cell is characterized by the absence of a U antigen, a S antigen, and a s antigen on its cell surface.

In some embodiments, the second reagent red blood cell is further characterized by the absence of a D antigen on its cell surface.

In some embodiments, the second reagent red blood cell is characterized by the presence of a D antigen on its cell surface and the absence of a C antigen, an E antigen, a c antigen, and an e antigen on its cell surface.

In some embodiments, the second reagent red blood cell is further characterized by the presence of a Go(a) antigen on its cell surface.

In some embodiments, the second reagent red blood cell is further characterized by the presence of a DAK antigen on its cell surface.

In some embodiments, the second reagent red blood cell is characterized by the absence of a Doa antigen and a Dob antigen on its cell surface.

In some embodiments, the second reagent red blood cell is characterized by the absence of an hrB antigen on its cell surface.

In some embodiments, the second reagent red blood cell is further characterized by the absence an hrS antigen on its cell surface.

In some embodiments, the second reagent red blood cell is further characterized by the absence a D antigen on its cell surface.

In some embodiments, the second reagent red blood cell is further characterized by the presence of a VS antigen on its cell surface.

In some embodiments, the second reagent red blood cell is characterized by the absence of a C antigen, an E antigen, a c antigen, an e antigen, a U antigen, a S antigen, an s antigen and an hrB antigen on its cell surface.

In some embodiments, the second reagent red blood cell is characterized by a phenotype selected from the group consisting of: (i) $D^-$, $C^-$, $E^-$, $c^-$, $e^-$; (ii) $D^+$, $C^-$, $E^-$, $c^-$, $e^-$; (iii) $D^-$, $U^-$, $S^-$, $s^-$; (iv) $D^-$, $hrB^-$, $VS^+$; (v) $D^-$, $hrB^-$, $hrS^-$; (vi) $C^-$, $E^-$, $c^-$, $e^-$; (vii) $D^+$, $C^-$, $E^-$, $c^-$, $e^-$, $Go(a)^+$; (viii) $D^+$, $C^-$, $E^-$, $c^-$, $e^-$, $DAK^+$; (ix) $D^-$, $Doa^-$, $Dob^-$; (x) $Lua^-b^-$; (xi) $CD47^-$; and (xii) any combination of two or more of the surface phenotypes of (i) to (xi).

In some embodiments, the second reagent red blood cell is characterized by the absence of a C antigen, an E antigen, a c antigen, an e antigen, a U antigen, a S antigen, an s antigen and an hrB antigen on its cell surface.

In some embodiments of any of the kits described herein, the solid support is selected from the group consisting of: a gel card, a multi-well assay plate, an array, a microplate, a film, a tube, a well, a capillary, a paper matrix, a slide, and a chip.

Provided herein are methods of determining blood group antigen compatibility of a patient sample that include: (a) contacting a first reagent red blood cell with a patient sample containing a plurality of antibodies; wherein the first reagent red blood cell is characterized by the presence of one or more blood group antigens on its surface; and (b) contacting a second reagent red blood cell with the patient sample; wherein the second reagent red blood cell is characterized by the absence of at least one of the one or more cell surface antigens on its surface; (c) detecting whether agglutination occurs upon contacting the first reagent red blood cell with the patient sample; (d) detecting whether agglutination occurs when contacting the second reagent blood cell with the patient sample; and (e) identifying that the patient sample is compatible with the at least one of the one or more cell surface antigens when no agglutination is detected in steps (c) and (d), or identifying that the patient sample is not compatible with the at least one of the one or more cell surface antigens when agglutination is detected in step (c) but is not detected in step (d), wherein: the one or more cell surface antigens are selected from the group consisting of: a C antigen, an E antigen, a c antigen, an e antigen, a U antigen, an S antigen, an s antigen, and an hrB antigen, and the first reagent red blood cell and the second reagent red blood cell have the same surface phenotype, except for the at least one cell surface antigen.

In some embodiments, identifying that the patient sample is not compatible with the at least one of the one or more cell surface antigens when agglutination is detected in step (c) but is not detected in step (d).

In some embodiments, the method includes the use of one or more additional reagent red blood cells, wherein: each additional reagent red blood cell has a surface phenotype that is characterized, at least in part, by the absence of one or more cell surface antigens; and each reagent red blood cell used in the method has a different surface phenotype as compared to all the other reagent red blood cells used in the method.

In some embodiments, the method includes the use of ten or more additional reagent red blood cells.

In some embodiments, the first reagent red blood cell is characterized by the presence of a C antigen, an E antigen, a c antigen, and an e antigen on its cell surface.

In some embodiments, the first reagent red blood cell is further characterized by the presence of a D antigen on its cell surface.

In some embodiments, the first reagent red blood cell is further characterized by the absence of a D antigen on its cell surface.

In some embodiments, the second reagent red blood cell is characterized by the absence of a U antigen, an S antigen, and an s antigen on its cell surface.

In some embodiments, the second reagent red blood cell is further characterized by the absence of a D antigen on its cell surface.

In some embodiments, the second reagent red blood cell is characterized by the absence of a D antigen on its cell surface and the absence of a C antigen, an E antigen, a c antigen, and an e antigen on its cell surface.

In some embodiments, the second reagent red blood cell is further characterized by the presence of a Go(a) antigen on its cell surface.

In some embodiments, the second reagent red blood cell is further characterized by the presence of a DAK antigen on its cell surface.

In some embodiments, the second reagent red blood cell is characterized by the presence of a Doa antigen and a Dob antigen on its cell surface.

In some embodiments, the second reagent red blood cell is characterized by the absence of an hrB antigen on its cell surface.

In some embodiments, the second reagent red blood cell is further characterized by the absence an hrS antigen on its cell surface.

In some embodiments, the second reagent red blood cell is further characterized by the absence a D antigen on its cell surface.

In some embodiments, the second reagent red blood cell is further characterized by the presence of a VS antigen on its cell surface.

In some embodiments, the second reagent red blood cell is characterized by the absence of a C antigen, an E antigen, a c antigen, an e antigen, a U antigen, an S antigen, an s antigen, a hrS antigen and a hrB antigen on its cell surface.

In some embodiments, the second target red blood cell is characterized by a phenotype selected from the group consisting of: (i) $D^-$, $C^-$, $E^-$, $c^-$, $e^-$; (ii) $D^+$, $C^-$, $E^-$, $c^-$, $e^-$; (iii) $D^-$, $U^-$, $S^-$, $s^-$; (iv) $D^-$, $hrB^-$, $VS^+$; (v) $D^-$, $hrB^-$, $hrS^-$; (vi) $C^-$, $E^-$, $c^-$, $e^-$; (vii) $D^+$, $C^-$, $E^-$, $c^-$, $e^-$, $Go(a)^+$; (viii) $D^+$, $C^-$, $E^-$, $c^-$, $e^-$, $DAK^+$; (ix) $D^-$, $Doa^-$, $Dob^-$; and (x) any combination of two or more of the surface phenotypes of (i) to (ix).

In some embodiments of any of the methods described herein, the method further includes: selecting a tissue or blood product that is compatible with the at least one of the one or more cell surface antigens for a patient having its patient sample identified as being compatible with the at least one of the one or more cell surface antigens; or selecting a tissue or blood product that does not include the at least one of the one or more cell surface antigens for a patient having its patient sample identified as not being compatible with the at least one of the one or more cell surface antigens.

In some embodiments, the method further includes: administering the selected tissue or blood product that is compatible with the at least one of the one or more cell surface antigens to the patient having its patient sample identified as being compatible with the at least one of the one or more cell surface antigens; or administering the selected tissue or blood product that does not include the at least one of the one or more cell surface antigens to the patient having its patient sample identified as not being compatible with the at least one of the one or more cell surface antigens.

In some embodiments, the patient has hereditary anemia. In some embodiments, the patient has β-thalassemia. In some embodiments, the patient has sickle cell disease.

Also provided herein are methods of determining blood compatibility of a patient sample that include: (a) contacting a first reagent red blood cell with a patient sample containing a plurality of antibodies; wherein the first reagent red blood cell is characterized by the presence of one or more cell surface antigens; and (b) contacting a second reagent red blood cell with the patient sample; wherein the second reagent red blood cell is characterized by the absence of at least one of the one or more cell surface antigens on its surface; (c) detecting whether agglutination occurs upon contacting the first reagent red blood cell with the patient sample; (d) detecting whether agglutination occurs when contacting the second reagent blood cell with the patient sample; and (e) identifying that the patient sample is compatible with the at least one of the one or more cell surface antigens when no agglutination is detected in steps (c) and (d), or identifying that the patient sample is not compatible with the at least one of the one or more cell surface antigens when agglutination is detected in step (c) but is not detected in step (d), wherein: the one or more cell surface antigens are selected from the group consisting of: a Lua antigen, a Lub antigen, and a CD74 antigen, and the first reagent red blood cell and the second reagent red blood cell have the same surface phenotype, except for the at least one cell surface antigen.

In some embodiments, the method includes the use of one or more additional reagent red blood cells, wherein: each additional reagent red blood cell has a surface phenotype that is characterized, at least in part, by the absence of one or more cell surface antigens; and each reagent red blood cell used in the method has a different surface phenotype as compared to all the other reagent red blood cells used in the method.

In some embodiments, the method includes the use of ten or more additional reagent red blood cells.

In some embodiments, the second reagent red blood cell is characterized by the absence of a Lua antigen and a Lub antigen on its cell surface.

In some embodiments, the second reagent red blood cell is characterized by the absence of a CD47 antigen.

In some embodiments, the sample is obtained from a patient that has received an anti-CD38 immunotherapy.

In some embodiments, the sample is obtained from a patient that has received an anti-CD47 immunotherapy.

In some embodiments of any of the methods described herein, the method further includes: selecting a tissue or blood product that is compatible with the at least one of the one or more cell surface antigens for a patient having its patient sample identified as being compatible with the at least one of the one or more cell surface antigens; or selecting a tissue or blood product that does not include the at least one of the one or more cell surface antigens for a patient having its patient sample identified as not being compatible with the at least one of the one or more cell surface antigens.

In some embodiments, the method further includes: administering the selected tissue or blood product that is compatible with the at least one of the one or more cell surface antigens to the patient having its patient sample identified as being compatible with the at least one of the one or more cell surface antigens; or administering the selected tissue or blood product that does not include the at least one of the one or more cell surface antigens to the patient having its patient sample identified as not being compatible with the at least one of the one or more cell surface antigens.

In some embodiments of any of the methods described herein, the patient sample is a plasma sample or a serum sample.

In some embodiments of any of the methods described herein, the method further includes: transfusing a therapeutically effective amount of a second reagent red blood cell to the patient having its patient sample identified as being compatible with the at least one of the one or more cell surface antigens; and, wherein the second reagent red blood cell has a phenotype selected from the group consisting of: (i) $Lua^- b^-$; and (ii) $CD47^-$.

As used herein, the terms "reagent red blood cell," "reagent cultured red blood cell" and "recombinant red blood cell" are used interchangeably. A reagent red blood cell has all of the functional and morphological characteristics of a naturally-occurring red blood, but has been genetically modified (or a precursor cell to the reagent red blood cell has been genetically modified) in vitro. In some embodiments, reagent red blood cells described herein can lack the expression of one or more blood group antigens that are expressed on naturally-occurring red blood cells, or express rare antigens or combinations of antigens not found often, if ever, in humans.

The term "surface phenotype" refers to the collection of antigens present on the surface of a red blood cell. In some embodiments, an antigen present on the surface of a red blood cell can be a transmembrane protein or a carbohydrate moiety on a protein. In some embodiments, an antigen present on the surface of a red blood cell can be covalently attached to the plasma membrane of a red blood cell (e.g., GPI-anchored). In some embodiments, an antigen present on the surface of a red blood cell can be non-covalently bonded to the plasma membrane of a red blood cell (e.g., non-covalently bonded to a transmembrane protein in the plasma membrane of the red blood cell). For example, a first reagent red blood cell and a second reagent red blood can have the same or an indistinguishable surface phenotype except for the presence or absence of at least one cell surface antigen.

As used herein an array can, in some embodiments, refer to an ordered arrangement of bound antibodies that specifically bind to red blood cell antigens (e.g., any of the red blood cell antigens described herein) on a support surface (e.g., a microarray, a chip, a slide, a film, a gold coated surface, tubing, polymers, microparticles, plates, tubing, magnetic or nonmagnetic beads). In some aspects an array include at least about 2 antibodies (e.g., at least about 4 antibodies, at least about 6 antibodies, at least about 8 antibodies, at least about 10 antibodies). In some aspects, an array is made of glass, silicon, silicon oxide, metal oxides, metal, polymers (e.g., poly-L-lysine, aminopropylsilane, carboxysilane), hydrogels and polymer-brushes. In some aspects, the array is planar or spheroid. In some aspects, an array is about 20 mm to about 200 mm (e.g., about 20 mm to about 180 mm, about 20 mm to about 160 mm, about 20 mm to about 140 mm, about 20 mm to about 120 mm, about 20 mm to about 100 mm, about 20 mm to about 80 mm, about 20 mm to about 60 mm, about 20 mm to about 40 mm, about 30 mm to about 200 mm, about 30 mm to about 180 mm, about 30 mm to about 160 mm, about 30 mm to about 140 mm, about 30 mm to about 120 mm, about 30 mm to about 100 mm, about 30 mm to about 80 mm, about 30 mm to about 60 mm, about 40 mm to about 200 mm, about 40 mm to about 180 mm, about 40 mm to about 180 mm, about 40 mm to about 160 mm, about 40 mm to about 140 mm, about 40 mm to about 120 mm, about 40 mm to about 100 mm, about 40 mm to about 80 mm, about 40 mm to about 60 mm, or about 100 mm to about 200 mm), with up to 10,000 spots of antibodies (e.g., about 2 spots to about 10,000 spots, about 2 spots to about 2,000 spots, about 2 spots to about 1,000 spots, and any range in between). An array can be used to test more than one sample (e.g., 2, 4, 10, 20, 40, 60, 80 or 100 samples).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

It is contemplated that any method or composition described herein can be implemented with respect to any other method or composition described herein.

Other objects, features and advantages of the present disclosure will become apparent from the following detailed description and figures, and from the claims. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1. RBC panel for antibody detection. Each row represents the RBC antigen profile of a single donor and columns show presence (+) or absence (0) of the indicated antigen. Reagents 1-3 are standard commercial RBCs used for antibody detection. Autocontrol=patient RBCs which include endogenous and transfused RBCs. Bottom 3 rows represent rare reagent RBCs. Far right column shows graded reactivity of patient's serum to each reagent RBC.

FIGS. 3A-D. Alloimmunization in 182 patients with SCD transfused with D, C, E, K-matched RBCs from minority donors. FIG. 3A. Blue tag that accompanies RBC donation from a self-identified African American donor. FIG. 3B. 146 antibodies were identified and 70% had Rh specificity. FIG. 3C. 56 Rh antibodies occurred in patients whose RBCs typed positive for that antigen (sometimes mistaken for "autoantibodies"), and 35 were identified in antigen-negative patients despite transfusion with Rh-matched RBCs. FIG. 3D. % Hemoglobin S and hemoglobin of representative patient with altered RH, receiving RBC transfusions every 3 weeks. Arrows indicate new anti-e detection. Grey boxes represent +/−1.5 SD the calculated mean hemoglobin S and hemoglobin.

FIG. 4. RHD and RHCE alleles found in 857 patients with SCD and 587 African American donors. Each grey box represents 1 of 10 exons in the RH genes. Black boxes represent exon exchange between RHD and RHCE. Vertical lines indicate position in the exon encoding amino acid substitutions in the protein. Dashed line indicates gene deletion. Arrowhead indicated 37-bp duplication. Hatched boxes represent exons encoding a frameshift and untranslated region of the inactive RHD pseudogene.

FIGS. 5A-C. Gene-targeting with the CRISPR/Cas9 system. FIG. 5A. Schematic of targeting the ARX locus. The guide RNA of the CRISPR-Cas9 system targets a DNA break near the ATG. Using a gene-targeting vector, red fluorescent protein (Myr-RFP) is inserted into the beginning of ARX. FIG. 5B. Southern Blot showing correct gene targeting FIG. 5C. The ARX-RFP reporter cell line was differentiated and ARX visualized by RFP.

FIGS. 6A-B. Generation of a FLI-1 overexpression line. FIG. 6A. Schematic of targeting strategy (PR: puromycin resistance; Gp1ba: Gp1ba promoter; Hom-L: homology arm left; Hom-R: homology arm right; ZFN: zinc finger nuclease site; con: control). H9 ESCs with and without the FLI-1 overexpression construct were differentiated into hematopoietic cells. FIG. 6B. QRTPCR expression analysis of FLI-1 in purified Megs.

FIGS. 8A-B. Characteristics of induced pluripotent stem cell derived red blood cells (iRBCs). (FIG. 8A) Cell surface expression of red cell markers on iRBCs compared to donor derived RBCs. (FIG. 8B) iRBC size shown by forward scatter (FSC) on flow cytometry histogram and by cytospin as compared to donor derived RBCs.

FIGS. 9A-C. Accurate Rh typing of induced pluripotent stem cell derived red blood cells (iRBCs). Using monoclonal Rh typing reagents for D, C, c, E, and e, typing was performed with 500,000 iRBCs per gel card assay column for Untargeted D− wild type (WT) iRBCs (FIG. 9A), untargeted D+ WT iRBCs (FIG. 9B), and CRISPR-targeted Rh null iRBCs (FIG. 9C). The Rh phenotype predicted by genotype is shown in light grey boxes. iRBCs agglutinated and remained at the top of the gel matrix when the antigen was predicted to be expressed (+) and did not agglutinate and pelleted to bottom of column when antigen was predicted to be absent (−).

FIGS. 10A-C. Definitive HPC pathway. FIG. 10A. Schematic representation beginning with ESCs or iPSCs and ending with HPCs. Both hematopoietic programs, Primitive (top) and Definitive (bottom), transition through intermediates, developing from KDR+ CD34-CD144-progenitors that are distinguished by CD235a expression. The generation of primitive progenitors (KDR+CD235a+) depends on stage-specific Activin/nodal signaling and inhibition of the Wnt/β-catenin pathway, vs specification of definitive progenitors (KDR+ CD235a−) requires Wnt/β-catenin signaling during the same timeframe and co-culture with Notch ligand expressing stroma. FIG. 10B. Morphology and relative size of the erythroid colonies (top) and terminally differentiated RBCs derived from these colonies (bottom). Gray arrows indicate small, primitive (Prim-RBC) colonies. Original magnification: colonies, X100; cells, X1000. FIG. 10C. Globin analysis was performed on red cell colonies from Prim-HPCs, definitive (Def)-HPCs, fetal liver HPCs (FL), and bone marrow HPCs (BM) by QRT-PCR. In the graph, "epsilon" is represented by the left bar, "gamma" is represented by the middle bar, and "beta" is represented by the right bar, for each set of three bars.

FIGS. 11A-B. IFC analysis of hESC derived RBC maturation. FIG. 11A. Maturational series of ESC cells matured towards definitive RBCs as described in FIGS. 10A-C. Definitive HPCs were grown in liquid culture for 12 days in RBC maturation media and analyzed based on cell size and nuclear size (Left). Bright field (BF), CD235, CD71, and DNA channels are shown for cells indicated on left panel (Right). FIG. 11B. The cultures were analyzed for RNA at the single cell level using RNA flow (Primeflow, Ebioscience) for epsilon and gamma globin. As expected, all cells are gamma positive, but a subset of ESC-derived definitive cultures are epsilon globin-positive while human fetal liver-derived RBCs are negative.

FIG. 13A-D. Dox-regulated suppression of Gata1 generates self-renewing MEPs. FIG. 13A. Modified ESCs were differentiated with dox, TPO and SCF. Cumulative cell number vs. time (n=4 experiments). FIG. 13B. FACS analysis of Kit and CD41 expression. FIG. 13C. RT-PCR quantification of Gata1 mRNA after dox withdrawal. (n=3 expts)*, p<0.05. Mean±S.E.M. FIG. 13D. Western blotting for GATA1 protein after dox removal.

FIG. 14. G1ME2 cell colonies. Cells ($10^4$) were plated into methycellulose colony forming assays with EPO, SCF, TPO, IL-3, and M-CSF, in the absence of dox. Erythroid (Ery), mixed erythroidmegakaryocyte (E-meg), and megakaryocyte (Meg) colonies were enumerated.

FIG. 16A. Two components of Tet-on vector system (CAG-rtTA and TRE-GFP) were introduced into separate alleles of the AAVS1 locus in H9 ESCs using zinc finger-mediated homologous recombination. Gene X is induced by dox. FIG. 16B. Hematopoietic progenitors produced from the modified H9 ESCs were treated with dox for 0, 2 and 4 days, and assayed for GFP expression.

FIG. 17. Dox inducible GATA1 shRNAs in K562 cells. Western blot of K562 cells stably transfected with 3 GATA1 shRNAs in the lenti-X Tet-on system (Clontech)±dox as indicated.

FIGS. 18A-C. Generation of RHD constructs for donor DNA vector. (FIG. 18A) Schematic of first two exons of RHCE in a Rh null iPSC and location of guide RNA in intron 1 designed for CRISPR-mediated gene editing and the DNA constructed by inventors to insert by homologous recombination. (FIG. 18B) Detailed schematic of insert created with RHD cDNA (exons 2-10 of any given variant), arms of homology, PGK promoter, puromycin resistance cassette and LoxP sites. (FIG. 18C) Donor DNA vector with RHD exons 2-10 that allows simple replacement by variant RHD or RHCE cDNA using restriction enzymes to generate iPSCs with variant RH (at site of red arrow). gRNA, guide RNA; SA, splice acceptor; Puro, puromycin resistance cassette; Prom, promoter; pA poly A.

FIGS. 19A-B. Generation of Rh null induced pluripotent stem cells (iPSCs). (FIG. 19A) Schematic of first two exons of RHD and RHCE and location of guide RNA designed for CRISPR-mediated gene editing to disrupt Rh protein expression. (FIG. 19B) Flow cytometry of cell surface Rh expression on red blood cells (RBCs) from donor derived RBCs (left), the untargeted Rh+ parent iPSCs (middle), and the targeted Rh null iPSCs (right) showing no Rh expression on the RBCs from targeted Rh null iPSCs.

FIG. 20. Culture conditions for iPSC differentiation into hematopoietic progenitors and subsequent erythroid differentiation. iPSCs are differentiated via an embryoid body culture with the cytokines bone morphogenic protein 4 (BMP4), vascular endothelial growth factor (VEGF), stem cell factor (SCF), thrombopoietin (TPO), Flt3 ligand (FLT3), and fibroblast growth factor (FGF). Hematopoietic progenitors are harvested and cultured in liquid erythroid cultures supported by erythropoietin (EPO), SCF, and holotransferrin.

FIGS. 21A-B. Antibody screening with induced pluripotent stem cell derived red blood cells (iRBCs). (FIG. 21A) Patient serum containing anti-e was reacted with donor derived panel red cells or iRBCs in the gel card assay and showed agglutination with all e+ cells and no agglutination with all e− cells, consistent with anti-e antibody present. (FIG. 21B) Patient serum containing anti-hrS was reacted with donor derived panel red cells or iRBCs in the gel card assay and showed agglutination with all hrS+ cells and no agglutination with all hrS− cells.

FIG. 23A. Schematic representation of a combination of amplification methods showing that yield of cRBCs can be increased by sequential expansion of the stem progenitor and erythroid precursor compartment by sequential use of HSC-expansion, HPC-expansion, and erythroblast expansion media.

FIG. 23B. Representative diagram of the composition of the HSC-expansion, E-expansion, and E-differentiation media used in the Olivier cRBCs production protocol.

FIG. 23C. Representative table illustrating the yield (mean+/−SD) of cRBCs obtained with (L1) or without (O1) a HSC-expansion step and with a 48-hour pulse in E-expansion prior to culture in HSC-expansion conditions (O2).

FIG. 23D. Representative histogram illustrating the large increase in yield observed in condition O2 as compare to conditions O1 and L1.

FIG. 23E. Representative scatterplots illustrating the number of cells when hESC-derived, CB or PB CD34$^+$ cells are cultured in conditions L1, O1, or O2.

FIG. 23F. Representative histograms illustrating the number of cRBCs obtained after incubation of CB CD34$^+$ cells in L1 or O2 conditions for a total of 21 days or in O2×3 for a total of 35 days. The L1, O2, and O2×3 conditions are symbolically represented by pink, green, and red boxes, respectively, in the histogram. The colors of the boxes correspond to the media composition (FIG. 23B). The size of the boxes is proportional to the length of incubation.

FIG. 23G. Erythroblast expansion. Representative dotplot illustrating fold-increase in cell number observed when hESC-derived CD34$^+$ cells are grown in SED conditions (left panel). Weekly fold-increases in cell number were observed when hESC-derived CD34$^+$ cells were grown in SED conditions, reached a peak at day 23, and stabilized at about 2-fold per week (right panel). The composition of the erythroblast expansion (SED) medium is shown in the bottom of the panel.

DETAILED DESCRIPTION

Figure 2:
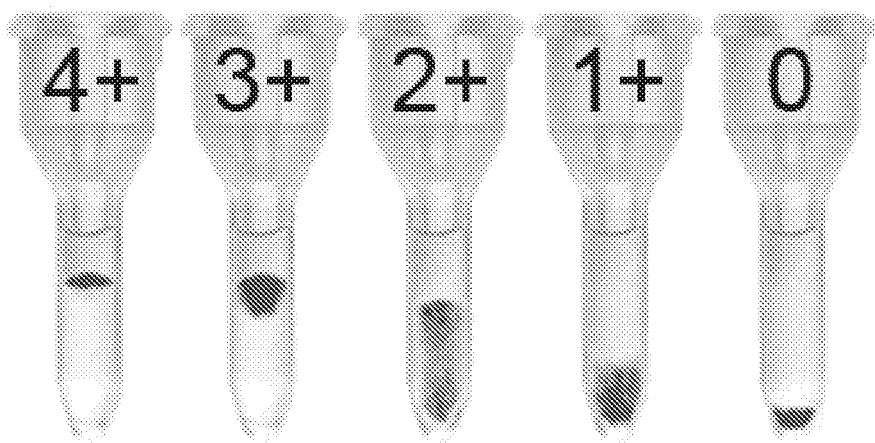
FIG. 2. RBC agglutination grading. Agglutination occurs when antibody present reacts against an RBC antigen, and is graded 0 to 4+. The gel assay depicted shows agglutinated RBCs retained in the column matrix, and free nonagglutinated cells pellet at the bottom.

As discuss above, transfusion therapies are commonly used to treat a wide variety of diseases. Some of these, like Sickle Cell Disease, require repeated transfusions over the lifetime of the patient. As such, the introduction of heterologous blood antigens can result in the development of immune responses to red blood cells in the transfused blood. This is particularly problematic when considering the presence of rare blood antigens that are more likely to be viewed as "foreign" by any given transfusion recipient. The ability to assess the presence of antibodies to blood antigens, including rare blood antigens, in chronic transfusion recipients, is therefore critical to long-term managed care.

Incompatible transfusions can occur when antibody specificities are not accurately identified. It is therefore imperative that all antibodies present in a patient's serum are identified prior to each transfusion. Due to genetic differences, patients with sickle cell disease (SCD) often experience Rh incompatibilities that do not cause problems in the general population. These cases often require sample referral to specialized reference laboratories, which significantly delays patient care and increases costs. Testing at reference laboratories consumes resources, both in reagents and highly skilled labor, and often times, the fine specificity and clinical significance of antibodies cannot be identified. Without wishing to be bound by theory, the present inventors discovered "universal reagent red blood cells" that enable rapid, cost-saving, and reliable antibody identification in the hospital laboratory to guide transfusion therapy for highly allo-immunized patient populations including those needing chronic transfusion, patients with sickle cell disease, who are mainly of African ancestry, patients with thalassemia who are primarily of Asian ancestry, and patients receiving cancer immunotherapy drugs which interfere with testing for blood transfusion.

In particular, the availability of red blood cells (RBCs) lacking high prevalence antigens such as Rh null lines, or expressing Rh variants not found in natural combinations are particularly relevant because current donor-derived RBC reagents cannot resolve these complex antibody specificities. These reagent red blood cells described herein enable the rapid identification of compatible blood donors, and also provide starting material for large-scale reagent cultured rare red blood cells for transfusion. These studies are innovative in that they provide clinical grade reagents needed to test for transfusion compatibility that currently do not exist, and they provide an opportunity to produce reagent cultured red blood cells for transfusion. Using a number of different genome-editing techniques in induced pluripotent stem cells (iPSCs) to inactivate blood group genes that encode high prevalence RBC antigens, or to introduce constructs to express variant or altered Rh antigens, will eliminate the need for complex work-ups and have the potential to streamline and standardize antibody identification testing particularly for, but not limited to, the ~100,000 patients with SCD in the US. Importantly, several of the customized iPSC lines would be life-saving "universal" donors for patients sensitized to numerous blood group antigens who are not able to be transfused with standard blood transfusion, and serve a currently unmet clinical need.

More than 15 million RBC transfusions are performed each year in the U.S. making RBC transfusions one of the most important medical therapies available. SCD is the most prevalent monogenic disorder in the world and affects over 100,000 people in the United States. SCD affects 1/625 minorities and 8% carry the Hb S mutation termed sickle-cell trait.

RBC transfusion is a primary treatment for patients with SCD and thalassemia major but development of antibodies directed against foreign donor RBCs (allo-immunization) is a significant complication that affects 35% and, in some studies, as high as 65% of chronically transfused patients, compared to 2-3% in the general population (Rosse et al., *Blood* 76: 1431-1437, 1990; and Thompson et al., *Br. J. Haematol.* 153: 121-128, 2011). RBC antigen differences between African American patients and blood donors, who are primarily European American, contribute to the incidence of allo-immunization, as does the large number of transfusions. A further complication is that patients who develop one antibody are at significantly increased risk for multiple antibodies because of as-yet unknown factors and stimulation of the immune system. Approximately 50% of patients who make antibodies to foreign RBCs also have auto-antibodies (cross-reactive with their own RBCs) in the serum (data not shown) (Shirey et al., *Transfusion* 42:1435-1441, 2002).

Distinguishing allo- from auto-antibodies is clinically important for transfusion but is difficult for routine blood bank laboratories and often requires referral to a high complexity reference laboratory. Complex multiple adsorptions of the serum with known RBCs, followed by retesting of the serum and elution of the antibodies is often required. These procedures consume vast resources and are laborious, both in reagents and highly skilled technical labor. Allo-immunization often causes delays in treatment. In some cases, patients with complex and multiple antibody specificities are taken off life-benefiting transfusion protocols due to difficulty in finding compatible RBCs negative for multiple antigens, or who require matching for high prevalence antigens and rare blood types.

Proper matching of patients and blood products is essential because transfusion of incompatible blood or blood products can lead to an immune reaction with hemolysis of the transfused RBCs, and, depending on the severely of the reaction, lead to pain, fever, anemia, acute kidney failure, and/or shock. Delayed transfusion reactions, which occur when sensitized patients produce antibodies following a secondary immune reaction, are associated with RBC destruction, anemia, and jaundice. Some patients experience life-threatening hyper-hemolysis syndrome, a poorly understood phenomena that includes acute lysis of the transfused cells as well as the patient's own cells termed "bystander" hemolysis (Talano et al., *Pediatrics* 111: e661-665, 2003).

Without wishing to be bound by theory, the present inventors are able to produce reagent red blood cells with rare or uncommon blood group antigen combinations and also cRBCs that lack high prevalence antigens (found on all but rare donor RBCs and determined by blood group genotyping). This will address a critical issue in transfusion therapy by providing a standardized and rapid means of distinguishing complex allo-antibody specificities from auto-antibodies in the patient's serum. The production of rare reagent RBCs will provide an important resource not currently available to hospital blood banks, and some reference immunohematology laboratories, as the lack of reagent RBCs for rapid identification of the antibody specificity leads to significant delays in determining which donors would be compatible and compromises transfusion safety.

It is estimated that about $10^{13}$ cells would be sufficient to cover annual needs for reagent cells lacking high prevalence antigens, and that reference laboratory testing costs would be decreased by at least 70% by replacing the labor-intensive auto- and allo-adsorptions that often yield ambiguous results.

There are more than 300 blood group antigens, defined by protein and carbohydrate polymorphisms on the RBC, reflecting the diversity of people from different ethnic populations. For most transfusion therapies, matching the patient with the donor for the ABO and RhD blood groups is sufficient to avoid eliciting an immune reaction. However, transfusion therapy becomes more complex in chronically transfused patients who often produce antibodies against foreign red cell antigens. The causes of the high incidence of allo-immunization in chronically transfused patients include the large number of donor RBC exposures, ethnic blood group differences, and possibly chronic inflammation.

Despite attempts to preventively match patients and donors for additional blood groups (C, E, and K), the incidence of allo-immunization in chronically transfused patients remains high. Paradoxically, allo-immunized individuals can have RBCs that type positive for an antigen, but also have the corresponding antibody in the serum. This defies a principal dogma in transfusion medicine, which is that a patient whose RBCs type positive for an antigen is not at risk of producing an antibody to that antigen. This most often occurs in the Rh system with D, C, and e antigens. A major cause of this paradox is that many patients with SCD have inherited altered RH alleles, which leads to the recognition of conventional Rh proteins as foreign. In approximately ⅓ of these cases, the presence of these antibodies was associated with significant destruction of the transfused RBCs (Chou et al., *Blood* 122: 1062-1071, 2013). Other antibodies that are often found in the serum of patients with SCD include anti-U, anti-hrS, and anti-hrB, but these are heterogeneous specificities and often are not compatible within each group. RH genotyping can accurately classify the fine specificity and is key to finding compatible donors. Approximately 2% ($U^-$) to 4% ($hrS^-$ and $hrB^-$) of African-Americans lack these antigens on their RBCs, and are therefore at risk of making allo-antibodies. These allo-antibodies, which are clinically significant, cannot be distinguished from auto-antibodies in traditional testing, as they react with all red cells provided with current commercial panels.

The present disclosure reports on the development of a panel of modified red blood cells that engineered for use in testing the blood of transfusion patients for antibodies against rare blood antigens. These and other aspects of the disclosure are described in detail below.

I. BLOOD GROUPS AND ENGINEERED BLOOD CELLS

A. Blood Groups

The term human blood group systems is defined by International Society of Blood Transfusion as systems in the human species where cell-surface antigens—in particular, those on blood cells—are "controlled at a single gene locus or by two or more very closely linked homologous genes with little or no observable recombination between them," and include the common ABO and Rh-(Rhesus) antigen systems, as well as many others; thirty-six major human systems are identified as of February 2018. In addition to the ABO and Rh systems, the antigens expressed on blood cell membrane surfaces include 346 red blood cell antigens and 33 platelet antigens, as defined serologically. The genetic basis for most of these antigens lie in 45 red blood cell and 6 platelet genes. An individual, for example, can be AB RhD positive, and at the same time M and N positive in the MNS system, K positive in the Kell system, and Le$^a$ or Le$^b$ positive in the Lewis system, where these and many of the systems are named for patients in whom the corresponding antibodies were first detected.

Blood is composed of cells suspended in a liquid called plasma. Suspended in the plasma are three types of cells: Red blood cells that carry oxygen; White blood cells that fight infection; and Platelets that stop bleeding in injuries. The most common type of grouping is the ABO (either uppercase or lowercase) grouping. The varieties of glycoprotein coating on red blood cells divides blood into four groups: A (A oligosaccharide is present); B (B oligosaccharide is present); AB (A and B oligosaccharides are present); and O (neither A nor B, only their precursor H oligosaccharide present). There are subtypes under this grouping (listed as A1, A2, A1B or A2B . . . ) some of which are quite rare. Apart from this there is a protein which plays an important part in the grouping of blood. This is called the Rh factor. If this is present, the particular blood type is called positive. If it is absent, it is called negative. Thus, there are the following broad categories:

A1 Negative (A1 moni –ve)
A1 Positive (A1 +ve)
A1B Negative (A1B –ve)
A1B Positive (A1B +ve)
A2 Negative (A2 –ve)
A2 Positive (A2 +ve)
A2B Negative (A2B –ve)
A2B Positive (A2B +ve)
B Negative (B –ve)
B Positive (B +ve)
B1 Positive (B1 +ve)
O Negative (O –ve)
O Positive (O +ve)

In the "ABO" system, (and Rhesus D system) all blood belongs to one of four major groups: A±, B±, AB±, or O±. The presence (+) or absence (–) of the RhD (Rhesus D) antigen is indicated by the plus or minus following the ABO type. But there are more than two hundred minor blood groups that can complicate blood transfusions. Many of these are known as rare blood types. Whereas common blood types are expressed in a letter or two, which may be a plus or a minus, a smaller number of people express their blood type in an extensive series of letters in addition to their "AB–" type designation. For example, the h/h blood group, also known as Oh or the Bombay blood group, is a rare blood type.

B. Engineered Blood Cells

Provided herein are methods of making reagent or recombinant red blood cell (e.g., a first reagent red blood cell, a second reagent red blood cell, or any of the other reagent red blood cells described herein) that is characterized by the presence of one or more cell surface antigens (e.g., one or more blood group antigens (e.g., any of the blood group antigens described herein or known in the art)) on its surface. In some embodiments, a reagent red blood cell (e.g., a second reagent red blood cell) or a recombinant red blood cell can lack at least one cell surface antigen (e.g., one or more blood group antigens) that is otherwise present on a naturally-occurring red blood cell or another reagent red blood cell (e.g., a first reagent red blood cell).

Induced pluripotent stem cells (iPSCs) are a permanent source of cells that can theoretically be used to produce an unlimited number of reagent or recombinant RBCs. Methods of generating a RBC from an iPSC cell are known in the art, and can be used herein (see, e.g., Example 2). For example, a genetic modification (e.g., gene editing to remove or mutate a gene that encodes an antigen) can be performed on a precursor cell (e.g., iPSCs) and the iPSCs differentiated or cultured to yield reagent red blood cells (e.g., any of the reagent red blood cells described herein). Non-limiting methods for performing gene editing to remove or mutate a gene that encodes an antigen are described herein. Additional methods for performing gene editing to remove or mutate a gene that encodes an antigen are known in the art (e.g., site-specific recombination).

Some embodiments of these methods can include introducing a nucleic acid that encodes an antigen (e.g., a blood group antigen) into a red blood cell (e.g., a reagent red blood cell) or into a precursor cell (e.g., iPSCs) that is cultured or differentiated into a reagent red blood cell. Exemplary methods for introducing a nucleic acid that encodes an antigen into a cell are described herein. Additional methods for introducing a nucleic acid that encodes an antigen into a cell are known in the art.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth. Additional exemplary methods for generating a reagent red blood cell are described below.

Non-limiting examples of reagent red blood cells that can be produced by the methods described herein are listed in Table 1.4 below.

TABLE 1.4

Exemplary Panel of Reagent Cultured Red Blood Cells

| | Relevant Genotype | RBC phenotype | Antibody detection |
|---|---|---|---|
| Rh null | No RHD, inactive RHCE | D–, C–, E–, c–, e– (no Rh antigens) | Identify antibodies against any high prevalence antigens in Rh system |
| D–– | Inactive RHCE | D+, C–, E–, c–, e– (no RhCE antigens) | Identify antibodies to RHCE |
| U–S–s– | Inactive GYB | D–, U–, S–, s– | Identify antibodies against high prevalence U antigen, and against S/s antigens |

TABLE 1.4-continued

Exemplary Panel of Reagent Cultured Red Blood Cells

| | Relevant Genotype | RBC phenotype | Antibody detection |
|---|---|---|---|
| hrB−, VS+ | RHCE*ce(733G) | D−, hrB−, VS+ | Identify antibodies against high prevalence hrB antigen (−) reaction), or to low prevalence VS antigen ((+) reaction) |
| hrB−, hrS− | RHCE*ce(48C, 667T) | D−, hrB−, hrS− | Identify specificity antibodies against high prevalence RHCE (hrB vs hrS) antigens ((−) reaction) |
| Rh null Go(a)+ | RHD*DIVa on Rh-nullbackground | D+, C−, E−, c−, e− Go(a)+ | Identify antibodies to this antigen which is unique to African Americans |
| Rh-null DAK+ | RHD*DIIIa on Rh-null background | D+, C−, E−, c−, e− DAK+ | Identify antibodies to this antigen which is unique to African Americans |
| Do null | Inactive ART | D−, Doa−, Dob− | Identify antibodies against high prevalence Do and HY antigens. Most useful as a future transfusion product. |
| Lua−b− | EKLF or LU inactive | | For testing patients on anti-CD38 therapy |
| CD47 null | CD47 null | | For testing patients on anti-CD47 therapy |

In some examples, the reagent red blood cells provided herein have a surface phenotype that does not naturally occur in a human or other mammal. In some embodiments, reagent red blood cells that are characterized, at least in part, by a D−, C−, E−, c−, e− surface phenotype are not naturally-occurring in a human or other mammal. In some embodiments, reagent red blood cells that are characterized, at least in part, by a D+, C−, E−, c−, e− surface phenotype are not naturally-occurring in a human or other mammal. In some embodiments, reagent red blood cells that are characterized, at least in part, by a D+, C−, E−, c−, e−, Go(a)+ surface phenotype are not naturally-occurring in a human or other mammal. In some embodiments, reagent red blood cells that are characterized, at least in part, by a D+, C−, E−, c−, e−, DAK+ surface phenotype are not naturally-occurring in a human or other mammal. In some embodiments, reagent red blood cells that are characterized, at least in part, by a D−, Doa−, Dob− surface phenotype are not naturally-occurring in a human or other mammal. In some embodiments, reagent red blood cells that are characterized, at least in part, by a CD47− surface phenotype are not naturally-occurring in a human or other mammal.

In some embodiments, a reagent red blood cell that is characterized, at least in part, by the absence of a C antigen, an E antigen, a c antigen, an e antigen, a U antigen, a S antigen, a s antigen, a hrB antigen, a Lua antigen, a Lub antigen, and a CD47 antigen on its surface are not naturally-occurring in a human or other mammal.

In some embodiments, reagent red blood cells that are characterized, at least in part, by a D−, U−, S−, s− surface phenotype, which is present in less than 1% (e.g., less than 0.5%, less than 0.2%, less than 0.1%, or less than 0.05%) of patients. In some embodiments, reagent red blood cells that are characterized, at least in part, by a D−, hrB−, VS+ phenotype, which is present in less than 1% (e.g., less than 0.5%, less than 0.2%, less than 0.1%, or less than 0.05%) of patients. In some embodiments, reagent red blood cells that are characterized, at least in part, by a Lua−, b− phenotype, which is present in less than 1% (e.g., less than 0.5%, less than 0.2%, less than 0.1%, or less than 0.05%) of patients.

Additional embodiments of exemplary reagent red blood cells provided herein can have a surface phenotype characterized, at least in part, by one of the following, or a combination of two or more of any of the following:

(i) D−, C−, E−, c−, e−;
(ii) D+, C−, E−, c−, e−;
(iii) D−, U−, S−, s−;
(iv) D−, hrB−, VS+;
(v) D−, hrB−, hrS−;
(vi) C−, E−, c−, e−;
(vii) D+, C−, E−, c−, e−, Go(a)+;
(viii) D+, C−, E−, c−, e−, DAK+;
(ix) D−, Doa−, Dob−;
(x) Lua− b−; and
(xi) CD47−.

For example, a reagent red blood can have a surface phenotype characterized by D−, C−, E−, c−, e−, Doa− and Dob−. In some instances, a reagent red blood can have a surface phenotype characterized by D−, C−, E−, c−, e−, Lua− and b−. The specific examples of reagent red blood cells described herein are exemplary. As can be appreciated, many additional reagent red blood cells having different surface phenotypes can be generated using the methods described herein. For example, any of the compositions, kits, and methods described herein can include or include the use of at least 2 (e.g., at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, or at least 200) different reagent red blood cells (e.g., any of the exemplary reagent red blood cells described herein, including, e.g., the first reagent red blood cell and the second reagent red blood cell), wherein each of the reagent red blood cells had a different surface phenotype from any of the other reagent red blood cells. For example, any of the compositions, kits, and methods described herein can include or include the use of 2 to about 200 (e.g., 2 to about 195, 2 to about 190, 2 to about 185, 2 to about 180, 2 to about 175, 2 to about 170, 2 to about 165, 2 to about 160, 2 to about 155, 2 to about 150, 2 to about 145, 2 to about 140, 2 to about 135, 2 to about 130, 2 to about 125, 2 to about 120, 2 to about 115, 2 to about 110, 2 to about 105, 2 to about 100, 2 to about 95, 2 to about 90, 2 to about 85, 2 to about 80, 2 to about 75, 2 to about 70, 2 to about 65, 2 to about 60, 2 to about 55, 2 to about 50, 2 to about 45, 2 to about 40, 2 to about 35, 2 to about 30, 2 to about 25, 2 to about 20, 2 to about 18, 2 to about 16, 2 to about 14, 2 to about 12, 2 to about 10, 2 to about 8, 2 to about 6, 2 to about 5, about 3 to about 200, about 3 to about 195, about 3 to about 190, about 3 to about 185, about 3 to about 180, about 3 to about 175, about 3 to about 170, about 3 to about 165, about 3 to about 160, about 3 to about 155, about 3 to about 150, about 3 to about 145, about 3 to about 140, about 3 to about 135, about 3 to about 130, about 3 to about 125, about 3 to about 120, about 3 to about 115, about 3 to about 110, about 3 to about 105, about 3 to about 100, about 3 to about 95, about 3 to about 90, about 3 to about 85, about 3 to about 80, about 3 to about 75, about 3 to about 70, about 3 to about 65, about 3 to about 60, about 3 to about 55, about 3 to about 50, about 3 to about 45, about 3 to about 40, about 3 to about 35, about 3 to about 30, about 3 to about 25, about 3 to about 20, about 3 to about 18, about 3 to about 16, about 3 to about 14, about 3 to about 12, about 3 to about 10, about 3 to about 8, about 3 to about 6, about 3 to about 5, about 4 to about 200, about 4 to about 195, about 4 to about 190, about 4 to about 185, about 4 to about 180, about 4 to about 175, about 4 to about 170, about 4 to about 165, about 4 to about 160, about 4 to about 155, about 4 to about 150, about 4 to about 145, about 4 to about 140, about 4 to about 135, about 4 to about 130, about 4 to about 125, about 4 to about 120, about 4 to about 115, about 4 to about 110, about 4 to about 105, about 4 to about 100, about 4 to about 95, about 4 to about 90, about 4 to about 85, about 4 to about 80, about 4 to about 75, about 4 to about 70, about 4 to about 65, about 4 to about 60, about 4 to about 55, about 4 to about 50, about 4 to about 45, about 4 to about 40, about 4 to about 35, about 4 to about 30, about 4 to about 25, about 4 to about 20, about 4 to about 18, about 4 to about 16, about 4 to about 14, about 4 to about 12, about 4 to about 10, about 4 to about 8, about 4 to about 6, about 5 to about 200, about 5 to about 195, about 5 to about 190, about 5 to about 185, about 5 to about 180, about 5 to about 175, about 5 to about 170, about 5 to about 165, about 5 to about 160, about 5 to about 155, about 5 to about 150, about 5 to about 145, about 5 to about 140, about 5 to about 135, about 5 to about 130, about 5 to about 125, about 5 to about 120, about 5 to about 115, about 5 to about 110, about 5 to about 105, about 5 to about 100, about 5 to about 95, about 5 to about 90, about 5 to about 85, about 5 to about 80, about 5 to about 75, about 5 to about 70, about 5 to about 65, about 5 to about 60, about 5 to about 55, about 5 to about 50, about 5 to about 45, about 5 to about 40, about 5 to about 35, about 5 to about 30, about 5 to about 25, about 5 to about 20, about 5 to about 18, about 5 to about 16, about 5 to about 14, about 5 to about 12, about 5 to about 10, about 5 to about 8, about 6 to about 200, about 6 to about 195, about 6 to about 190, about 6 to about 185, about 6 to about 180, about 6 to about 175, about 6 to about 170, about 6 to about 165, about 6 to about 160, about 6 to about 155, about 6 to about 150, about 6 to about 145, about 6 to about 140, about 6 to about 135, about 6 to about 130, about 6 to about 125, about 6 to about 120, about 6 to about 115, about 6 to about 110, about 6 to about 105, about 6 to about 100, about 6 to about 95, about 6 to about 90, about 6 to about 85, about 6 to about 80, about 6 to about 75, about 6 to about 70, about 6 to about 65, about 6 to about 60, about 6 to about 55, about 6 to about 50, about 6 to about 45, about 6 to about 40, about 6 to about 35, about 6 to about 30, about 6 to about 25, about 6 to about 20, about 6 to about 18, about 6 to about 16, about 6 to about 14, about 6 to about 12, about 6 to about 10, about 6 to about 8, about 8 to about 200, about 8 to about 195, about 8 to about 190, about 8 to about 185, about 8 to about 180, about 8 to about 175, about 8 to about 170, about 8 to about 165, about 8 to about 160, about 8 to about 155, about 8 to about 150, about 8 to about 145, about 8 to about 140, about 8 to about 135, about 8 to about 130, about 8 to about 125, about 8 to about 120, about 8 to about 115, about 8 to about 110, about 8 to about 105, about 8 to about 100, about 8 to about 95, about 8 to about 90, about 8 to about 85, about 8 to about 80, about 8 to about 75, about 8 to about 70, about 8 to about 65, about 8 to about 60, about 8 to about 55, about 8 to about 50, about 8 to about 45, about 8 to about 40, about 8 to about 35, about 8 to about 30, about 8 to about 25, about 8 to about 20, about 8 to about 18, about 8 to about 16, about 8 to about 14, about 8 to about 12, about 8 to about 10, about 10 to about 200, about 10 to about 195, about 10 to about 190, about 10 to about 185, about 10 to about 180, about 10 to about 175, about 10 to about 170, about 10 to about 165, about 10 to about 160, about 10 to about 155, about 10 to about 150, about 10 to about 145, about 10 to about 140, about 10 to about 135, about 10 to about 130, about 10 to about 125, about 10 to about 120, about 10 to about 115, about 10 to about 110, about 10 to about 105, about 10 to about 100, about 10 to about 95, about 10 to about 90, about 10 to about 85, about 10 to about 80, about 10 to about 75, about 10 to about 70, about 10 to about 65, about 10 to about 60, about 10 to about 55, about 10 to about 50, about 10 to about 45, about 10 to about 40, about 10 to about 35, about 10 to about 30, about 10 to about 25, about 10 to about 20, about 10 to about 18, about 10 to about 16, about 10 to about 14, about 10 to about 12, about 12 to about 200, about 12 to about 195, about 12 to about 190, about 12 to about 185, about 12 to about 180, about 12 to about 175, about 12 to about 170, about 12 to about 165, about 12 to about 160, about 12 to about 155, about 12 to about 150, about 12 to about 145, about 12 to about 140, about 12 to about 135, about 12 to about 130, about 12 to about 125, about 12 to about 120, about 12 to about 115, about 12 to about 110, about 12 to about 105, about 12 to about 100, about 12 to about 95, about 12 to about 90, about 12 to about 85, about 12 to about 80, about 12 to about 75, about 12 to about 70, about 12 to about 65, about 12 to about 60, about 12 to about 55, about 12 to about 50, about 12 to about 45, about 12 to about 40, about 12 to about 35, about 12 to about 30, about 12 to about 25, about 12 to about 20, about 12 to about 18, about 12 to about 16, about 12 to about 14, about 14 to about 200, about 14 to about 195, about 14 to about 190, about 14 to about 185, about 14 to about 180, about 14 to about 175, about 14 to about 170, about 14 to about 165, about 14 to about 160, about 14 to about 155, about 14 to about 150, about 14 to about 145, about 14 to about 140, about 14 to about 135, about 14 to about 130, about 14 to about 125, about 14 to about 120, about 14 to about 115, about 14 to about 110, about 14 to about 105, about 14 to about 100, about 14 to about 95, about 14 to about 90, about 14 to about 85, about 14 to about 80, about 14 to about 75, about 14 to about 70, about 14 to about 65, about 14 to about 60, about 14 to about 55, about 14 to about 50, about 14 to about 45, about 14 to about 40, about 14 to about 35, about 14 to about 30, about 14 to about 25, about 14 to about 20, about 14 to about 18, about 14 to about 16, about 16 to about 200, about 16 to about 195, about 16 to about 190, about 16 to about 185, about 16 to about 180, about 16 to about 175, about 16 to about 170, about 16 to about 165, about 16 to about 160, about 16 to about 155, about 16 to about 150, about 16 to about 145, about 16 to about 140, about 16 to about 135, about 16 to about 130, about 16 to about 125, about 16 to about 120, about 16 to about 115, about 16 to about 110, about 16 to about 105, about 16 to about 100, about 16 to about 95, about 16 to about 90, about 16 to about 85, about 16 to about 80, about 16 to about 75, about 16 to about 70, about 16 to about 65, about 16 to about 60, about 16 to about 55, about 16 to about 50, about 16 to about 45, about 16 to about 40, about 16 to about 35, about 16 to about 30, about 16 to about 25, about 16 to about 20, about 16 to about 18, about 18 to about 200, about 18 to about 195, about 18 to about 190, about 18 to about 185, about 18 to about 180, about 18 to about 175, about 18 to about 170, about 18 to about 165, about 18 to about 160, about 18 to about 155, about 18 to about 150, about 18 to about 145, about 18 to about 140, about 18 to about 135, about 18 to about 130, about 18 to about 125, about 18 to about 120, about 18 to about 115, about 18 to about 110, about 18 to about 105, about 18 to about 100, about 18 to about 95, about 18 to about 90, about 18 to about 85, about 18 to about 80, about 18 to about 75, about 18 to about 70, about 18 to about 65, about 18 to about 60, about 18 to about 55, about 18 to about 50, about 18 to about 45, about 18 to about 40, about 18 to about 35, about 18 to about 30, about 18 to about 25, about 18 to about 20, about 20 to about 200, about 20 to about 195, about 20 to about 190, about 20 to about 185, about 20 to about 180, about 20 to about 175, about 20 to about 170, about 20 to about 165, about 20 to about 160, about 20 to about 155, about 20 to about 150, about 20 to about 145, about 20 to about 140, about 20 to about 135, about 20 to about 130, about 20 to about 125, about 20 to about 120, about 20 to about 115, about 20 to about 110, about 20 to about 105, about 20 to about 100, about 20 to about 95, about 20 to about 90, about 20 to about 85, about 20 to about 80, about 20 to about 75, about 20 to about 70, about 20 to about 65, about 20 to about 60, about 20 to about 55, about 20 to about 50, about 20 to about 45, about 20 to about 40, about 20 to about 35, about 20 to about 30, about 20 to about 25, about 25 to about 200, about 25 to about 195, about 25 to about 190, about 25 to about 185, about 25 to about 180, about 25 to about 175, about 25 to about 170, about 25 to about 165, about 25 to about 160, about 25 to about 155, about 25 to about 150, about 25 to about 145, about 25 to about 140, about 25 to about 135, about 25 to about 130, about 25 to about 125, about 25 to about 120, about 25 to about 115, about 25 to about 110, about 25 to about 105, about 25 to about 100, about 25 to about 95, about 25 to about 90, about 25 to about 85, about 25 to about 80, about 25 to about 75, about 25 to about 70, about 25 to about 65, about 25 to about 60, about 25 to about 55, about 25 to about 50, about 25 to about 45, about 25 to about 40, about 25 to about 35, about 25 to about 30, about 30 to about 200, about 30 to about 195, about 30 to about 190, about 30 to about 185, about 30 to about 180, about 30 to about 175, about 30 to about 170, about 30 to about 165, about 30 to about 160, about 30 to about 155, about 30 to about 150, about 30 to about 145, about 30 to about 140, about 30 to about 135, about 30 to about 130, about 30 to about 125, about 30 to about 120, about 30 to about 115, about 30 to about 110, about 30 to about 105, about 30 to about 100, about 30 to about 95, about 30 to about 90, about 30 to about 85, about 30 to about 80, about 30 to about 75, about 30 to about 70, about 30 to about 65, about 30 to about 60, about 30 to about 55, about 30 to about 50, about 30 to about 45, about 30 to about 40, about 30 to about 35, about 35 to about 200, about 35 to about 195, about 35 to about 190, about 35 to about 185, about 35 to about 180, about 35 to about 175, about 35 to about 170, about 35 to about 165, about 35 to about 160, about 35 to about 155, about 35 to about 150, about 35 to about 145, about 35 to about 140, about 35 to about 135, about 35 to about 130, about 35 to about 125, about 35 to about 120, about 35 to about 115, about 35 to about 110, about 35 to about 105, about 35 to about 100, about 35 to about 95, about 35 to about 90, about 35 to about 85, about 35 to about 80, about 35 to about 75, about 35 to about 70, about 35 to about 65, about 35 to about 60, about 35 to about 55, about 35 to about 50, about 35 to about 45, about 35 to about 40, about 40 to about 200, about 40 to about 195, about 40 to about 190, about 40 to about 185, about 40 to about 180, about 40 to about 175, about 40 to about 170, about 40 to about 165, about 40 to about 160, about 40 to about 155, about 40 to about 150, about 40 to about 145, about 40 to about 140, about 40 to about 135, about 40 to about 130, about 40 to about 125, about 40 to about 120, about 40 to about 115, about 40 to about 110, about 40 to about 105, about 40 to about 100, about 40 to about 95, about 40 to about 90, about 40 to about 85, about 40 to about 80, about 40 to about 75, about 40 to about 70, about 40 to about 65, about 40 to about 60, about 40 to about 55, about 40 to about 50, about 40 to about 45, about 45 to about 200, about 45 to about 195, about 45 to about 190, about 45 to about 185, about 45 to about 180, about 45 to about 175, about 45 to about 170, about 45 to about 165, about 45 to about 160, about 45 to about 155, about 45 to about 150, about 45 to about 145, about 45 to about 140, about 45 to about 135, about 45 to about 130, about 45 to about 125, about 45 to about 120, about 45 to about 115, about 45 to about 110, about 45 to about 105, about 45 to about 100, about 45 to about 95, about 45 to about 90, about 45 to about 85, about 45 to about 80, about 45 to about 75, about 45 to about 70, about 45 to about 65, about 45 to about 60, about 45 to about 55, about 45 to about 50, about 50 to about 200, about 50 to about 195, about 50 to about 190, about 50 to about 185, about 50 to about 180, about 50 to about 175, about 50 to about 170, about 50 to about 165, about 50 to about 160, about 50 to about 155, about 50 to about 150, about 50 to about 145, about 50 to about 140, about 50 to about 135, about 50 to about 130, about 50 to about 125, about 50 to about 120, about 50 to about 115, about 50 to about 110, about 50 to about 105, about 50 to about 100, about 50 to about 95, about 50 to about 90, about 50 to about 85, about 50 to about 80, about 50 to about 75, about 50 to about 70, about 50 to about 65, about 50 to about 60, about 50 to about 55, about 55 to about 200, about 55 to about 195, about 55 to about 190, about 55 to about 185, about 55 to about 180, about 55 to about 175, about 55 to about 170, about 55 to about 165, about 55 to about 160, about 55 to about 155, about 55 to about 150, about 55 to about 145, about 55 to about 140, about 55 to about 135, about 55 to about 130, about 55 to about 125, about 55 to about 120, about 55 to about 115, about 55 to about 110, about 55 to about 105, about 55 to about 100, about 55 to about 95, about 55 to about 90, about 55 to about 85, about 55 to about 80, about 55 to about 75, about 55 to about 70, about 55 to about 65, about 55 to about 60, about 60 to about 200, about 60 to about 195, about 60 to about 190, about 60 to about 185, about 60 to about 180, about 60 to about 175, about 60 to about 170, about 60 to about 165, about 60 to about 160, about 60 to about 155, about 60 to about 150, about 60 to about 145, about 60 to about 140, about 60 to about 135, about 60 to about 130, about 60 to about 125, about 60 to about 120, about 60 to about 115, about 60 to about 110, about 60 to about 105, about 60 to about 100, about 60 to about 95, about 60 to about 90, about 60 to about 85, about 60 to about 80, about 60 to about 75, about 60 to about 70, about 60 to about 65, about 65 to about 200, about 65 to about 195, about 65 to about 190, about 65 to about 185, about 65 to about 180, about 65 to about 175, about 65 to about 170, about 65 to about 165, about 65 to about 160, about 65 to about 155, about 65 to about 150, about 65 to about 145, about 65 to about 140, about 65 to about 135, about 65 to about 130, about 65 to about 125, about 65 to about 120, about 65 to about 115, about 65 to about 110, about 65 to about 105, about 65 to about 100, about 65 to about 95, about 65 to about 90, about 65 to about 85, about 65 to about 80, about 65 to about 75, about 65 to about 70, about 70 to about 200, about 70 to about 195, about 70 to about 190, about 70 to about 185, about 70 to about 180, about 70 to about 175, about 70 to about 170, about 70 to about 165, about 70 to about 160, about 70 to about 155, about 70 to about 150, about 70 to about 145, about 70 to about 140, about 70 to about 135, about 70 to about 130, about 70 to about 125, about 70 to about 120, about 70 to about 115, about 70 to about 110, about 70 to about 105, about 70 to about 100, about 70 to about 95, about 70 to about 90, about 70 to about 85, about 70 to about 80, about 70 to about 75, about 75 to about 200, about 75 to about 195, about 75 to about 190, about 75 to about 185, about 75 to about 180, about 75 to about 175, about 75 to about 170, about 75 to about 165, about 75 to about 160, about 75 to about 155, about 75 to about 150, about 75 to about 145, about 75 to about 140, about 75 to about 135, about 75 to about 130, about 75 to about 125, about 75 to about 120, about 75 to about 115, about 75 to about 110, about 75 to about 105, about 75 to about 100, about 75 to about 95, about 75 to about 90, about 75 to about 85, about 75 to about 80, about 80 to about 200, about 80 to about 195, about 80 to about 190, about 80 to about 185, about 80 to about 180, about 80 to about 175, about 80 to about 170, about 80 to about 165, about 80 to about 160, about 80 to about 155, about 80 to about 150, about 80 to about 145, about 80 to about 140, about 80 to about 135, about 80 to about 130, about 80 to about 125, about 80 to about 120, about 80 to about 115, about 80 to about 110, about 80 to about 105, about 80 to about 100, about 80 to about 95, about 80 to about 90, about 80 to about 85, about 85 to about 200, about 85 to about 195, about 85 to about 190, about 85 to about 185, about 85 to about 180, about 85 to about 175, about 85 to about 170, about 85 to about 165, about 85 to about 160, about 85 to about 155, about 85 to about 150, about 85 to about 145, about 85 to about 140, about 85 to about 135, about 85 to about 130, about 85 to about 125, about 85 to about 120, about 85 to about 115, about 85 to about 110, about 85 to about 105, about 85 to about 100, about 85 to about 95, about 85 to about 90, about 90 to about 200, about 90 to about 195, about 90 to about 190, about 90 to about 185, about 90 to about 180, about 90 to about 175, about 90 to about 170, about 90 to about 165, about 90 to about 160, about 90 to about 155, about 90 to about 150, about 90 to about 145, about 90 to about 140, about 90 to about 135, about 90 to about 130, about 90 to about 125, about 90 to about 120, about 90 to about 115, about 90 to about 110, about 90 to about 105, about 90 to about 100, about 90 to about 95, about 95 to about 200, about 95 to about 195, about 95 to about 190, about 95 to about 185, about 95 to about 180, about 95 to about 175, about 95 to about 170, about 95 to about 165, about 95 to about 160, about 95 to about 155, about 95 to about 150, about 95 to about 145, about 95 to about 140, about 95 to about 135, about 95 to about 130, about 95 to about 125, about 95 to about 120, about 95 to about 115, about 95 to about 110, about 95 to about 105, about 95 to about 100, about 100 to about 200, about 100 to about 195, about 100 to about 190, about 100 to about 185, about 100 to about 180, about 100 to about 175, about 100 to about 170, about 100 to about 165, about 100 to about 160, about 100 to about 155, about 100 to about 150, about 100 to about 145, about 100 to about 140, about 100 to about 135, about 100 to about 130, about 100 to about 125, about 100 to about 120, about 100 to about 115, about 100 to about 110, about 100 to about 105, about 105 to about 200, about 105 to about 195, about 105 to about 190, about 105 to about 185, about 105 to about 180, about 105 to about 175, about 105 to about 170, about 105 to about 165, about 105 to about 160, about 105 to about 155, about 105 to about 150, about 105 to about 145, about 105 to about 140, about 105 to about 135, about 105 to about 130, about 105 to about 125, about 105 to about 120, about 105 to about 115, about 105 to about 110, about 110 to about 200, about 110 to about 195, about 110 to about 190, about 110 to about 185, about 110 to about 180, about 110 to about 175, about 110 to about 170, about 110 to about 165, about 110 to about 160, about 110 to about 155, about 110 to about 150, about 110 to about 145, about 110 to about 140, about 110 to about 135, about 110 to about 130, about 110 to about 125, about 110 to about 120, about 110 to about 115, about 115 to about 200, about 115 to about 195, about 115 to about 190, about 115 to about 185, about 115 to about 180, about 115 to about 175, about 115 to about 170, about 115 to about 165, about 115 to about 160, about 115 to about 155, about 115 to about 150, about 115 to about 145, about 115 to about 140, about 115 to about 135, about 115 to about 130, about 115 to about 125, about 115 to about 120, about 120 to about 200, about 120 to about 195, about 120 to about 190, about 120 to about 185, about 120 to about 180, about 120 to about 175, about 120 to about 170, about 120 to about 165, about 120 to about 160, about 120 to about 155, about 120 to about 150, about 120 to about 145, about 120 to about 140, about 120 to about 135, about 120 to about 130, about 120 to about 125, about 125 to about 200, about 125 to about 195, about 125 to about 190, about 125 to about 185, about 125 to about 180, about 125 to about 175, about 125 to about 170, about 125 to about 165, about 125 to about 160, about 125 to about 155, about 125 to about 150, about 125 to about 145, about 125 to about 140, about 125 to about 135, about 125 to about 130, about 130 to about 200, about 130 to about 195, about 130 to about 190, about 130 to about 185, about 130 to about 180, about 130 to about 175, about 130 to about 170, about 130 to about 165, about 130 to about 160, about 130 to about 155, about 130 to about 150, about 130 to about 145, about 130 to about 140, about 130 to about 135, about 135 to about 200, about 135 to about 195, about 135 to about 190, about 135 to about 185, about 135 to about 180, about 135 to about 175, about 135 to about 170, about 135 to about 165, about 135 to about 160, about 135 to about 155, about 135 to about 150, about 135 to about 145, about 135 to about 140, about 140 to about 200, about 140 to about 195, about 140 to about 190, about 140 to about 185, about 140 to about 180, about 140 to about 175, about 140 to about 170, about 140 to about 165, about 140 to about 160, about 140 to about 155, about 140 to about 150, about 140 to about 145, about 145 to about 200, about 145 to about 195, about 145 to about 190, about 145 to about 185, about 145 to about 180, about 145 to about 175, about 145 to about 170, about 145 to about 165, about 145 to about 160, about 145 to about 155, about 145 to about 150, about 150 to about 200, about 150 to about 195, about 150 to about 190, about 150 to about 185, about 150 to about 180, about 150 to about 175, about 150 to about 170, about 150 to about 165, about 150 to about 160, about 150 to about 155, about 155 to about 200, about 155 to about 195, about 155 to about 190, about 155 to about 185, about 155 to about 180, about 155 to about 175, about 155 to about 170, about 155 to about 165, about 155 to about 160, about 160 to about 200, about 160 to about 195, about 160 to about 190, about 160 to about 185, about 160 to about 180, about 160 to about 175, about 160 to about 170, about 160 to about 165, about 165 to about 200, about 165 to about 195, about 165 to about 190, about 165 to about 185, about 165 to about 180, about 165 to about 175, about 165 to about 170, about 170 to about 200, about 170 to about 195, about 170 to about 190, about 170 to about 185, about 170 to about 180, about 170 to about 175, about 175 to about 200, about 175 to about 195, about 175 to about 190, about 175 to about 185, about 175 to about 180, about 180 to about 200, about 180 to about 195, about 180 to about 190, about 180 to about 185, about 185 to about 200, about 185 to about 195, about 185 to about 190, about 190 to about 200, about 190 to about 195, or about 195 to about 200) different reagent red blood cells (e.g., any of the exemplary reagent red blood cells described herein, including, e.g., the first reagent red blood cell and the second reagent red blood cell), wherein each of the reagent red blood cells had a different surface phenotype from any of the other reagent red blood cells.

Additional reagent red blood cells can be generated using any of the methods described herein, e.g., a recombinant red blood cell having a surface phenotype lacking at least one (e.g., 2, 3, 4, 5, 6, 7, 8, 9, 10, 11, 12, 13, 14, 15, 16, 17, 18, 19, or 20) antigen on its surface (e.g., any of the blood group antigens described herein or known in the art in any combination).

In some embodiments of any of the reagent red blood cells, the reagent red blood cell is a recombinant group O cell.

In some embodiments of any of the test kits described herein, the kit includes at least one reagent red blood cell that has a surface phenotype that is not naturally-occurring in a human or other mammal.

Also provided are recombinant red blood cells, wherein each recombinant red blood cell is characterized by the absence of at least one or more (e.g., 1, 2, 3, 4, 5, 6, 7, 8, 9, or 10) cell surface antigens on its surface selected from the group of: a C antigen, an E antigen, a c antigen, an e antigen, a U antigen, an S antigen, an s antigen, an hrB antigen, a Lua antigen, a Lub antigen and a CD47 antigen. Some embodiments of these recombinant red blood cells are further characterized by the absence of a D antigen on its cell surface. Other embodiments of these recombinant red blood cells are further characterized by the presence of a D antigen on its cell surface. Some embodiments of these recombinant red blood cells are further characterized by the presence of a Go(a) antigen on its cell surface. Some embodiments of these recombinant red blood cells are further characterized by the presence of a DAK antigen on its cell surface. Some embodiments of these recombinant red blood cells are characterized by the absence of a Doa antigen and a Dob antigen on its cell surface.

The surface phenotype of a reagent red blood cell described herein can be determined or confirmed using one or more antibodies that specifically recognize an antigen that is presented on the surface of the reagent red blood cell (e.g., using fluorescence-assisted cell sorting and immunofluorescence or agglutination).

The following references described the engineering of cells, including stem cells, to have altered blood group antigens: U.S. Pat. No. 5,811,130; WO2016085934; WO2015032340; CA2516123; WO2015118780; U.S. Pat. Nos. 9,200,253; 9,255,248; 9,169,462.

II. SICKLE CELL DISEASE AND TRANSFUSION THERAPY

A. Sickle Cell Disease

Sickle-cell disease (SCD) is a group of blood disorders typically inherited from a person's parents. The most common type is known as sickle-cell anaemia (SCA). It results in an abnormality in the oxygen-carrying protein hemoglobin (hemoglobin S) found in red blood cells. This leads to a rigid, sickle-like shape under certain circumstances. Problems in sickle cell disease typically begin around 5 to 6 months of age. A number of health problems may develop, such as attacks of pain ("sickle-cell crisis"), anemia, swelling in the hands and feet, bacterial infections, and stroke. Long term pain may develop as people get older. The average life expectancy in the developed world is 40 to 60 years.

Sickle-cell disease occurs when a person inherits two abnormal copies of the hemoglobin gene, one from each parent. This gene occurs in chromosome 11. Several subtypes exist, depending on the exact mutation in each hemoglobin gene. An attack can be set off by temperature changes, stress, dehydration, and high altitude. A person with a single abnormal copy does not usually have symptoms and is said to have sickle-cell trait. Such people are also referred to as carriers. Diagnosis is by a blood test and some countries test all babies at birth for the disease. Diagnosis is also possible during pregnancy.

The care of people with sickle-cell disease may include infection prevention with vaccination and antibiotics, high fluid intake, folic acid supplementation, and pain medication. Other measures may include blood transfusion, and the medication hydroxycarbamide (hydroxyurea). A small proportion of people can be cured by a transplant of bone marrow cells. As of 2015 about 4.4 million people have sickle-cell disease while an additional 43 million have sickle-cell trait. About 80% of sickle-cell disease cases are believed to occur in sub-Saharan Africa. It also occurs relatively frequently in parts of India, the Arabian peninsula, and among people of African origin living in other parts of the world. In 2015, it resulted in about 114,800 deaths.

Signs of sickle cell disease usually begin in early childhood. The severity of symptoms can vary from person to person, Sickle-cell disease may lead to various acute and chronic complications, several of which have a high mortality rate.

The terms "sickle-cell crisis" or "sickling crisis" may be used to describe several independent acute conditions occurring in patients with SCD. SCD results in anemia and crises that could be of many types including the vaso-occlusive crisis, aplastic crisis, sequestration crisis, haemolytic crisis, and others. Most episodes of sickle-cell crises last between five and seven days. "Although infection, dehydration, and acidosis (all of which favor sickling) can act as triggers, in most instances, no predisposing cause is identified."

The vaso-occlusive crisis is caused by sickle-shaped red blood cells that obstruct capillaries and restrict blood flow to an organ resulting in ischaemia, pain, necrosis, and often organ damage. The frequency, severity, and duration of these crises vary considerably. Painful crises are treated with hydration, analgesics, and blood transfusion; pain management requires opioid administration at regular intervals until the crisis has settled. For milder crises, a subgroup of patients manage on nonsteroidal anti-inflammatory drugs (NSAIDs) such as diclofenac or naproxen. For more severe crises, most patients require inpatient management for intravenous opioids; patient-controlled analgesia devices are commonly used in this setting. Vaso-occlusive crisis involving organs such as the penis or lungs are considered an emergency and treated with red-blood cell transfusions. Incentive spirometry, a technique to encourage deep breathing to minimize the development of atelectasis, is recommended.

Because of its narrow vessels and function in clearing defective red blood cells, the spleen is frequently affected. It is usually infarcted before the end of childhood in individuals suffering from sickle-cell anemia. This spleen damage increases the risk of infection from encapsulated organisms; preventive antibiotics and vaccinations are recommended for those lacking proper spleen function.

Splenic sequestration crises are acute, painful enlargements of the spleen, caused by intrasplenic trapping of red cells and resulting in a precipitous fall in hemoglobin levels with the potential for hypovolemic shock. Sequestration crises are considered an emergency. If not treated, patients may die within 1-2 hours due to circulatory failure. Management is supportive, sometimes with blood transfusion. These crises are transient, they continue for 3-4 hours and may last for one day.

Acute chest syndrome (ACS) is defined by at least two of the following signs or symptoms: chest pain, fever, pulmonary infiltrate or focal abnormality, respiratory symptoms, or hypoxemia. It is the second-most common complication and it accounts for about 25% of deaths in patients with SCD, majority of cases present with vaso-occlusive crises then they develop ACS. Nevertheless, about 80% of patients have vaso-occlusive crises during ACS.

Aplastic crises are acute worsenings of the patient's baseline anaemia, producing pale appearance, fast heart rate, and fatigue. This crisis is normally triggered by parvovirus B19, which directly affects production of red blood cells by invading the red cell precursors and multiplying in and destroying them. Parvovirus infection almost completely prevents red blood cell production for two to three days. In normal individuals, this is of little consequence, but the shortened red cell life of SCD patients' results in an abrupt, life-threatening situation. Reticulocyte counts drop dramatically during the disease (causing reticulocytopenia), and the rapid turnover of red cells leads to the drop in hemoglobin. This crisis takes 4 days to one week to disappear. Most patients can be managed supportively; some need blood transfusion.

Haemolytic crises are acute accelerated drops in hemoglobin level. The red blood cells break down at a faster rate. This is particularly common in patients with coexistent G6PD deficiency. Management is supportive, sometimes with blood transfusions.

One of the earliest clinical manifestations is dactylitis, presenting as early as six months of age, and may occur in children with sickle-cell trait. The crisis can last up to a month. Another recognised type of sickle crisis, acute chest syndrome, is characterized by fever, chest pain, difficulty breathing, and pulmonary infiltrate on a chest X-ray. Given that pneumonia and sickling in the lung can both produce these symptoms, the patient is treated for both conditions. It can be triggered by painful crisis, respiratory infection, bone-marrow embolisation, or possibly by atelectasis, opiate administration, or surgery. Hematopoietic ulcers may also occur.

Normally, humans have hemoglobin A, which consists of two alpha and two beta chains, hemoglobin A2, which consists of two alpha and two delta chains, and hemoglobin F, consisting of two alpha and two gamma chains in their bodies. Out of these three types, hemoglobin F dominates until about 6 weeks of age. Afterwards, hemoglobin A dominates throughout life. In people diagnosed with sickle cell disease, at least one of the β-globin subunits in hemoglobin A is replaced with what's known as hemoglobin S. In sickle cell anemia, a common form of sickle cell disease, hemoglobin S replaces both β-globin subunits in the hemoglobin.

Sickle-cell conditions have an autosomal recessive pattern of inheritance from parents. The types of hemoglobin a person makes in the red blood cells depend on what hemoglobin genes are inherited from her or his parents. If one parent has sickle-cell anaemia and the other has sickle-cell trait, then the child has a 50% chance of having sickle-cell disease and a 50% chance of having sickle-cell trait. When both parents have sickle-cell trait, a child has a 25% chance of sickle-cell disease, 25% do not carry any sickle-cell alleles, and 50% have the heterozygous condition.

Sickle-cell gene mutation probably arose spontaneously in different geographic areas, as suggested by restriction endonuclease analysis. These variants are known as Cameroon, Senegal, Benin, Bantu, and Saudi-Asian. Their clinical importance is because some are associated with higher HbF levels, e.g., Senegal and Saudi-Asian variants, and tend to have milder disease.

In people heterozygous for HgbS (carriers of sickling hemoglobin), the polymerisation problems are minor, because the normal allele is able to produce over 50% of the hemoglobin. In people homozygous for HgbS, the presence of long-chain polymers of HbS distort the shape of the red blood cell from a smooth doughnut-like shape to ragged and full of spikes, making it fragile and susceptible to breaking within capillaries. Carriers have symptoms only if they are deprived of oxygen (for example, while climbing a mountain) or while severely dehydrated. The sickle-cell disease occurs when the sixth amino acid, glutamic acid, is replaced by valine to change its structure and function; as such, sickle-cell anemia is also known as E6V. Valine is hydrophobic, causing the hemoglobin to collapse on itself occasionally. The structure is not changed otherwise. When enough hemoglobin collapses on itself the red blood cells become sickle-shaped.

The gene defect is a known mutation of a single nucleotide (see single-nucleotide polymorphism—SNP) (A to T) of the β-globin gene, which results in glutamic acid (E/Glu) being substituted by valine (V/Val) at position 6. Hemoglobin S with this mutation is referred to as HbS, as opposed to the normal adult HbA. This is normally a benign mutation, causing no apparent effects on the secondary, tertiary, or quaternary structures of hemoglobin in conditions of normal oxygen concentration. What it does allow for, under conditions of low oxygen concentration, is the polymerization of the HbS itself. The deoxy form of hemoglobin exposes a hydrophobic patch on the protein between the E and F helices. The hydrophobic side chain of the valine residue at position 6 of the beta chain in hemoglobin is able to associate with the hydrophobic patch, causing HbS molecules to aggregate and form fibrous precipitates.

The allele responsible for sickle-cell anaemia can be found on the short arm of chromosome 11, more specifically 11p15.5. A person who receives the defective gene from both father and mother develops the disease; a person who receives one defective and one healthy allele remains healthy, but can pass on the disease and is known as a carrier or heterozygote. Heterozygotes are still able to contract malaria, but their symptoms are generally less severe.

Due to the adaptive advantage of the heterozygote, the disease is still prevalent, especially among people with recent ancestry in malaria-stricken areas, such as Africa, the Mediterranean, India, and the Middle East. Malaria was historically endemic to southern Europe, but it was declared eradicated in the mid-20th century, with the exception of rare sporadic cases.

The malaria parasite has a complex lifecycle and spends part of it in red blood cells. In a carrier, the presence of the malaria parasite causes the red blood cells with defective hemoglobin to rupture prematurely, making the *Plasmodium* parasite unable to reproduce. Further, the polymerization of Hb affects the ability of the parasite to digest Hb in the first place. Therefore, in areas where malaria is a problem, people's chances of survival actually increase if they carry sickle-cell trait (selection for the heterozygote).

In the United States, with no endemic malaria, the prevalence of sickle-cell anaemia among African Americans is lower (about 0.25%) than in West Africa (about 4.0%) and is falling. Without endemic malaria, the sickle-cell mutation is purely disadvantageous and tends to decline in the affected population by natural selection, and now artificially through prenatal genetic screening. However, the African American community descends from a significant admixture of several African and non-African ethnic groups and also represents the descendants of survivors of slavery and the slave trade. Thus, a lower degree of endogamy and, particularly, abnormally high health-selective pressure through slavery may be the most plausible explanations for the lower prevalence of sickle-cell anemia (and, possibly, other genetic diseases) among African Americans compared to West Africans. Another factor that limits the spread of sickle-cell genes in North America is the absence of cultural proclivities to polygamy, which allows affected males to continue to seek unaffected children with multiple partners.

B. Transfusion Therapy and Alloimmunization

RBC transfusion is an essential treatment for patients with SCD but development of alloimmunization is a significant complication that affects 30-50% of those who require chronic transfusion therapy. Patients with SCD are at higher risk of alloimmunization than other transfused patient populations, often developing multiple alloantibodies and broadly reactive antibodies that are difficult to identify. One major explanation for high alloimmunization rates in patients with SCD is the disparate distribution of RBC antigens between patients who are primarily of African ancestry, and blood donors of non-African ethnic backgrounds (Vichinsky, 1990). The frequency of C, E, K, Jkb, Fya, Lea and S antigens is significantly lower in individuals of African descent compared to blood donors who are primarily of European descent. Outside of ABO, the Rh blood group system is the most immunogenic. Since sensitization to Rh antigens (D, C, c, E, e) and to K (a Kell system antigen) comprise a majority of the RBC antibodies encountered in patients with SCD, consensus guidelines recommend provision of C, E, K-matched RBCs to this patient population (Yawn, 2014). Transfusion with RBC units from African American donors with the same ethnic background, who are more likely to have similar blood group antigen profiles, has also been suggested to mitigate exposure to foreign antigens that cause high rates of alloimmunization. Despite this strategy, alloimmunization has remained alarmingly high with 58% of chronic and 15% of episodically transfused patients immunized (Chou, 2013).

Antibodies directed against the Rh blood group system were the most common antibodies, suggesting that transfused RBCs were not truly Rh-matched (D, C, and E). Genetic analysis of the two genes, RHD and RHCE, that encode the Rh antigens revealed that >85% of patients carry variant alleles that result in loss or alteration of Rh antigenic epitopes. Variations in Rh blood group antigen expression are not detected by traditional blood bank tests which detect only the principal Rh antigens (D,C,c,E,e). Consequently, patients with SCD are at risk of Rh antibody formation when exposed to conventional Rh antigens on donor RBCs (Chou, 2013). This problem is unique to patients with SCD who are primarily of African Black ethnicity, as RH variation occurs in <3% of individuals from other ethnic populations, in contrast to 85% of Blacks. In addition to the inability to detect Rh variation on the RBCs of patients with SCD, the accurate identification of the Rh antibodies they form as a consequence of having inherited altered Rh proteins is not possible with commercial RBC reagents. These RBC reagents are from Caucasian donors and represent Caucasian RBC phenotypes. This limits the ability for blood banks to determine donor compatibility, requires costly sample referral to specialized reference laboratories, and ultimately, delays transfusion and patient care, emphasizing the need for specialized typing reagents for this patient population.

The Rh system is the most complex of all blood group systems and includes greater than 50 different antigens encompassing polymorphic epitopes, but "Rh typing" of RBCs tests for five (D,C,c,E,e) common in all populations. The Rh proteins are encoded by two genes: RHD encodes the D antigen and RHCE encodes the CE antigens in various combinations (ce, cE, Ce, CE). Individuals with D antigen expressed are "Rh positive" and the absence of D, usually due to RHD gene deletion, are "Rh negative." The highest incidence of "Rh negative" (15-17%) occurs in Caucasians of European ancestry. The RHD and RHCE genes are inherited as a haplotype with allele frequencies that differ in various populations.

RHD and RHCE genetic variants are frequent in individuals of African Black ethnicity and result in altered epitopes often termed "partial" Rh antigens because they lack common epitopes. Patients with variant RH who lack commonly encoded epitopes are at risk of antibody production if exposed to foreign Rh epitopes via transfusion or pregnancy. Thus, RhD+ individuals with "partial D" antigen may form anti-D (to the epitopes of D they lack) when exposed to conventional D antigen (Wagner, 2002; Westhoff, 2010; Chou, 2013). For example, RHD*DAU4 encodes a protein in which lysine replaces glutamic acid at amino acid position 233 resulting in loss or alteration of one or more common RhD epitopes. Variant RHCE alleles encoding "partial C, c, or e antigens" occurs frequently in African Blacks, and their RBCs often lack high prevalence Rh antigenic epitopes, such as hrB and hrS, and express novel antigenic epitopes (V, VS) (Noizat-Pirenne, 2011; Denomme, 2014). For example, the relatively common altered allele, RHCE*ce(733G), encodes a new antigen VS and loss of the high prevalence antigen hrB. The inventors demonstrated that variant RHD or RHCE contributes to Rh alloimmunization and delayed transfusion reactions in patients with SCD (Chou, 2013). Genotyping can be used to type patients to identify RH variants and guide antibody evaluations, but at the hospital level, routine blood bank reagents are needed to identify anti-Rh antibodies with the precision or "fine specificity" needed for clinical decision-making. While genetic matching of blood may be feasible in the future, the cost and infrastructure to do so is currently prohibitive. The required high-resolution genotyping of RH and other blood group antigens to truly match patients with SCD cost ~$2,000/donor unit. With a large exchange transfusion program at CHOP, the average number of units is 7 per transfusion visit. Thus, generating iPSC-derived RBC reagents now to improve antibody identification, donor selection, and transfusion safety is critical.

Other antibodies that are often found in the serum of patients with SCD include anti-U, anti-hrS, and anti-hrB, but these are heterogeneous specificities and often are not compatible within each group. RH genotyping can accurately classify the fine specificity and is key to finding compatible donors. Approximately 2% (U$^-$) to 4% (hrS$^-$ and hrB$^-$) of African-Americans lack these antigens on their RBCs, and are therefore at risk of making allo-antibodies. These allo-antibodies, which are clinically significant, cannot be distinguished from auto-antibodies in traditional testing, as they react with all red cells provided with current commercial panels.

It is generally accepted that patients with SCD should have extended RBC testing performed early in life for the principal clinically significant antigens including Rh (D, C, c, E, e), Kell (K, k), Duffy (Fya, Fyb), Kidd (Jka, Jkb), Dombrock (Doa,Dob), and MNS (M, N, S, s) antigens, which guides donor RBC selection and antibody evaluations. Antibody detection is performed prior to each transfusion to determine the presence of antibodies in patient serum directed to RBC antigens. Antibody detection involves incubating the patient's serum against "screening" RBCs which are prepared from group O donors that express the major antigens in different combinations (FIG. 1). Commercial RBC reagents represent common Caucasian RBC antigen phenotypes and do not include the "partial" Rh antigens expressed in individuals of African Black ethnicity.

Two or three reagent RBCs with known antigen profiles are used for routine antibody detection (FIG. 1, cells I, II, III). A control consisting of the patient's own cells and serum is included to control for spontaneous agglutination and to test for the presence of an autoantibody. The patient serum is incubated with reagent RBCs and an antigen-antibody reaction is detected as agglutination of cells, indicating a positive test for antibodies to RBC antigens (FIG. 2). For example, a patient with anti-K in the serum will show no reactivity with cell I and II, but will be positive with cell III (FIG. 1). When positive reactivity is detected in this initial "antibody screening", the patient's serum is then tested against a panel of 10-12 RBCs with different antigen profiles to definitively determine antibody specificity to the blood group antigen. Importantly, antibody specificity is determined if the patient's serum reacts with RBCs expressing the offending antigen and does not react with RBCs lacking the antigen. Transfusion of RBCs expressing an antigen that the patient has been immunized against can cause a life-threatening hemolytic transfusion reaction. Thus, it is imperative that the patient receive RBCs lacking all antigens she/he has been immunized to in their lifetime.

Positive reactivity with all panel RBCs or "panagglutination" presents a dilemma. In FIG. 1, the patient's serum showed 2-3+ agglutination with the screening cells I, II, III and the autocontrol. An additional panel of 10-12 cells will also show positive reactions. These results are very difficult to interpret in chronically transfused patients. The positive autocontrol suggests the patient has made an antibody to their own RBCs, but this "apparent autoantibody" can be due to an alloantibody bound to circulating donor cells. This pattern of "panagglutination" results when the patient makes an antibody to a high prevalence antigen that is absent on their RBCs. When this occurs, antibody and compatibility testing with donor RBCs becomes complicated and hospital blood bank laboratories must send the samples to reference laboratories. Specialized testing is time-consuming, increases cost, and delays treatment. To streamline this process, FIG. 1 shows three additional typing reagent RBCs that the inventors propose to use for more accurate identification of antibody specificity in blood banks and improve patient transfusion therapy.

C. Other Therapeutic Methods

A recombinant red blood cell herein can be administered to a subject in need thereof to treat the subject. For example, a recombinant red blood cell described herein can be administered to a patient identified as being in need thereof and that is blood antigen compatible for the recombinant red blood cell (e.g., using any of the methods described herein), with one example being patients with SCD. In other methods, any recombinant red blood cell described herein can be administered to a patient that in need thereof (e.g., a patient having a hematological disorder, e.g., hereditary anemia, β-thalassemia, or a hematologic cancer), once the subject has been determined to be compatible for the recombinant red blood cell.

As used herein, "administering", "transfusing" or "treating" includes reducing the number, frequency, or severity of one or more (e.g., two, three, four, or five) signs or symptoms of a hereditary anemia, β-thalassemia, sickle cell disorder, or cancer in a patient (e.g., any of the cancers described herein). In some embodiments, administering can include providing a blood-compatible tissue and/or blood-compatible blood product to a patient that is identified as being compatible with the selected tissue and/or blood product. In some embodiments, administering can delay or inhibit disease progression. In some embodiments, administering is used for massive bleeding transfusion (e.g., emergency massive bleeding transfusion) (e.g., transfusion with O$^-$ Rh$^-$ null reagent red blood cells).

Non-limiting examples of cancer include acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma, involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thy mom and thymic carcinoma, thyroid cancer, urethral cancer, uterine cancer, vaginal cancer, vulvar cancer, and Wilms' tumor. Additional examples of cancer are known in the art.

In some embodiments of any of the methods described herein, the cancer is a hematologic cancer (e.g., leukemia (e.g., acute lymphoblastic leukemia (ALL), acute myeloid leukemia (AML), chronic lymphocytic leukemia (CLL), chronic myelogenous leukemia (CML)), lymphoma (e.g., Hodgkin's lymphoma or non-Hodgkin's lymphoma), or multiple myeloma).

In some embodiments of any of the methods described herein, the cancer is characterized by having a population of cancer cells that express CD38 or CD47. In some embodiments of any of the methods described herein, the patient has received at least one dose of an anti-CD38 therapy or an anti-CD47 therapy.

In some instances, the immunotherapy (e.g., anti-CD38 therapy or anti-CD47 therapy) causes all red blood cells to agglutinate, thereby preventing the detection of common blood group antigens from being detected underneath the pan-agglutination caused by the immunotherapy.

A recombinant red blood cell described herein (e.g., a Lua-b⁻ recombinant red blood cell or a CD47 null recombinant red blood cell) can be used as a method of treatment, e.g., upon administration or transfusion in a patient identified that has received an immunotherapy that causes all red blood cells to agglutinate. Any of the recombinant red blood cells described herein can be administered to a subject in need thereof, where the recombinant red blood cell has been determined to be compatible with the subject (e.g., using any of the methods described herein).

III. EXEMPLARY METHODS OF GENETICALLY MODIFYING CELLS

Methods of genetically modifying cells to express an antigen on its surface (e.g., any of the exemplary blood group antigens described herein or known in the art) are known in the art. Non-limiting examples of methods that can be used to introduce a nucleic acid or an expression vector into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), or nanoparticle transfection.

Methods of genetically modifying cells to decrease or prevent the expression of an antigen on its cell surface (e.g., any of the blood group antigens described herein or known in the art) are known in the art. Non-limiting examples of methods that can be used to decrease or prevent the expression of an antigen on the surface of a cell (e.g., any of the blood group antigens described herein or known in the art) include introducing a nucleic acid or an expression vector that includes an inhibitory nucleic acid (e.g., a short hairpin RNA, a small interfering RNA, or a microRNA) targeting a nucleic acid encoding the antigen into the cell by lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), or nanoparticle transfection.

In some instances, the CRISPR/Cas9 system or any other site-specific recombinase is used to delete a gene encoding a cell surface antigen (e.g., any of the blood group antigens described herein or known in the art) from a cell or to introduce a recombinant gene construct to express an alternative antigen on the cell. Briefly, a guide RNA is designed that is complementary to the endogenous gene encoding the cell surface antigen (e.g., any of the blood group antigens described herein or known in the art). The designed guide RNA and Cas9 enzyme are introduced into a cell and the gene of interest (e.g., a gene encoding a cell surface antigen) is deleted by homologous recombination. In other examples, a transcription activator-like effector nuclease (TALEN) or a zinc-finger-like enzyme can be used to delete or add a gene of interest (e.g., a gene encoding a cell surface antigen) to a cell.

Figure 22A:
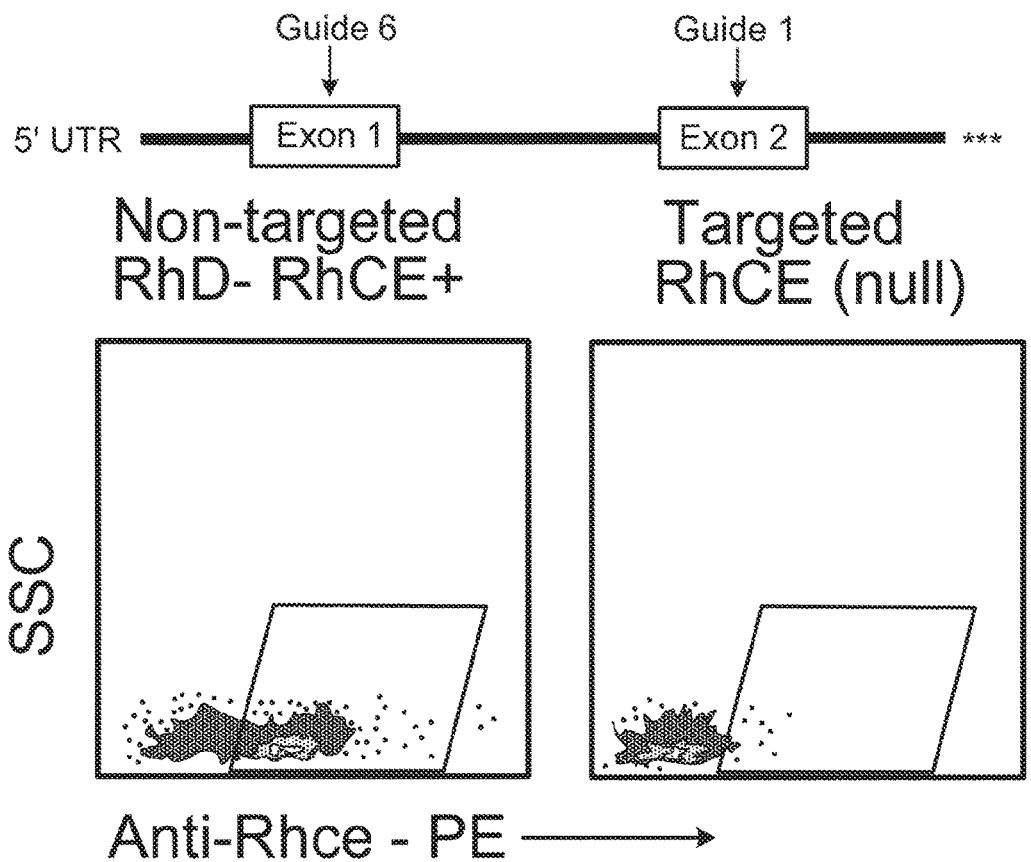
FIG. 22A. Representative schematic of a CRISPR/CAS9 strategy to generate Rh-null induced pluripotent stem cells (iPSCs). The left diagram shows two target guide RNA to RHCE gene, and the right diagram shows a representative FACS plot gated for loss of expression of RhCE.

In some instances, the CRISPR/Cas9 system is used to engineer a Group O, Rh-null cell line as a first step (see, e.g., Table 1.4 and FIG. 22A). For example, to disrupt expression of RHCE, a guide RNA is designed that target the first or second exon of the RHCE gene. Clones in which repair by non-homologous-end-joining has resulted in the introduction of a stop codon are screened and selected. iPSCs are first transduced with an inducible Cas9 and guide RNA vectors and successfully transduced clones will be selected using antibiotics. Expression of the Cas9 protein is later induced with doxycycline and clones in which mutations have been introduced are screened by PCR. Next, other atypical Rh proteins are introduced into the Rh-null cell line to generate novel cells not found in humans to date. In some instances, reagent red blood cells are generated using a transgene-free approach.

Figure 22B:
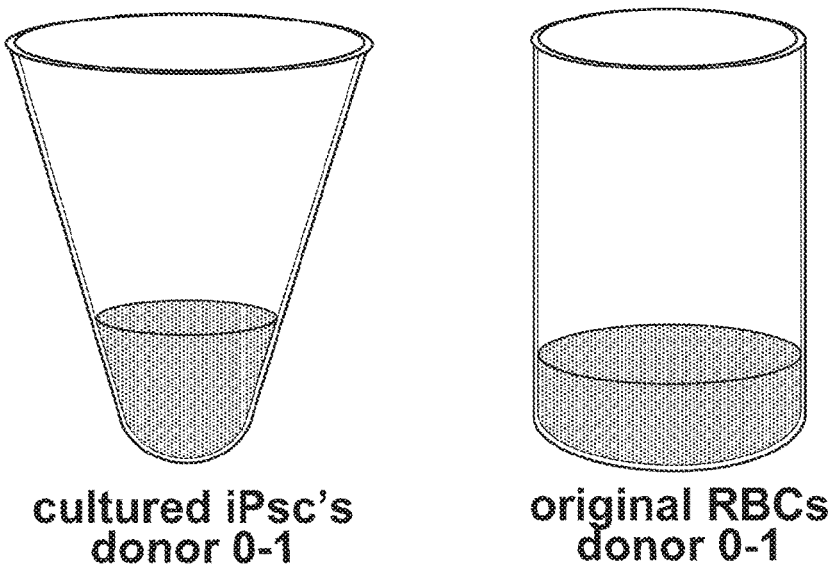
FIG. 22B. Representative image of recombinant reagent cultured red blood cells (cRBCs)-derived from iPSCs and donor-derived red blood cells (RBCs).
Figure 22C:
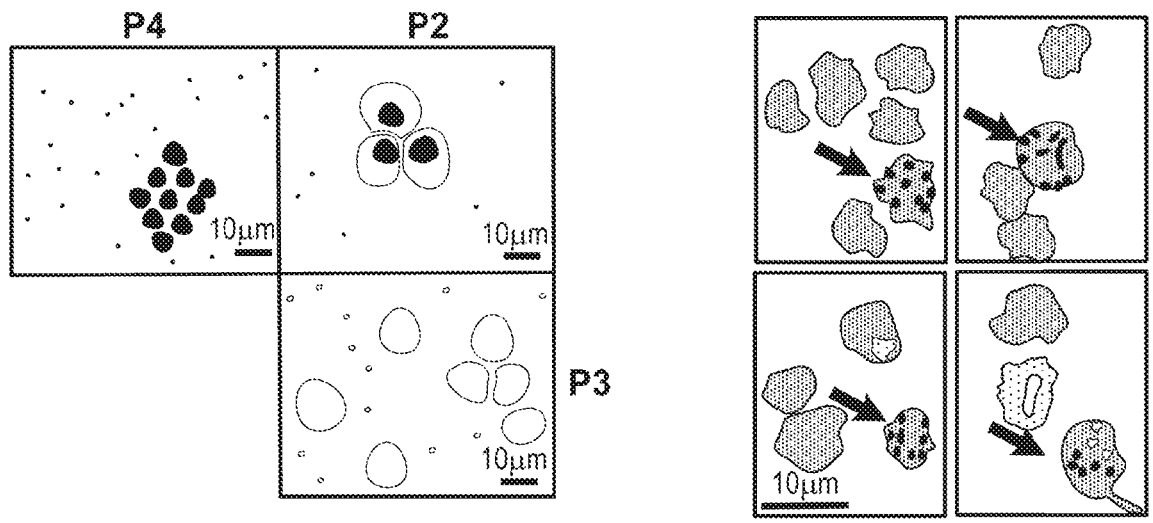
FIG. 22C. Representative images of the morphology of cRBCs.
Figure 22D:
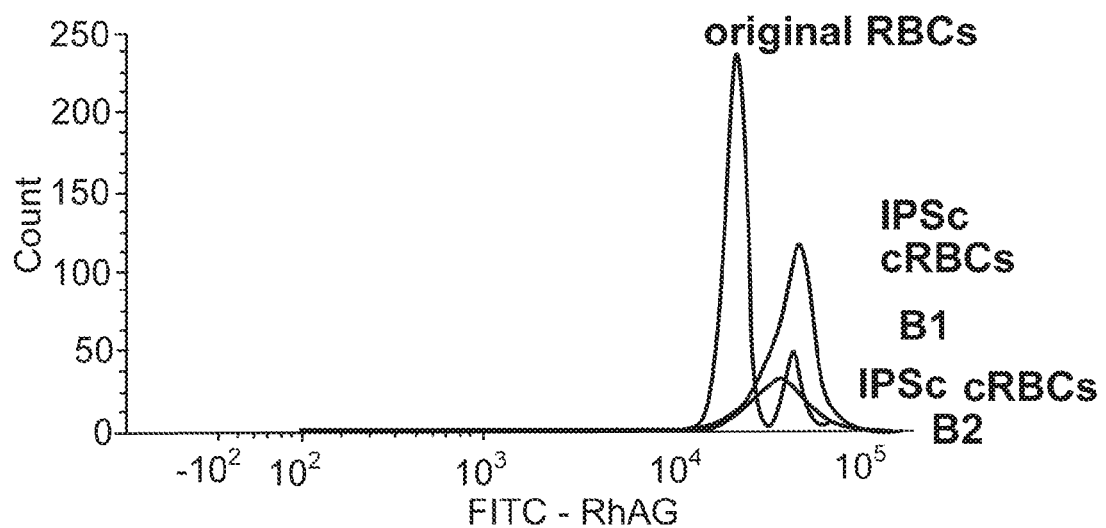
FIG. 22D. Representative fluorescence-activated cell sorting (FACS) histogram for Rh-associated glycoprotein (RhAG) expression in original donor red blood cells (original RBCs) and two iPSC cRBCs cell lines (iPSC cRBCs B1 and B2).

In some examples, a reagent red blood cells (e.g., a first reagent red blood cell or a second reagent red blood cell) produced in the laboratory can express the same blood group antigen profiles when compared to a donor RBCs frozen in liquid nitrogen. FIGS. 22B-D illustrate exemplary reagent red blood cells differentiated from iPSCs, and expression of RhAG (Rh associated glycoprotein) on the donor original red cells and from iPSCs.

A. CRISPR and Nucleases

CRISPRs (clustered regularly interspaced short palindromic repeats) are DNA loci containing short repetitions of base sequences. Each repetition is followed by short segments of "spacer DNA" from previous exposures to a virus. CRISPRs are found in approximately 40% of sequenced eubacteria genomes and 90% of sequenced archaea. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and silence these exogenous genetic elements like RNAi in eukaryotic organisms.

Repeats were first described in 1987 for the bacterium Escherichia coli. In 2000, similar clustered repeats were identified in additional bacteria and archaea and were termed Short Regularly Spaced Repeats (SRSR). SRSR were renamed CRISPR in 2002. A set of genes, some encoding putative nuclease or helicase proteins, were found to be associated with CRISPR repeats (the cas, or CRISPR-associated genes).

In 2005, three independent researchers showed that CRISPR spacers showed homology to several phage DNA and extrachromosomal DNA such as plasmids. This was an indication that the CRISPR/cas system could have a role in adaptive immunity in bacteria. Koonin and colleagues proposed that spacers serve as a template for RNA molecules, analogously to eukaryotic cells that use a system called RNA interference.

In 2007 Barrangou, Horvath (food industry scientists at Danisco) and others showed that they could alter the resistance of Streptococcus thermophilus to phage attack with spacer DNA. Doudna and Charpentier had independently been exploring CRISPR-associated proteins to learn how bacteria deploy spacers in their immune defenses. They jointly studied a simpler CRISPR system that relies on a protein called Cas9. They found that bacteria respond to an invading phage by transcribing spacers and palindromic DNA into a long RNA molecule that the cell then uses tracrRNA and Cas9 to cut it into pieces called crRNAs.

CRISPR was first shown to work as a genome engineering/editing tool in human cell culture by 2012 It has since been used in a wide range of organisms including baker's yeast (S. cerevisiae), zebra fish, nematodes (C. elegans), plants, mice, and several other organisms. Additionally, CRISPR has been modified to make programmable transcription factors that allow scientists to target and activate or silence specific genes. Libraries of tens of thousands of guide RNAs are now available.

The first evidence that CRISPR can reverse disease symptoms in living animals was demonstrated in 2014, when MIT researchers cured mice of a rare liver disorder. Since 2012, the CRISPR/Cas system has been used for gene editing (silencing, enhancing or changing specific genes) that even works in eukaryotes like mice and primates. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (E coli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (~30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype E coli) proteins (called CasA-E in E. coli) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in E. coli requires Cascade and Cas3, but not Cas1 and Cas2. The Cmr (Cas RAMP module) proteins found in Pyrococcus furiosus and other prokaryotes form a functional complex with small CRISPR RNAs that recognizes and cleaves complementary target RNAs. RNA-guided CRISPR enzymes are classified as type V restriction enzymes.

Cas9 is a nuclease, an enzyme specialized for cutting DNA, with two active cutting sites, one for each strand of the double helix. The team demonstrated that they could disable one or both sites while preserving Cas9's ability to home located its target DNA. Jinek et al. (2012) combined tracrRNA and spacer RNA into a "single-guide RNA" molecule that, mixed with Cas9, could find and cut the correct DNA targets. Jinek et al. (2012) proposed that such synthetic guide RNAs might be able to be used for gene editing.

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of Francisella novicida uses a unique, small, CRISPR/Cas-associated RNA (scaRNA) to repress an endogenous transcript encoding a bacterial lipoprotein that is critical for F. novicida to dampen host response and promote virulence. Wang et al. (2015) showed that coinjection of Cas9 mRNA and sgRNAs into the germline (zygotes) generated nice with mutations. Delivery of Cas9 DNA sequences also is contemplated.

See also U.S. Patent Publication 2014/0068797, which is incorporated by reference in its entirety.

Clustered Regularly Interspaced Short Palindromic Repeats from Prevotella and Francisella 1 or CRISPR/Cpf1 is a DNA-editing technology analogous to the CRISPR/Cas9 system. Cpf1 is an RNA-guided endonuclease of a class II CRISPR/Cas system. This acquired immune mechanism is found in Prevotella and Francisella bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

CRISPR/Cpf1 was found by searching a published database of bacterial genetic sequences for promising bits of DNA. Its identification through bioinformatics as a CRISPR system protein, its naming, and a hidden Markov model (HMM) for its detection were provided in 2012 in a release of the TIGRFAMs database of protein families. Cpf1 appears in many bacterial species. The ultimate Cpf1 endonuclease that was developed into a tool for genome editing was taken from one of the first 16 species known to harbor it. Two candidate enzymes from *Acidaminococcus* and Lachnospiraceae display efficient genome-editing activity in human cells.

A smaller version of Cas9 from the bacterium *Staphylococcus aureus* is a potential alternative to Cpf1.

The systems CRISPR/Cas are separated into three classes. Class 1 uses several Cas proteins together with the CRISPR RNAs (crRNA) to build a functional endonuclease. Class 2 CRISPR systems use a single Cas protein with a crRNA. Cpf1 has been recently identified as a Class II, Type V CRISPR/Cas systems containing a 1,300 amino acid protein.

The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alfa-helical recognition lobe of Cas9.

Cpf1 CRISPR-Cas domain architecture shows that Cpf1 is functionally unique, being classified as Class 2, type V CRISPR system. The Cpf1 loci encode Cas1, Cas2 and Cas4 proteins more similar to types I and III than from type II systems. Database searches suggest the abundance of Cpf1-family proteins in many bacterial species.

Functional Cpf1 doesn't need the tracrRNA, therefore, only crRNA is required. This benefits genome editing because Cpf1 is not only smaller than Cas9, but also it has a smaller sgRNA molecule (proximately half as many nucleotides as Cas9).

The Cpf1-crRNA complex cleaves target DNA or RNA by identification of a protospacer adjacent motif 5'-YTN-3' (where "Y" is a pyrimidine and "N" is any nucleobase) or 5'-TTN-3', in contrast to the G-rich PAM targeted by Cas9. After identification of PAM, Cpf1 introduces a sticky-end-like DNA double-stranded break of 4 or 5 nucleotides overhang.

The CRISPR/Cpf1 system consist of a Cpf1 enzyme and a guide RNA that finds and positions the complex at the correct spot on the double helix to cleave target DNA. CRISPR/Cpf1 systems activity has three stages:

Adaptation, during which Cast and Cas2 proteins facilitate the adaptation of small fragments of DNA into the CRISPR array;
Formation of crRNAs: processing of pre-cr-RNAs producing of mature crRNAs to guide the Cas protein; and
Interference, in which the Cpf1 is bound to a crRNA to form a binary complex to identify and cleave a target DNA sequence.

B. sgRNA

As an RNA guided protein, Cas9 requires a short RNA to direct the recognition of DNA targets (Mali et al., 2013a). Though Cas9 preferentially interrogates DNA sequences containing a PAM sequence NGG it can bind here without a protospacer target. However, the Cas9-sgRNA complex requires a close match to the sgRNA to create a double strand break (Cho et al., 2013; Hsu et al., 2013). CRISPR sequences in bacteria are expressed in multiple RNAs and then processed to create guide strands for RNA (Bikard et al., 2013). Because Eukaryotic systems lack some of the proteins required to process CRISPR RNAs the synthetic construct sgRNA was created to combine the essential pieces of RNA for Cas9 targeting into a single RNA expressed with the RNA polymerase type III promoter U6 (Mali et al., 2013b,c). Synthetic sgRNAs are slightly over 100 bp at the minimum length and contain a portion which is targets the 20 protospacer nucleotides immediately preceding the PAM sequence NGG; sgRNAs do not contain a PAM sequence.

IV. PLURIPOTENT CELLS

In some instances, the inventors will utilize pluripotent stems cells (PSCs), such as induced PSCs. Pluripotent stem cells are master cells, which are capable of making cells from all three basic body layers. As such, they can potentially produce any cell or tissue the body needs to repair itself. This "master" property is called pluripotency.

Pluripotent stem cells hold great promise in the field of regenerative medicine. Because they can propagate indefinitely, as well as give rise to every other cell type in the body (such as neurons, heart, pancreatic, and liver cells), they represent a single source of cells that could be used to replace those lost to damage or disease. The most well-known type of pluripotent stem cell is the embryonic stem cell. However, since the generation of embryonic stem cells involves destruction (or at least manipulation) of the pre-implantation stage embryo, there has been much controversy surrounding their use. Further, because embryonic stem cells can only be derived from embryos, it has so far not been feasible to create patient-matched embryonic stem cell lines.

Induced pluripotent stem cells (also known as iPS cells or iPSCs) are a type of pluripotent stem cell that can be generated directly from adult cells. Since iPSCs can be derived directly from adult tissues, they not only bypass the need for embryos, but can be made in a patient-matched manner, which means that each individual could have their own pluripotent stem cell line. These unlimited supplies of autologous cells could be used to generate transplants without the risk of immune rejection. While the iPSC technology has not yet advanced to a stage where therapeutic transplants have been deemed safe, iPSCs are readily being used in personalized drug discovery efforts and understanding the patient-specific basis of disease.

iPSCs are typically derived by introducing products of specific sets of pluripotency-associated genes, or "reprogramming factors," into a given cell type. The original set of reprogramming factors (also dubbed Yamanaka factors) are the transcription factors Oct4 (Pou5f1), Sox2, cMyc, and Klf4. While this combination is most conventional in producing iPSCs, each of the factors can be functionally replaced by related transcription factors, miRNAs, small molecules, or even non-related genes such as lineage specifiers.

iPSC derivation is typically a slow and inefficient process, taking 1-2 weeks for mouse cells and 3-4 weeks for human cells, with efficiencies around 0.01%-0.1%. However, considerable advances have been made in improving the efficiency and the time it takes to obtain iPSCs. Upon introduction of reprogramming factors, cells begin to form colonies that resemble pluripotent stem cells, which can be isolated based on their morphology, conditions that select for their growth, or through expression of surface markers or reporter genes.

In 2014, type O red blood cells were synthesized at the Scottish National Blood Transfusion Service from iPSC. The cells were induced to become a mesoderm, then blood cells, and then red blood cells. A final step was to make them eject their nuclei and mature properly.

V. NUCLEIC ACID DELIVERY

In cell engineering studies, expression cassettes are employed to express a transcription product. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

B. 2A Protease

The 2A-like self-cleaving domain is derived from the insect virus *Thosea asigna* (TaV 2A peptide) (Chang et al., 2009). 2A-like domains have been shown to function across eukaryotes and cause cleavage of amino acids to occur co-translationally within the 2A-like peptide domain. Therefore, inclusion of TaV 2A peptide allows the expression of multiple proteins from a single mRNA transcript. Importantly, the domain of TaV when tested in eukaryotic systems have shown greater than 99% cleavage activity (Donnelly et al., 2001).

C. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One particular method for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them mRNAs for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/1) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EP 0273085).

VI. ASSAYS, KITS AND COMPOSITIONS

A. Methods of Determining Blood Group Antigen Compatibility

Reagent red blood cells generated in culture in the laboratory can be used in blood bank standard assays for identifying antibodies to blood group antigens. In some instances, the methods provided herein can replace current methods of determining blood compatibility. In other instances, the methods provided herein can be used in addition to current methods of determining blood compatibility. The method of determining described herein may replace sending patient samples that appear incompatible by standard methods from a hospital to a reference hospital for extensive testing.

Provided herein are methods of determining blood group antigen compatibility of a patient sample that include: (a) contacting a first reagent red blood cell with a patient sample containing a plurality of antibodies; wherein the first reagent red blood cell is characterized by the presence of one or more (e.g., two or more, three or more, four or more, five or more, six or more, seven or more, eight or more, nine or more, ten or more, fifteen or more, twenty or more, twenty-five or more, thirty or more, thirty-five or more, forty or more, forty-five or more, or fifty or more) blood group antigens (e.g., any of the blood group antigens described herein or known in the art, in any combination) on its surface; and (b) contacting a second reagent red blood cell with the patient sample; wherein the second reagent red blood cell is characterized by the absence of at least one (e.g., one, two, three, four, five, six, seven, eight, nine, or ten) of the one or more cell surface antigens on its surface; (c) detecting whether agglutination occurs upon contacting the first reagent red blood cell with the patient sample; (d) detecting whether agglutination occurs when contacting the second reagent blood cell with the patient sample; and (e) identifying that the patient sample is compatible with the at least one of the one or more cell surface antigens when no agglutination is detected in steps (c) and (d), or identifying that the patient sample is not compatible with the at least one of the one or more cell surface antigens when agglutination is detected in step (c) but is not detected in step (d), where: the first reagent red blood cell and the second reagent red blood cell have the same surface phenotype, except for the at least one cell surface antigen. In some embodiments of these methods, the one or more blood group antigens are selected from the group of: a C antigen, an E antigen, a c antigen, an e antigen, a U antigen, a S antigen, a s antigen, a hrS antigen and a hrB antigen. In some embodiments of these methods, the one or more cell surface antigens include a Lua antigen, a Lub antigen, and a CD74 antigen.

Some embodiments of these methods further include the use of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200) additional reagent red blood cells, wherein: each additional reagent red blood cell has a surface phenotype that is characterized, at least in part, by the absence of one or more cell surface antigens; and each reagent red blood cell used in the method has a different surface phenotype as compared to all the other reagent red blood cells used in the method. Some embodiments of these methods include the use of two or more, three or more, four or more, six or more, eight or more, ten or more, twelve or more, fourteen or more, sixteen or more, eighteen or more, or twenty or more additional reagent red blood cells.

In some examples of these methods, the patient sample is not compatible with the at least one of the one or more cell surface antigens when agglutination is detected in step (c), but is not detected in step (d). In some examples of these methods, steps (c) and (d) are performed at substantially the same time.

In general, any of a variety of assay formats may be used to assess binding of patient antibodies to red blood cell antigens. Some methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of blood antigen antibodies in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987).

In some examples, the detection of agglutination occurs using optical spectrometry (e.g., by detecting a change in optical density using methods known in the art). In some examples, the first and the second reagent red blood cell is labelled with a dye, a fluorescent molecule, or a luminescent molecule, which allows for ease in detection of agglutination (e.g., via light absorbance, fluorescence emission, or light emission, respectively). In some embodiments, a determination of agglutination or no agglutination is made, in part, by comparison to a control assay with reagents that are known not to agglutinate and reagents that are known to agglutinate.

In some embodiments of any of the methods described herein, the first reagent red blood cell is characterized, at least in part, by the presence of a C antigen, an E antigen, a c antigen, and an e antigen on its surface. In some embodiments, the first reagent red blood cell is further characterized by the presence of a D antigen on its surface. In some embodiments, the first reagent red blood cell is further characterized by the absence of a D antigen on its surface.

In some embodiments of any of the methods of determining blood group antigen compatibility, the second reagent red blood cell is characterized, at least in part, by the absence of a U antigen, a S antigen, and a s antigen on its surface. In some embodiments, the second reagent red blood cell is further characterized by the absence of a D antigen on its cell surface.

In some embodiments of any of the methods of determining blood group antigen compatibility, the second reagent red blood cell is characterized, at least in part, by the absence of a D antigen on its surface and the absence of a C antigen, an E antigen, a c antigen, and an e antigen on its surface. In some embodiments, the second reagent red blood cell is further characterized by the presence of a Go(a) antigen on its surface. In some embodiments, the second reagent red blood cell is further characterized by the presence of a DAK antigen on its surface.

In some embodiments of any of the methods of determining blood group antigen compatibility, the second reagent red blood cell is characterized, at least in part, by the presence of a Doa antigen and a Dob antigen on its cell surface.

In some embodiments of any of the methods of determining blood group antigen compatibility, the second reagent red blood cell is characterized, at least in part, by the absence of a hrB antigen on its surface. In some embodiments, the second reagent red blood cell is further characterized by the absence a hrS antigen on its surface. In some embodiments, the second reagent red blood cell is further characterized by the absence a D antigen on its surface. In some embodiments, the second reagent red blood cell is further characterized by the presence of a VS antigen on its surface.

In some embodiments of any of the methods of determining blood group antigen compatibility, the second reagent red blood cell is characterized, at least in part, by the absence of a C antigen, an E antigen, a c antigen, an e antigen, a U antigen, a S antigen, a s antigen, a hrS antigen and a hrB antigen on its cell surface.

In some embodiments of any of the methods of determining blood group antigen compatibility, the second target red blood cell is characterized by a phenotype selected from the group of: (i) D−, C−, E−, c−, e−; (ii) D+, C−, E−, c−, e−; (iii) D−, U−, S−, s−; (iv) D−, hrB−, VS+; (v) D−, hrB−, hrS−; (vi) D+, C−, E−, c−, e−, Go(a)+; (vii) D+, C−, E−, c−, e−, DAK+; and (viii) D−, Doa−, Dob−.

In some embodiments, the second reagent red blood cell is characterized by the absence of a Lua antigen and a Lub antigen on its surface. In some embodiments, the second reagent red blood cell is characterized by the absence of a CD47 antigen on its surface. In some embodiments of any of the methods described herein, the sample is obtained from a patient that has received an anti-CD38 immunotherapy. In some embodiments of any of the methods described herein, the sample is obtained from a patient that has received an anti-CD47 immunotherapy. In some embodiments of any of the methods described herein, the patient has previously received at least one blood transfusion or at least one dose of a blood product.

In some embodiments, the patient has or has been diagnosed as having hereditary anemia. In some embodiments, the patient has or has been diagnosed as having β-thalassemia. In some embodiments, the patient has or has been diagnosed as having sickle cell disease. In some embodiments, the patient is in need of a blood transfusion or administration of a blood product.

Methods of determining blood group antigen compatibility are known in the art. Non-limiting examples of methods of determining blood group antigen compatibility include: tube agglutination, gel card agglutination assays, immunologic gold colloid membrane aspiration test (IMAT), revised dot ELISA, microplate technology, column/gel agglutination, solid phase capture assay, Polymerase chain reaction with sequence-specific priming (PCR-SSP), and Matrix-assisted laser desorption ionization time of flight mass spectrometry (MALDI-TOF MS), and gene sequencing. These methods of determining blood group antigen compatibility can be used in addition to these methods described herein.

As can be appreciated in the art, one or more (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 35 or more, 40 or more, 45 or more, 50 or more, 55 or more, 60 or more, 65 or more, 70 or more, 75 or more, 80 or more, 85 or more, 90 or more, 95 or more, or 100 or more) additional different reagent red blood cells having varying surface phenotypes (differing from any of the other reagent red blood cells used in the method by the presence or absence of one or more surface antigens, e.g., any of the blood group antigens described herein or known in the art) can also be used in any of the methods described herein. As can be appreciated by those in the art, in any of the methods described herein, various comparisons of where agglutination is detected versus where agglutination is not detected can be used to together to provide information regarding the antigen compatibility of the sample from the patient. Such analyses can be performed using computer-implemented software or an algorithm designed to provide the antigen compatibility information for the sample from the patient.

In some embodiments of these methods, the detection of agglutination is performed using a buffer that includes one or more stabilizing agents (e.g., preservatives, buffers, antibacterial agents, anti-fungal agents, or any of the components of any of the specific buffers described herein) or potentiators to enhance reactivity (e.g. albumin, low ionic strength solutions, polyethylene glycol, and various enzyme treatments known to the art. In some embodiments of these methods, the performance of any of the methods described herein includes the use of any of the kits described herein.

In some embodiments of these methods, the methods are performed using a gel card, a multi-well assay plate, an array, a microplate, a film, a tube, a well, a paper matrix, a capillary, a slide, and a chip in which or onto which the first reagent red blood cell, the second reagent, and optionally, one or more additional red blood cell are disposed.

In some examples of any of the methods described herein, the patient sample is a plasma sample or a serum sample. In some examples of any of the methods described herein, the patient sample comprises plasma or serum.

Some embodiments of these methods can further include recording the determined antigen compatibility in the clinical records (e.g., a computer readable medium) of the patient. Some embodiments can include performing the method multiple times on different samples from the patient over time (e.g., where one or more different samples obtained from the patient are collected at different time points from the patient).

Some embodiments of these methods further include: selecting a tissue or blood product that is compatible with the at least one of the one or more cell surface antigens (e.g., blood group antigens) for a patient having its patient sample identified as being compatible with the at least one of the one or more cell surface antigens (e.g., blood group antigens); or selecting a tissue or blood product that does not include the at least one of the one or more cell surface antigens (e.g., blood group antigens) for a patient having its patient sample identified as not being compatible with the at least one of the one or more cell surface antigens (e.g., blood group antigens). Some embodiments of these methods further include: administering the selected tissue or blood product that is compatible with the at least one of the one or more cell surface antigens (e.g., blood group antigens) to the patient having its patient sample identified as being compatible with the at least one of the one or more cell surface antigens (e.g., blood group antigens); or administering the selected tissue or blood product that does not include the at least one of the one or more cell surface antigens (e.g., blood group antigens) to the patient having its patient sample identified as not being compatible with the at least one of the one or more cell surface antigens (e.g., blood group antigens).

Some embodiments of any of the methods described herein further include: transfusing a therapeutically effective amount of a second reagent red blood cell to the patient having its patient sample identified as being compatible with the at least one of the one or more cell surface antigens (e.g., a second reagent red blood cell that has a surface phenotype selected from the group of: Lua-b− and CD47−).

Some embodiments of any of the methods of determining blood group compatibility described herein further include transfusing the patient with a recombinant red blood cell (e.g., any recombinant red blood cell described herein) that is compatible with the patient's identified blood group. In some embodiments, transfusion is a method of treatment of a hematological disorder (e.g., hereditary anemia, sickle cell disorder, β-thalassemia, or a hematologic cancer).

A particularly useful assay for examining blood antibodies is a gel card assay, such as that already use to perform the ABO, RhD and Kell blood group typing, and the determination of ABO reverse group confirms the ABO group. In the field of transfusion medicine, after A and B antigens, the most important blood group antigen is the D antigen from the Rh blood group system. The determination of RhD is defined by the presence or absence of the D antigen in the red blood cells. The antigen K or KEL1 is the antigen of the Kell system most important from a clinical point of view, as the corresponding antibody is involved in hemolytic transfusion reactions (HTRs) and in hemolytic disease of the newborn (HDN).

The principle of the test is based on a gel technique described 1985 for detecting red blood cell agglutination reactions. Plastic cards are composed of multiple microtubes. Each microtube is made of a chamber, also known as incubator chamber, at the top of a long and narrow microtube, referred to as the column. Buffered gel solution containing antibody (unknown or known, such as anti-A, anti-B, anti-AB, anti-D, anti-K) has been prefilled into the microtube of the plastic card. The agglutination occurs when the red blood cell antigens react with the corresponding antibodies, present in the gel solution or in the serum or plasma sample (in the case of reverse grouping test). The gel column acts as a filter that traps agglutinated red blood cells as they pass through the gel column during the centrifugation of the card. The gel column separates agglutinated red blood cells from non-agglutinated red blood cells based on size. Any agglutinated red blood cells are captured at the top of or along the gel column, and non-agglutinated red blood cells reach the bottom of the microtube forming a pellet.

B. Kits

The present disclosure concerns kits for use with the detection methods described above. As the engineered cells may be used to detect antibodies in blood samples, both the cells and control antibodies may be included in the kit. The kits will thus comprise, in suitable container means, a plurality of engineered cells expressing rare blood antigens, or the absence of blood antigens, and optionally one or more antibodies to confirm functionality of the assay.

In certain embodiments, the cell may be pre-bound to a solid support, such as a column matrix and/or well of a microtiter plate. The reagents of the kit may take any one of a variety of forms, including detectable labels that are associated with or linked to a detection agent. Detectable labels that are associated with or attached to a secondary binding ligand are also contemplated. Exemplary secondary ligands are those secondary antibodies that have binding affinity for the first antibody. Other assays will employ agglutination as a read-out for binding.

The kits may further comprise a suitably aliquoted composition of purified blood antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

Also provided herein are kits that include any of the first reagent red blood cells and/or second reagent red blood cells described herein, any of the compositions described herein, or any of the pharmaceutical compositions described herein.

In some embodiments, the kits can include at least one dose of any of the compositions (e.g., pharmaceutical compositions) described herein. In some embodiments, the kits can provide a syringe for administering any of the pharmaceutical compositions described herein.

In some embodiments, the kits can include instructions for performing any of the methods described herein. In some embodiments of any of the kits described herein, the solid support is selected from the group consisting of: a gel card, a multi-well assay plate, an array, a microplate, a film, a tube, a well, a capillary, a paper matrix, a slide and a chip. In some embodiments of any of the kits described herein, the kit can further include glutaraldehyde or another cross-linker to stabilize antigen epitopes.

In some embodiments, the kits provided herein can include: a composition comprising a first reagent red blood cell characterized by the presence of one or more cell surface antigens (e.g., any of the blood group surface antigens described herein or known in the art) on its surface; and a composition including a second reagent red blood cell characterized by the absence of at least one of the one or more cell surface antigens on its surface, where the first reagent red blood cell and the second reagent red blood cell have the same surface phenotype except for the at least one cell surface antigen.

Some embodiments of these kits further include one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200) additional reagent red blood cells, wherein: each additional reagent red blood cell has a surface phenotype that is characterized, at least in part, by the absence of one or more cell surface antigens; and each reagent red blood cell in the kit has a different surface phenotype as compared to all the other reagent red blood cells in the kit. Some embodiments of these kits include the use of two or more, three or more, four or more, six or more, eight or more, ten or more, twelve or more, fourteen or more, sixteen or more, eighteen or more, or twenty or more additional reagent red blood cells.

Some embodiments of any of the kits provided herein, can further optionally include a solid support (e.g., any of the solid supports described herein). In some embodiments, the composition including the first reagent red blood cell and/or the composition including the second reagent red blood cell can include one or more of: an antibiotic (e.g., chloramphenicol, neomycin, and/or gentamycin), Immucor manufacturer diluent, adenine, adenosine, Alsever's solution, SAGM, and dextrose.

In some embodiments, the kits provided herein can include a first reagent red blood cell characterized by the presence of one or more cell surface antigens (e.g., any of the blood group surface antigens described herein or known in the art) on its surface; and a composition including a second reagent red blood cell characterized by the absence of at least one of the one or more cell surface antigens on its surface, where the first reagent red blood cell and the second reagent red blood cell have the same surface phenotype except for the at least one cell surface antigen. Some embodiments of these kits can further include can further include a solid support (e.g., any of the solid supports described herein).

In some embodiments of any of the kits described herein, the one or more cell surface antigens are selected from the group of: a C antigen, an E antigen, a c antigen, an e antigen, a U antigen, an S antigen, an s antigen, an hrB antigen, a Lua antigen, a Lub antigen, and a CD47 antigen.

In some examples of any of the kits described herein, the second reagent red blood cell is characterized, at least in part, by the absence of a C antigen, an E antigen, a c antigen, and an e antigen on its surface. In some examples of these kits, the second reagent red blood cell is further characterized by the absence of a D antigen on its surface. In other examples of these kits, the second reagent red blood cell is further characterized by the presence of a D antigen on its surface. In some examples of these kits, the second reagent red blood cell is characterized by the absence of a U antigen, a S antigen, and a s antigen on its surface. In some examples of these kits, the second reagent red blood cell is further characterized by the absence of a D antigen on its cell surface.

In some embodiments of any of the kits described herein, the second reagent red blood cell is characterized, at least in part, by the presence of a D antigen on its surface and the absence of a C antigen, an E antigen, a c antigen, and an e antigen on its surface. In some embodiments of these kits, the second reagent red blood cell is further characterized by the presence of a Go(a) antigen on its surface. In some embodiments of these kits, the second reagent red blood cell is further characterized by the presence of a DAK antigen on its surface.

In some embodiments of any of the kits described herein, the second reagent red blood cell is characterized, at least in part, by the absence of a Doa antigen and a Dob antigen on its surface.

In some embodiments of any of the kits described herein, the second reagent red blood cell is characterized, at least in part, by the absence of an hrB antigen on its surface. In some embodiments of these kits, the second reagent red blood cell is further characterized by the absence of an hrS antigen on its surface. In some embodiments of these kits, the second reagent red blood cell is further characterized by the absence of a D antigen on its cell surface. In some embodiments of these kits, the second reagent red blood cell is further characterized by the presence of a VS antigen on its surface.

In some embodiments of any of the kits described herein, the second reagent red blood cell is characterized, at least in part, by the absence of a C antigen, an E antigen, a c antigen, an e antigen, a U antigen, a S antigen, an s antigen, and an hrB antigen on its surface.

In some embodiments of any of the kits described herein, the second reagent red blood cell is characterized, at least in part, by a surface phenotype selected from the group of:
  (i) D−, C−, E−, c−, e−;
  (ii) D+, C−, E−, c−, e−;
  (iii) D−, U−, S−, s−;
  (iv) D−, hrB−, VS+;
  (v) D−, hrB−, hrS−;
  (vi) D+, C−, E−, c−, e−, Go(a)+;
  (vii) D+, C−, E−, c−, e−, DAK+;
  (viii) D−, Doa−, Dob−;
  (ix) Lua-b−;
  (x) CD47−; and
  (xi) any combination of two or more of the surface phenotypes of (i) to (xi).

In some embodiments of any of the kits described herein, the second reagent red blood cell is characterized by the absence of a C antigen, an E antigen, a c antigen, an e antigen, a U antigen, a S antigen, an s antigen, and an hrB antigen on its surface. In some embodiments of any of the kits described herein, the second reagent red blood cell is characterized by the surface phenotype D−, C−, E−, c−, e−, Doa− and Dob−. In some embodiments of any of the kits described herein, the second reagent red blood cell is characterized by the cell surface phenotype D−, C−, E−, c−, e−, Lua− and b−.

Some embodiments of any of the kits described herein further include one or more (e.g., 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 35 or more, 40 or more, 45 or more, 50 or more, 55 or more, 60 or more, 65 or more, 70 or more, 75 or more, 80 or more, 85 or more, 90 or more, 95 or more, or 100 or more) additional different reagent red blood cells having varying surface phenotypes (each differing from any of the other reagent red blood cells present in the kit by the presence or absence of one or more surface antigens, e.g., any of the blood group antigens described herein or known in the art).

Some embodiments of any of the kits described herein can further include one or more reagents useful for performing an agglutination assay. Some embodiments of any of the kits described herein can further include a buffer useful for performing an agglutination assay.

In some embodiments, a kit can further include an algorithm or software that can assist in the determination of blood group antigen compatibility of a patient sample.

C. Compositions

Also provided herein are compositions (e.g., pharmaceutical compositions) that include at least one (e.g., at least 2, at least 3, at least 4, at least 5, at least 6, at least 7, at least 8, at least 9, at least 10, at least 15, at least 20, at least 25, at least 30, at least 35, at least 40, at least 45, or at least 50, at least 55, at least 60, at least 65, at least 70, at least 75, at least 80, at least 85, at least 90, at least 95, at least 100, at least 105, at least 110, at least 115, at least 120, at least 130, at least 135, at least 140, at least 145, at least 150, at least 155, at least 160, at least 165, at least 170, at least 175, at least 180, at least 185, at least 190, at least 195, or at least 200) of any of the reagent red blood cells described herein (e.g., any of the first reagent red blood cells, any of the second reagent red blood cells, and any of the one or more additional reagent red blood cells described herein, or any combination thereof). In some embodiments where the compositions include at least two of any of the reagent red blood cells described herein, each of the at least two reagent red blood cells can have a different surface phenotype from the rest of the reagent red blood cells in the composition.

For example, a composition provided herein can include a reagent red blood cell that is characterized, at least in part, by a surface phenotype selected from:
  (i) D−, C−, E−, c−, e−;
  (ii) D+, C−, E−, c−, e−;
  (iii) D−, U−, S−, s−;
  (iv) D−, hrB−, VS+;
  (v) D−, hrB−, hrS−;
  (vi) C−, E−, c−, e−;
  (vii) D+, C−, E−, c−, e−, Go(a)+;
  (viii) D+, C−, E−, c−, e−, DAK+;
  (ix) D−, Doa−, Dob−;
  (x) Lua− b−;
  (xi) CD47; and
  (xii) any combination of two or more of the surface phenotypes of (i) to (xi).

For example, a combination can include a reagent red blood that has a surface phenotype characterized by D−, C−, E−, c−, e−, Doa− and Dob−. In some instances, a composition can include a reagent red blood that has a surface phenotype characterized by D−, C−, E−, c−, e−, Lua− and b−. In some embodiments, a composition including at least one of any of the reagent red blood cells described herein (e.g., any of the first reagent red blood cells or any of the second reagent red blood cells described herein) can include one or more of: an antibiotic (e.g., chloramphenicol, neomycin, and/or gentamycin), Immucor manufacturer diluent, adenine, adenosine, Alsever's solution, SAGM (Saline, Adenine, Glucose, Mannitol) additive solution, and dextrose In some embodiments, the compositions (e.g., pharmaceutical compositions) can be disposed in a sterile vial or tube, or a pre-loaded syringe.

In some embodiments, the compositions (e.g., pharmaceutical compositions) are formulated for different routes of administration (e.g., intravenous). In some embodiments, the compositions (e.g., pharmaceutical compositions) can include a pharmaceutically acceptable carrier (e.g., phosphate buffered saline or Ringers Lactate). Single or multiple administrations of any of the pharmaceutical compositions described herein can be given to a subject depending on, for example: the dosage and frequency as required and tolerated by the patient. A dosage of the pharmaceutical composition should provide a sufficient quantity of the selected tissue (e.g., any tissue described herein), blood product (e.g., any recombinant blood cell described herein, any reagent red blood cell described herein (e.g., any of the second reagent red blood cells described herein), or any blood product described herein) to effectively treat or ameliorate conditions, diseases, or symptoms.

Also provided herein are methods of treating a subject in need thereof (e.g., a subject having hereditary anemia, β-thalassemia, sickle cell disorder, cancer (e.g., any of the cancers described herein), trauma, or massive bleeding), that include administering a therapeutically effective amount of at least one of any of the compositions or pharmaceutical compositions provided herein.

The invention is further described in the following examples, which do not limit the scope of the invention described in the claims.

VII. EXAMPLES

The following examples are included to demonstrate embodiments of the disclosure. It should be appreciated by those of skill in the art that the techniques disclosed in the examples which follow represent techniques discovered by the inventor to function well in the practice of the disclosure, and thus can be considered to constitute modes for its practice. However, those of skill in the art should, in light of the present disclosure, appreciate that many changes can be made in the specific embodiments which are disclosed and still obtain a like or similar result without departing from the spirit and scope of the disclosure.

Example 1

RBC Alloimmunization in Patients with SCD Despite Transfusion from Rh Matched Minority Donors.

A major strategy to decrease alloimmunization in SCD is to provide RBCs matched for C, E, and K antigens. Transfusion with units from African American donors has also been suggested (Vichinsky, 2001), since extended RBC antigen profiles are more likely to be similar to patients. The inventors initiated C, E and K matching with transfusion of African American donor units through a "Blue Tag" program with the inventors' regional blood supplier in 1995. Donors self-identify as African American, a blue tag is attached to their donation, and these units are reserved for patients with SCD at two pediatric hospitals in Philadelphia (FIG. 3A) (Chou, 2012c). This program has substantially increased local African American blood donations and generates a sufficient supply of C, E, and K negative RBC units in Philadelphia.

The inventors performed a 15-year retrospective analysis to assess antigen matching for D, C, E, K and transfusion from African American donors on alloimmunization rates, antibody specificity, and clinical significance in pediatric and young adult patients with SCD (Chou, 2013 featured article in BLOOD). The study included 182 patients who received a total of 44,482 RBC units, demonstrating the tremendous resources required. Surprisingly, the inventors found 58% of 123 chronic and 15% of 59 episodically transfused patients were alloimmunized (median total RBC units transfused per patient was 230 and 3, respectively). Two-thirds of the antibodies formed were directed against the same Rh blood group antigens that were targeted for prevention (D, E, e, C, c, FIG. 3B).

Notably, the majority of Rh antibodies occurred in patients whose RBCs were phenotypically positive for the corresponding Rh antigen and would not be expected to form antibodies to a "self" antigen. For example, anti-e antibodies were identified in 16 individuals whose RBCs all typed e+ (FIG. 3C). Rh specificities were also identified in antigen-negative patients who received Rh-matched RBCs and had not been transfused elsewhere (i.e., C-patients formed anti-C antibodies despite transfusion with C− units, FIG. 3C). Overall, ⅓ of the antibodies were clinically significant with lower hemoglobin or % hemoglobin S levels than their baseline pre-transfusion values, suggestive that the patient hemolyzed the transfused RBCs (FIG. 3D).

High-resolution genotyping of RHD and RHCE revealed 87% of individuals had variant RH alleles that contributed to Rh alloimmunization (FIG. 4). Overall, greater than one-third of RHD and one-half of RHCE alleles differed from conventional sequence, and ~50% of patients had at least one variant RHD and 1 variant RHCE. While RH variants encode Rh epitopes that are likely conformational in nature, relatively small changes in part of the protein can affect the expression of epitopes in other parts of the protein or result in new epitopes (Daniels, 1998). Variant Rh epitopes are complex and D-like epitopes can be expressed on Rhce (Flegel, 2006; Chen, 2006), C-like epitopes are reported on variant RhD and Rhce proteins (Hipsky, 2012; Westhoff, 2012), and E-like antigens on RhCe proteins (Vege, 2012). These findings highlight the limitations of current Rh typing, Rh matching by serologic methods, and identification of Rh antibodies with fine specificity. Importantly, these findings have led to a change of transfusion practice for patients with SCD. The inventors have implemented DNA-based RBC typing as the primary method for extended RBC typing outside ABO and RhD and perform high resolution RHD and RHCE genotyping for all patients with SCD. Major advantages of DNA-based RBC typing is the ability to predict expression for greater than 30 antigens and identify variants that can guide antibody evaluations and choice of donor units. Ongoing collaborative efforts have included RBC genotyping in over 900 patients with SCD and ~600 African-American donors (FIG. 4) (Chou et al., 2018). While genotype matching of donors to patients is currently cost-prohibitive, it is imperative that methods are established to correctly identify antibodies during pre-transfusion testing and prevent the transfusion of incompatible donor RBCs that can result in an immune-mediated hemolytic transfusion reaction.

Genome Editing in iPSCs.

To generate iPSC-derived RBC typing reagents, the inventors will use genome editing technologies to modify genes of interest. The CRISPR/Cas9 system allows genetic manipulation in human cells with very high efficiency (reviewed in Li, 2014). The inventors have refined these technologies and have confirmed efficient genome editing in human PSCs. As an example, the creation of an RFP reporter line in the ARX locus is shown (FIG. 5A). Drug resistant clones that underwent homologous recombination were identified with an efficiency of 50% (FIG. 5B and not shown). The inventors have used the CRISPR/Cas9 system to generate insertion or deletion (indel) mutations at 10 distinct loci in human PSCs. Briefly, cells are transfected with Cas9/GFP plus the indicated guide RNA (gRNA). GFP+ cells are sorted 24 hours followed by plating at clonal density. Clones are picked and examined for indel generation at the gRNA cut site. While variability of gRNAs has been reported (Byrne, 2014; Ran, 2013), indel generation success rate is ~30% (data not shown).

Figure 18C:
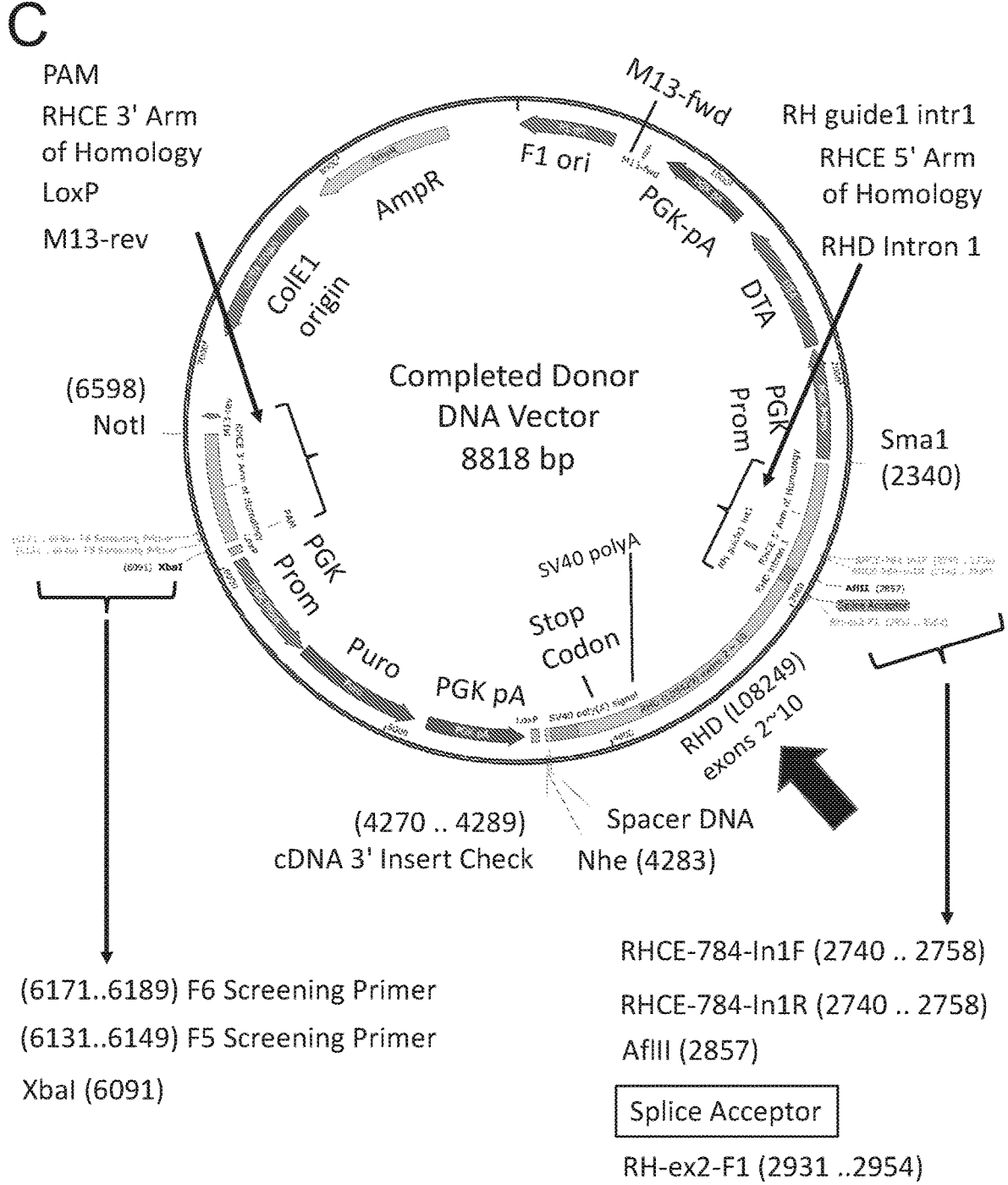

In some instances, multiple amino acid differences will be required to generate the Rh variant of interest. In these situations, the inventors will use homology directed repair with a donor DNA vector, guide RNA and CRISPR/Cas9 to generate iPSCs that will express a number of different RHD proteins including the conventional and variant antigens (FIGS. 18A-C). The inventors constructed an insert with RHD cDNA (exons 2-10 of any given variant), arms of homology, a PGK promoter, a puromycin resistance cassette and LoxP sites. The guide RNA will target intron 1 of the RHCE loci of Rh null iPSCs (generated by RHCE inactivation of a D– iPSC), which will allow use of the endogenous promoter and exon 1 of RHCE alleles (FIGS. 18A-C).

The inventors will also use ZFNs to efficiently introduce transgenes into the "safe harbor" PPP1R12C (AAVS1) locus of human PSCs (Tiyaboonchai, 2014). An example of this technology is shown in FIG. 6A in which the Gp1ba promoter was used to drive expression of the megakaryocyte transcription factor FLI-1. The Gp1ba promoter was used to drive expression of the megakaryocyte inducing transcription factor FLI-1 in this example, (FIG. 6B), but a constitutive promoter such as PGK or EF1a will be used in these studies.

Generation of Customized iPSC Lines Using Genome Editing Technologies.

Genome editing technology technologies will be used on human PSCs for the generation of rare reagent iPSC-derived RBCs for antibody identification in patients with SCD. Importantly, the iPSCs generated here are those that would be most beneficial and life saving for future transfusion. The approach is to utilize existing iPSC lines generated at CHOP which have been successfully differentiated into hematopoietic cells, and use gene editing techniques to generate a panel of renewable iPSCs that lack high prevalence antigens or that express variant Rh antigens, which is specifically relevant to patients with SCD.

Established iPSC Lines.

From the existing panel of wild-type (WT) iPSC lines generated, ABO and RHD genotyping was performed, revealing nine of the lines as Group O, the "universal" donor phenotype (lacking A and B antigens). For these studies, the inventors further characterized lines as "Rh positive" (RhD+) expressing the D antigen and "Rh negative" (RhD–) lacking the D antigen due to RHD gene deletion found in ~15% of Caucasians (Table 1.1). Of importance to remember is that the Rh proteins are encoded by two genes: RHD encodes the D antigen and RHCE encodes the CE antigens in various combinations (ce, cE, Ce, CE). In addition to Rh detection, these iPSC lines were genetically characterized for >30 clinically significant blood group antigens and high prevalence antigens using the Human Erythrocyte Antigen (HEA) genotyping platform (Casas, 2015) and other laboratory developed methods for those not determined by HEA. Table 1.1 shows the predicted antigen genotypes relevant for these studies.

TABLE 1.1

ABO and RHD genotypes of CHOP wild-type iPSC lines. RHD: PCR-multiplex analysis of exons 4, 7, and inactivating pseudogene. ABO: PCR-restriction fragment length polymorphism testing for nucleotide positions 261 (O1), 467 (A2), 703 (B) and 1096 (B, O2). Extended phenotype performed on Human Erythrocyte Antigen (HEA) genotyping platform.

| iPSC line | Method | Cell of origin | ABO genotype | RHD genotype | Predicted ABO/D type | Predicted extended antigen type by genotype |
|---|---|---|---|---|---|---|
| CHOPWT8 | Lentivirus | Peripheral blood | *01/*01 | RHD | Group O, RhD+ | C+ E– c+ e+ K– Jka+ Fya– Fyb+ S– s+ U+ Doa– Dob+ |
| CHOPWT9 | Sendai | Peripheral blood | *01/*01 | RHD | Group O, RhD+ | C– E+ c+ e– K– Jka+ Jkb+ Fya– Fyb+ S– s+ U+ Doa+ Dob+ |
| CHOPWT4 | Sendai | Fibroblast | *01/*01 | no RHD gene | Group O, RhD– | C– E– c+ e+ K– Jka– Jkb+ Fya+ Fyb– S– s+ U+ Doa+ Dob+ |
| CHOPWT10 | Sendai | Peripheral blood | *01/*01 | no RHD gene | Group O, RhD– | C– E– c+ e+ K– Jka– Jkb+ Fya+ Fyb– S– s+ U+ Doa+ Dob+ |

TABLE 1.2

Rare iPSC-derived RBC reagent panel. Used in combination with existing RBC panels, these iPSC-derived RBC reagents would facilitate rapid identification of alloantibodies and distinguish them from benign autoantibodies.

| | iPSC line | Relevant Genotype | RBC phenotype | Antibody detection |
|---|---|---|---|---|
| 1 | Rh null | No RHD, inactive RHCE | D–, C–, E–, c–, e– (no Rh antigens) | Identify antibodies against any high prevalence antigens in Rh system |
| 2 | D–– | Inactive RHCE | D–, C–, E–, c–, e– (no RhCE antigens) | Identify antibodies to RHCE |
| 3 | U–S–s– | Inactive GYB | D–, U–, S–, s– | Identify antibodies against high prevalence U antigen, and against S/s antigens |
| 4 | hrB–, VS+ | RHCE*ce(733G) | D–, hrB–, VS+ | Identify antibodies against high revalence hrB antigen ((–) reaction), or to low prevalence VS antigen ((+) reaction) |
| 5 | hrB–, hrS– | RHCE*ce(48C, 667T) | D–, hrB–, hrS– | Identify specificity antibodies against high prevalence RHCE (hrB vs hrS) antigens ((–) reaction) |

TABLE 1.2-continued

Rare iPSC-derived RBC reagent panel. Used in combination with existing RBC panels, these iPSC-derived RBC reagents would facilitate rapid identification of alloantibodies and distinguish them from benign autoantibodies.

| | iPSC line | Relevant Genotype | RBC phenotype | Antibody detection |
|---|---|---|---|---|
| 6 | Rh null Go(a)+ | RHD*DIVa on Rh-null background | D+, C-, E-, c-, e- Go(a)+ | Identify antibodies to this antigen which is unique to African Americans |
| 7 | Rh-null DAK+ | RHD*DIIIa on Rh-null background | D+, C-, E-, c-, e- DAK+ | Identify antibodies to this antigen which is unique to African Americans |
| 8 | Do null | Inactive ART | D-, Doa-, Dob- | Identify antibodies against high prevalence Do and HY antigens. Most useful as a future transfusion product. |

TABLE 1.3

Induced pluripotent stem cells (iPSC) generated by reprogramming primary human donor cells or by gene editing. PB, peripheral blood. iPSC lines were generated by reprogramming peripheral blood cells from donors with the exception of the Rh null cell lines that were generated by CRIPSR/Cas9 gene editing techniques.

| iPSC line | Cell of Origin | RHD RHCE genotype | Genotype predicted extended antigen type |
|---|---|---|---|
| r'S (hrB-, hrS+) | PB | DIIIa-CE(4-7)-D ceS DIIIa-CE(4-7)-D ceS | Group O, D-, partial C+, E-, partial c+, partial e+, K-, Jka+, Jkb-, Fya-, Fyb-, S-, s+, U-, Doa+, Dob + |
| hrs- (hrB<sup>w</sup>+) | PB | DAU0 ceMO DOL ceBI | Group O, D+, C-, E-, partial c+, partial e+, K-, Jka+, Jkb+, Fya-, Fyb-, S-, s+, U+, Doa-, Dob+ |
| V+VS+ (hrB-, hrS+) | PB | RHD ce733G RHD ce733G | Group O, D+, C-, E-, partial c+, partial e+, K-, Jka+, Jkb-, Fya-, Fyb+, S-, s+, U+, Doa-, Dob + |
| Rh null | iPSC | Disrupted RHD Disrupted RHCE | Group O, D-, C-, E-, c-, e-, K-, Jka-, Jkb+, Fya+, Fyb-, S-, s+, U+, Doa+, Dob+ |
| Lua-b- | PB | RHD Ce Deleted D ce | Group O, D+, C+, E-, c+, e+, K-, Jka+, Jkb+, Fya+, Fyb+, S-, s+, U+, Doa+, Dob+ | iPSC Line Method.

The proposed panel of customized iPSCs, listed by priority, is shown in Table 1.2. The first three lines are of highest priority because they would complement existing routine RBC reagents and allow routine hospital laboratories to rapidly distinguish clinically significant alloantibodies. The remaining lines would allow rapid identification of the fine specificity of antibodies and guide selection of compatible donors. Specific considerations include:

1. Rh null: In contrast to "Rh negative" RBCs that lack the RhD antigen only, these Rh null RBCs will lack expression of all Rh antigens. Few individuals lacking all Rh antigens are reported worldwide, and there are no Group O living blood donors in the US so these cells are not available for reagent manufacture. Individuals with Rh-null RBCs most often have mutations in the RHAG gene (Rh-associated glycoprotein). RhAG glycoprotein is required for trafficking of RhD and RhCE to the RBC membrane (Cherif-Zahar, 1996). However, lack of RhAG is associated with abnormal RBC morphology, cation defects, and mild anemia. In contrast, Rh-null RBCs also result when RhD- negative individuals, who lack RHD, have inactivating mutations in the RHCE gene. No RBC abnormalities are associated with this Rh-null genotypic background, and therefore this approach will be used to engineer Group O, Rh null cells. The Rh null iPSC-derived RBCs would be a universal reagent for identifying any Rh related antibody in patient serum, as well as a universal donor cell for transfusion.

The inventors created multiple Rh null iPSC clones from 2 WT iPSC lines: one WT line that was D+ and one WT line that was D-, by using CRISPR/Cas9 guide RNAs directed at exon 1 of RHD and/or RHCE (FIGS. 19A-B). Upon hematopoietic differentiation into mature iPSC-derived RBCs, flow cytometric analysis for cell surface Rh antigen demonstrated comparable Rh antigen expression on on RBCs from donor derived RBCs and an untargeted Rh+ parent iPSC line, while the targeted Rh null iPSCs produced RBCs showing no Rh expression on the cell surface (FIG. 19B).

2. D -/-: Rare individuals have been described who express D antigen but lack expression of RhCE (C,c, E,e) antigens due to inheritance of mutations that cause loss of expression from RHCE (Reid, 2012). This would be analogous to the "RhD negative" phenotype which is common (15% of Caucasians), but the "RhCE negative" phenotype is rare. No morphology changes or anemia is associated with this phenotype. RBCs engineered with this phenotype will allow rapid indication that a broadly reactive antibody is directed specifically to a polymorphism in RhCE antigens. The availability of these cells for future transfusion would be broad-ranging and could potentially serve patients with altered C/c or E/e antigens and parallel the usefulness seen for "RhD negative" blood usage in patients with no D antigen or altered D antigen.

3. U, S, and s antigen-negative (glycophorin B null): The absence of glycophorin B, and consequently these antigens on RBCs has a prevalence of 1% and is exclusive to people of African Black ethnicity. Hence, patients with SCD are at risk to make the antibody following routine transfusion. There are no biological consequences associated with lack of glycophorin B on RBCs, which is associated with deletion of exon 2, 4 or exon 11 in the GYPB gene. Engineered iPSCs will be generated by inactivating GYPB in iPSCs that also lack RHD to be most useful for future transfusion.

4 & 5. Negative for high prevalence antigens encoded by RHCE: These cells would distinguish the fine specificity of antibodies directed to RHCE proteins, and facilitate improved donor RBC selection. Table 1.3 shows three lines generated by reprogramming rare or unusual donor cells, that have subsequently been differentiated into red blood cells and express their genotype predicted red cell Rh antigen phenotype.

6 & 7. Positive for low prevalence antigens on RhD exclusive to African Blacks: These cells would express engineered D-epitopes uniquely found only in African Americans important for distinguishing fine specificity of antibodies directed to RhD. The availability of these engineered cells would improve donor RBC selection by expanding the potential compatible units, as currently patients who make these antibodies receive RhD negative blood, which primarily comes from Caucasian donors and exposes patients to additional antigenic mismatches in other blood group systems.

8. Dombrock (Do) null: RBCs lacking expression of Dombrock protein, encoded by the ART gene, have been infrequently described and are associated with several molecular mutations including skipping of exon 2. The function of this ADP-ribosyltransferase on RBCs is not known, but rare patients whose RBCs lack the protein do not have compromised RBC survival (Gubin, 2000). Antibodies to Doa/b allelic antigens are notorious for causing severe life-threatening transfusion reactions (Lomas-Francis, 2010).

The Group O, RhD− lines will be used to generate customized iPSCs with the exception of the D −/− line, for which the inventors will also use the Group O, RhD+ lines (Table 1.1). The inventors will design guide RNAs (gRNAs, crispr.mit.edu), screen for efficiency to RHD, RHCE, GYB, and ART, and transfect with Cas9/GFP as described in preliminary data (FIGS. 5A-C). They have initiated this work and successfully identified multiple clones with RHCE disrupted for production of true Rh "null" iPSC lines (FIGS. 19A-B, Table 1.3). Since determination of antibody specificity absolutely requires no reactivity to RBCs that lack the offending antigen, Rh-null iPSC-derived RBCs are essential for antibody identification against high prevalence or variant Rh antigens. Combining testing using Rh-null and D−− iPSC-derived RBCs, that express D but no RHCE antigens, the anti-RhCE vs anti-D specificities to high prevalence antigens will readily be distinguished in hospital blood banks.

Figure 7:
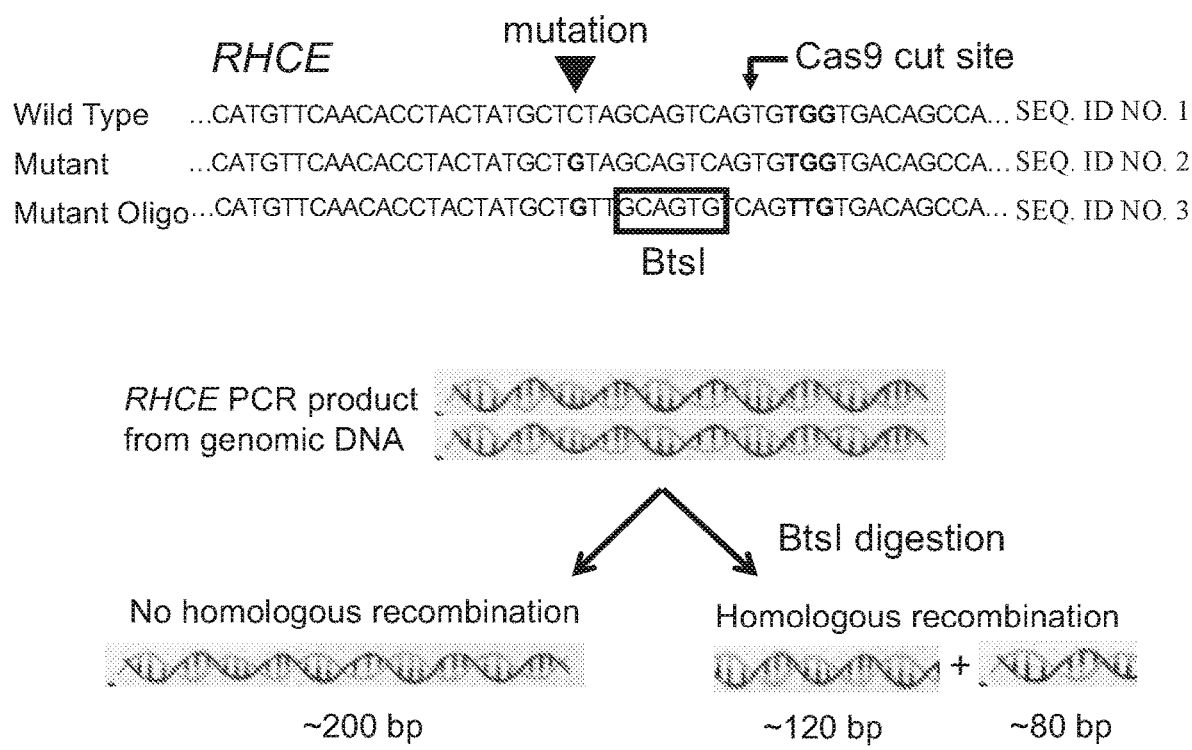
FIG. 7. CRISPR/Cas9 gene editing strategy to mutate RHCE by homologous recombination. Guide RNAs target a sequence close to the desired mutation site. If mutant oligonucleotide sequence is introduced, restriction enzyme digestion results in two fragments. Sequences are, from top to bottom, SEQ ID NOS: 1, 2 and 3. GRCh38.p 12 accession number is GCA_000001405.27. RefSeq assembly number is GCA_000001405.3.
Figure 12:
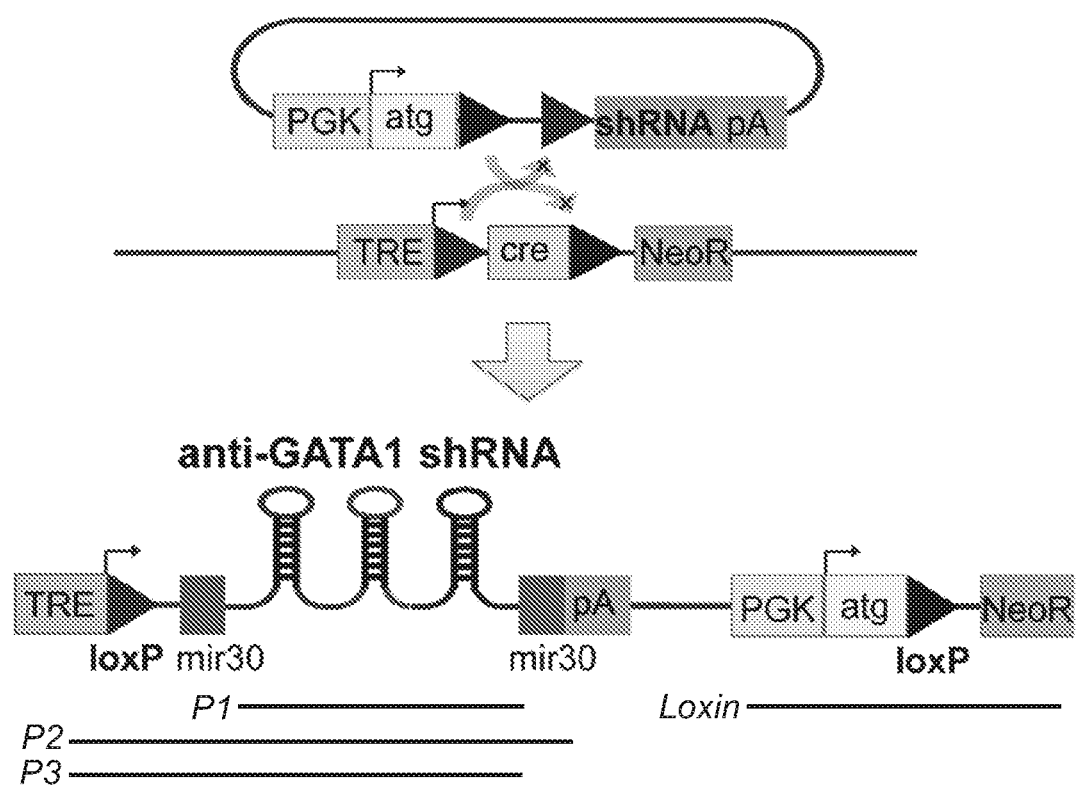
FIG. 12. ESCs expressing doxycycline-regulated Gata1 shRNAs. Top: targeting vector. Middle: modified Hprt locus in A2lox.cre parental ESCs. Bottom: the modified locus after cre-mediated recombination. Gata1 or control shRNAs flanked by Mir 30 processing sequences are regulated by tet response element (TRE). P1-P3 and loxin are PCR products used to assess the modified locus.
Figure 15:
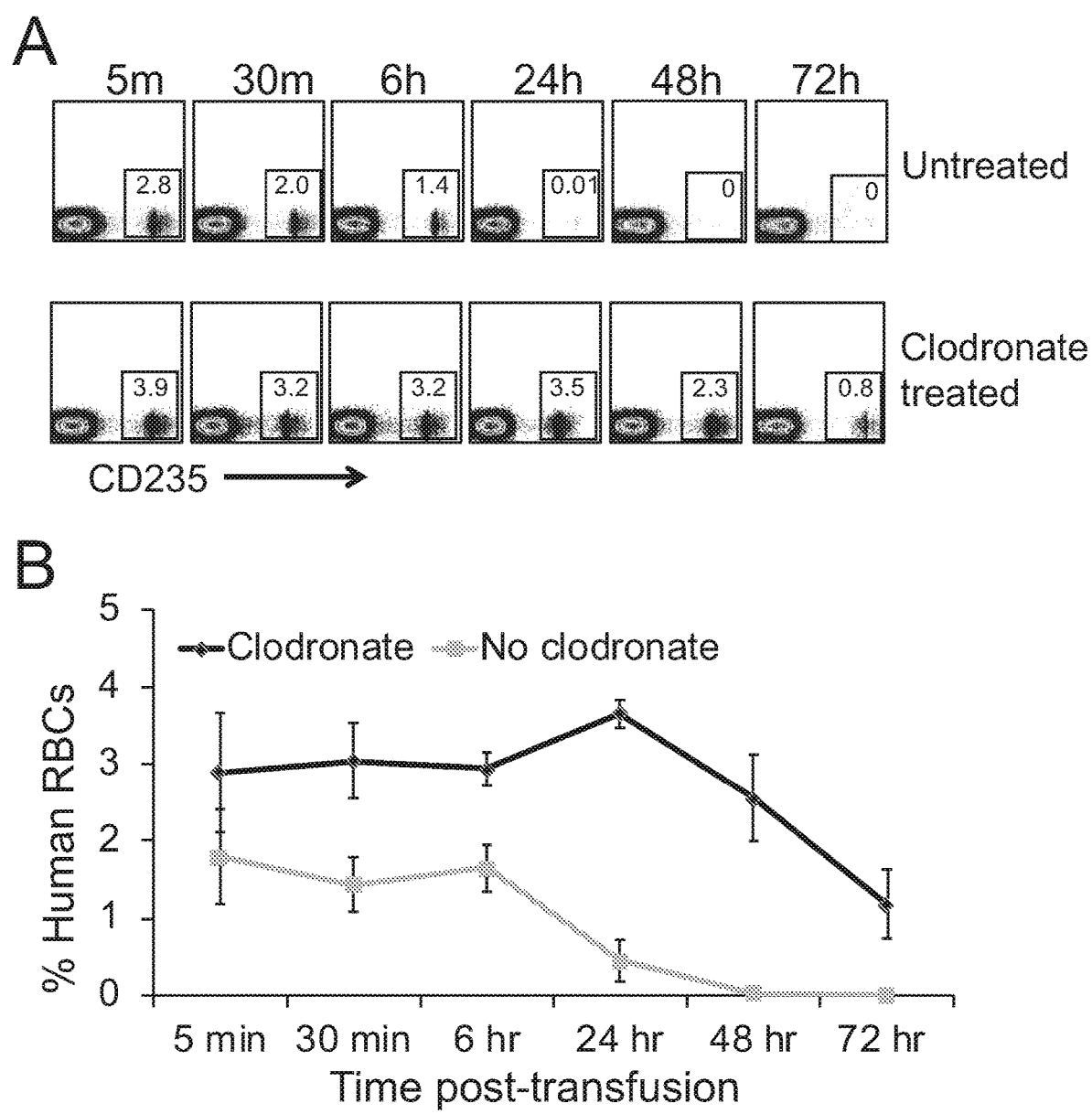
FIGS. 15A-B. Human donor RBC survival in immunodeficient mice with and without Clodronate pre-infusion. A. Representative FACS analysis of peripheral blood of untreated vs Clodronated treated mouse after indicated time from RBC transfusion. B. Average % circulating human RBCs post-transfusion mouse peripheral blood. N=3 for each group.
Figure 16:
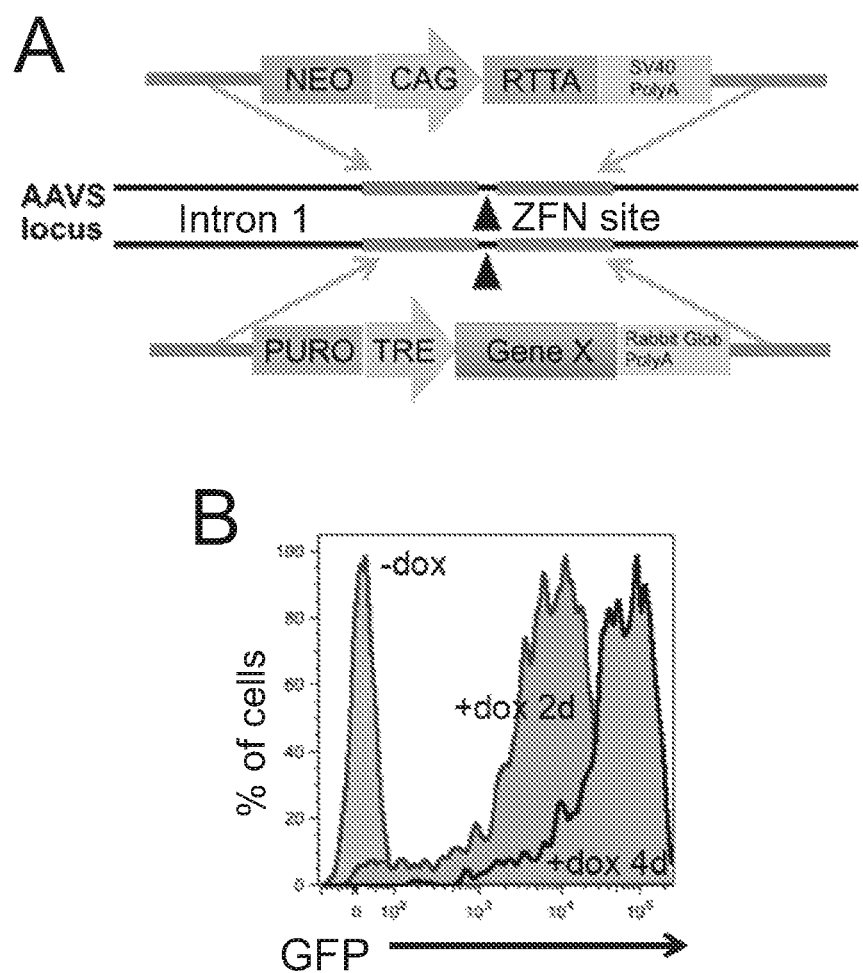
FIGS. 16A-B. Dox-inducible GFP expression in human ESCs.

Reagent iPSC-derived RBCs expressing variant RH antigens will allow identification of the fine specificity of Rh antibodies. To generate lines that lack the high prevalence RhCE antigens hrB and hrS, the inventors will reprogram rare or uncommon donors, and use the CRISPR/Cas 9 technology to generate mutations found in patients: RHCE*ce(733G) and RHCE*ce(48C, 667T) (aka RHce*ceMO) (FIG. 4). Simultaneous transient transfection of Cas9/GFP with gRNAs designed to target a sequence in close proximity to the desired mutation site, and an ~200 bp oligonucleotide with the mutant sequence will be used (FIG. 7). The inventors will screen for clones that are homozygous for the mutations. Single nucleotide mutations have been successfully made by introducing mutant oligonucleotides via CRISPR/Cas9 technique into the SETBP1 gene with 7% efficiency for homozygous mutant clones (not shown). Alternatively, they will use homologous directed repair with the strategy in FIGS. 18A-C.

The true Rh null iPSC lines will be used to generate lines 6 and 7 (Table 1.2) to exclusively express the variant RhD antigens Go(a) and DAK. These Rh variants result from multiple mutations in different exons, and therefore are less amenable to genome editing by CRISPR/Cas methods. Individuals expressing DAK carry a RHD*DIIIa allele that encodes 5 amino acid changes (FIG. 4) and individuals expressing Go(a+) carry a RHD*DIVa allele that encodes 4 amino acid changes. The mutant cDNAs for these RhD variant antigens will be expressed as transgenes in the "safe harbor" PPP1R12C (AAVS1) locus using the ZFN technology, as described in Preliminary data (FIG. 6), or inserted into the endogenous RHCE locus (FIGS. 18A-C). The latter strategy takes advantage of the identical sequences of exon 1 in both RHD and RHCE alleles. A D− line was used to knockout RHCE expression via a mutation resulting in an early stop codon, and the variant RHD or RHCE cDNA can be inserted using homology directed repair with a guide targeted to RHCE intron 1. These reagent iPSC− derived RBCs will be used to determine the fine specificity of unexplained Rh antibodies that occur in patients despite receiving "Rh-matched" blood.

Hematopoietic differentiation of the customized iPSCs produced will be performed according to standard protocols to generate hematopoietic progenitors (Chou, 2012; Byrska-Bishop, 2015). A 2-step production protocol in defined, serum-free media with appropriate combinations of cytokines will be used to differentiate iPSCs into iPSC-derived RBCs: (1) embryoid body or adherent culture of undifferentiated iPSCs into hematopoietic progenitors, and (2) differentiation of hematopoietic progenitors into erythroid cells, and their amplification to generate iPSC-derived RBCs. Day 7-9 hematopoietic progenitor cells (HPCs) are propagated in liquid conditions using SCF, EPO, and holotransferrin to obtain a synchronized population of CD71+ (transferrin receptor) and CD235+ (glycophorin A) iPSC-derived RBCs (FIGS. 8A-B). The mature iPSC-derived RBCs express similar cell surface markers compared to donor RBCs, and are smaller and more morphologically mature (condensed nuclei, mature cytoplasm) than RBCs generated by current protocols for differentiation of RBCs from iPSCs. Ongoing work by the inventors aim to establish culture conditions to generate iPSC-derived RBCs that are developmentally similar to red cells found in the latter part of fetal gestation or postnatally, whereas current protocols generate red cells found in a first trimester fetus (FIGS. 10A-C). This is relevant for RBC antigen expression and the goal to have cells from different developmental stages (embryonic, fetal, adult) since this could provide antigen negative and antigen positive cells.

The HPCs can be cryopreserved and differentiated into iPSC-derived RBCs when needed. During iPSC-derived RBC differentiation, maximal expansion occurs by days 12-14 of culture. Myeloid cells may interfere with agglutination studies, so cultures can be sorted to enrich for RBCs that comprise 80-85% of the culture. However, the inventors have developed culture conditions such that >95% of cells are mature iPSC-derived RBCs (FIGS. 8A-B), and thus this final enrichment step may not be required if the proportion of myeloid cells are consistently low and thus do not interfere with agglutination testing. Each undifferentiated iPSC gives rise to 2-10 iPSC progenitor cells, which subsequently yields up to 300 iPSC− derived RBCs per progenitor cell, such that one 6 well tissue culture plate of undifferentiated iPSCs ultimately produces over $10^8$ iPSC-derived RBCs by day 12 of erythroid culture which is sufficient for characterization and can undergo scale up for clinical application.

Figure 25:
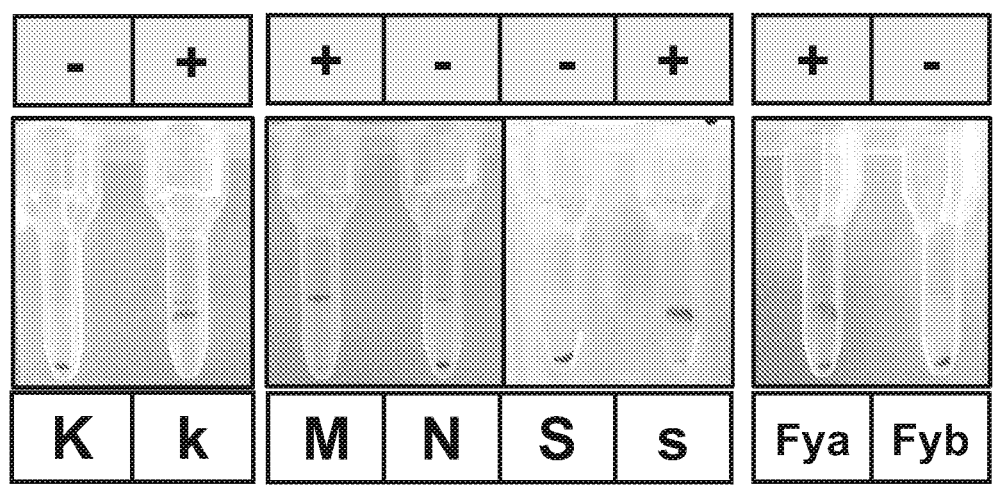
FIG. 25. Serologic typing of iPSC-derived red blood cells for non-Rh antigens. Using monoclonal typing reagents for K, k, M, N, S, S, Fya, and Fyb, typing was performed with 500,000 iRBCs per gel card assay column. +/− indicates antigen phenotype as predicted by blood group genotype. iPSC-derived RBCs agglutinated and remained at the top of the gel matrix when the antigen was predicted to be expressed (+) and did not agglutinate and pelleted to bottom of column when antigen was predicted to be absent (−).

Human ESC-derived RBCs are known to express RhD antigen (Lu, 2008), but expression of other blood group antigens has not been established. Blood group antigen characterization was performed by flow cytometry, qPCR, and with commercial antibody reagents as well as polyclonal and single source sera from NYBC collections (FIG. 25). NYBC has a large number of monoclonal antibodies to monitor protein expression profiles and epitopes. RBC agglutination of iPSC-derived RBCs with these antibody reagents will be tested by three common agglutination methods: tube, gel card and solid phase microplate. Initial studies will be performed on the primitive, yolk-sac type iPSC-derived RBCs generated with current protocols, and subsequently on definitive iPSC-derived RBCs produced. The inventors will also screen for neoantigens which are a concern for iPSC-derived RBCs that may express embryonic, fetal or new proteins that might be antigenic. These new antigens would not be detected by testing with blood group antibodies but may be identified by screening with pools of human sera from donors who might have encountered these and made natural antibodies.

Since gel card methods require fewer cells than tube methods, the goal was to optimize iPSC-derived RBCs for this assay. Optimization of iPSC-derived RBCs for antibody identification was performed first on parental iPSC lines by typing for blood group antigens determined by genotyping to be expressed on the RBC membrane (Table 1.1). The inventors demonstrated that only 500 K cells was more than sufficient to visualize RBCs for macroscopic interpretation of commercial gel card assays (FIGS. 9A-C). Non-agglutinated RBCs pelleted at the bottom of the column and agglutinated RBCs remained at the top of the column after centrifugation.

Using monoclonal Rh typing reagents for D, C, c, E, and e, typing was performed with 500,000 iPSC-derived RBCs per gel card assay column. FIGS. 9A-C demonstrate Rh typing for the untargeted D− wild type (WT) iPSC-derived RBCs, the untargeted D+ WT iPSC-derived RBCs, and the CRISPR-targeted Rh null iPSC-derived RBCs. The inventors show that iPSC− derived RBCs agglutinated and remained at the top of the gel matrix when the antigen was predicted to be expressed (+) and did not agglutinate and pelleted to bottom of column when antigen was predicted to be absent (−). The Rh null cells did not react with monoclonal antibodies against the five principal Rh antigens. In addition to the gel card assay, RBC agglutination will be assessed by performing the tube method and viewed microscopically for agglutination, or in 96 well assays in which 1e6 cells are incubated at 37° C. with antibody and assessed microscopically (Kim, 2015) or using any of the other exemplary arrays, assays, or kits described herein.

Since antibodies in patient plasma or serum can have varying titers and would likely be lower titer than the monoclonal typing reagents, the inventors tested antibody screening with iPSC-derived RBCs against patient serum containing known antibodies (FIGS. 21A-B). Two examples are shown. First, patient serum containing anti-e was reacted with donor derived panel red cells or iPSC-derived RBCs in the gel card assay and showed agglutination with e+ donor derived RBCs and e+ iPSC-derived RBCs. Conversely, no agglutination occurred with donor derived e− RBCs or iPSC-derived RBCs, consistent with an anti-e antibody present in the patient's serum. Second, the inventors tested the iPSC-derived RBCs with patient serum containing anti-hrS, an antibody to a high prevalence antigen which is often mistaken as a warm autoantibody due to lack of appropriate reagent RBCs. Patient serum was reacted with donor derived panel red cells or iPSC-derived RBCs in the gel card assay and showed agglutination with all hrS+ cells and no agglutination with all hrS− cells.

Commercial RBC reagents manufactured from donor RBCs are provided as suspensions in buffered preservative solution and have a 4-6 week shelf life. Several storage solutions have been tested for iPSC-derived RBC compatibility with gel column assays and will be tested for storage. These diluents contain adenine and adenosine to prevent hemolysis and preserve antigenicity, as well as antibiotics to prevent bacterial contamination. iPSC− derived RBCs can be suspended at a concentration of 200,000 and 400,000 cells/microliter, equivalent to commercial RBC suspensions respectively, but the inventors will optimize cell numbers for the different antibody identification techniques used by hospital blood banks. The inventors will test storage stability and validate performance of reagent iPSC-derived RBCs. Commercial reagent RBCs are expected to perform as indicated on the manufacturer package insert and there is no U.S. standard of potency. They will determine storage stability by maintenance of pH between 5 and 6, measurement of free hemoglobin to assess for hemolysis, and cell morphology assessed by cytospin preparations every 7 days. Maintenance of antigenicity will be measured by agglutination studies as described above every 7 days and suitable performance will be defined as not more than one grade agglutination difference (i.e., 2+ vs 3+) and with no unexpected reactivity.

Example 2

Sources of Cells that can be Used to Produce cRBCs and Enucleation.

RBC production starts during the $6^{th}$ weeks of gestation and continues throughout life. Three types of RBCs are successively produced during development: primitive RBCs that express embryonic hemoglobins (Hb) ($\zeta_2\varepsilon_2$, $\alpha_2\varepsilon_2$, $\zeta_2\gamma_2$), fetal RBCs that express mostly Hb F ($\alpha_2\gamma_2$) and some adult Hbs ($\alpha_2\beta_2$, $\alpha_2\gamma_2$), and adult RBCs that express mostly adult Hbs and some Hb F. The precursors of all of these cells can theoretically be used as source of cells but the field has focused on cord blood (CB) and circulating peripheral blood (PB) hematopoietic stem cells (HSCs), and hematopoietic progenitors cells (HPCs) because they are more readily available. More recently, induced pluripotent stem cells (iPSCs) have emerged as an additional source of cells to produce cRBCs. CB HSCs/HPCs have been studied extensively because they are more proliferative than PB cells but there are no available resources from which one could obtain CB HSCs/HPCs carrying rare blood groups.

One of the first methods to produce cRBCs in liquid culture was developed by Fibach and colleagues who described a two-step procedure designed to first amplify and then favor the maturation of erythroid progenitors present in umbilical cord and adult peripheral blood (Fibach et al., *Blood* 73: 100-103, 1989). While this method was effective for the production of erythroid precursors, it did not yield large amounts of enucleated cRBCs and required serum and conditioned medium. Subsequently a variety of methods were developed that improved on this protocol (Freyssinier et al., *Br. J. Haematol.* 106: 912-922, 1999) and Panzenbock et al., *Blood* 92: 3658-3668, 1998). The Douay group has made significant contributions by developing methods to amplify CB and PB HSCs/HPCs using completely defined conditions (Giarratana et al., *Nat. Biotechnol.* 23: 69-74, 2005; and Douay et al., *Nat. Biotechnol.* 23: 69-74, 2005). cRBCs produced from CB using these methods express close to 100% Hb F while those produce from PB HSCs/HPCs express 10-20% Hb F and 80-90% Hb A.

Other important contributions were made over the last 20 years by the Beug group and others who have developed an erythroblast-expansion cocktail containing stem cell factor (SCF), erythropoietin (EPO), and dexamethasone (SED) to induce extensive proliferation of late progenitors and erythroblasts that can differentiate into cells resembling stress reticulocytes (Leberbauer et al., *Blood* 105:85-94, 2005; Dolznig et al., *Methods Mol. Med.* 105: 323-344, 2005; and Carotta et al., *Blood* 104:1873-1880, 2004). cRBCs produced from adult progenitors using the erythroblast expansion cocktail express 30-60% Hb F and 40-70% Hb A.

The present inventors expanded on the studies using hESCs co-cultured on a feeder layer of S17 cells (Kaufman et al., *Proc. Natl. Acad. Sci. U.S.A.* 98:10716-10721, 2001) by identifying FHB-hTERT as a more efficient feeder layer and by showing that hESC differentiation toward the erythroid lineage closely parallels normal human early embryonic development (Croizat et al., *Acta Haematol.* 102: 172-179, 1999; Olivier et al., *Exp. Hematol.* 34: 1635-1642, 2006; Qiu et al., *Exp. Hematol.* 33:1450-1458, 2005; and Qiu et al., *Blood* 111:2400-2408, 2008). The latter point was demonstrated by a detailed analysis of the expression of the α- and β-like globin genes at the mRNA and protein levels that revealed that it was possible to induce hESCs to differentiate into cRBCs containing Hb Gower 1, Hb Gower 2, and Hb F with the same temporal sequence than during normal development.

Several labs have attempted to develop procedures to expand long-term repopulating HSCs in culture because of their importance for transplantation applications (Sorrentino, *Nat. Rev. Immunol.* 4: 878-888, 2004). Zhang and colleagues have developed a procedure based on the "STIF" cytokine cocktail (stem cell factor (SCF), thrombopoietin (TPO), insulin-like growth factor 2 (IGF2), and fibroblast growth factor-2 (FGF2)) and angiopoietin-like proteins to expand HSCs about 20-fold (Zhang et al., *Blood* 111:3415-3423, 2008) and Zhang et al., *Nat. Med.* 12: 240-245, 2006). More recently, Boitano and colleagues demonstrated a 50-fold HSC expansion using an aryl hydrocarbon receptor antagonist (Boitano et al., *Science* 329: 1345-1348, 2010).

Maximal expansion of circulating stem and progenitor cells can theoretically be obtained by successively amplifying the stem cell compartment, the progenitor compartment, and the erythroblast compartment (see, e.g., FIGS. 23A-B) (Olivier et al., *Stem Cell Transl. Med.* 1:604-614, 2012).

Pulsing CD34$^+$ cells in HPC-expansion medium for 48 hours prior to incubation in the HSC-expansion medium significantly increased yield. In brief, incubation for one week in the HSC-expansion medium increased the yield of cRBCs about 15-fold relative to direct incubation in HPC-expansion medium but pulsing the cells for 48 hours in HPC-expansion medium prior to incubation in HSC-expansion medium for 5 days increased the yield an additional 5- to 20-fold (FIGS. 23C-E).

Longer incubation in HSC-expansion medium (with or without the pulse) resulted in continued increase in the number of CD34$^+$38$^-$ cells but not in cRBCs yield (Olivier et al., *Stem Cell Transl. Med.* 1:604-614, 2012), suggesting that the expanding cells were losing erythroid potential. To determine if these cells could be redirected toward the erythroid lineage, we introduced periodic 48-hour pulses in HPC-expansion medium during long incubation in HSC-expansion medium. After three cycles of this regimen (2 days in HPC-expansion, 5 days in HSC-expansion) followed by 1 week in HPC-expansion and 1 week in E-differentiation the overall yield of cRBCs obtained from CB CD34$^+$ cells was increased another 15- to 20-fold leading to a theoretical overall yield of about $2\times10^7$ cRBCs/CD34$^+$ cell (FIG. 23E).

The mechanisms by which periodic priming with the HPC-expansion medium increase the yield of cRBCs in these cultures is not known but several studies have shown that in vivo there is a hierarchy of HSCs that are more or less biased towards the myeloid or lymphoid lineages (Babovic et al., *Exp. Cell Res.* 329: 185-191, 2014). This suggests that periodically priming cells HSC/HPC growing and self-renewing in HSC-expansion conditions might preserve their myeloid potentials and prevent the acquisition of a lymphoid bias. To start testing this hypothesis, HSCs (Lin$^-$34$^+$38$^-$90$^+$49f$^+$ cells), MPP(Lin$^-$34$^+$38$^-$), and CMP(Lin$^-$34$^+$38$^+$45RA$^-$123$^{low}$) were sorted and cultured in HSC-expansion medium with or without a pulse. This revealed that pulsing increased the number of cRBCs produced by all cell fractions but that the effect of the pulse was more pronounced on HSCs and MPPs (data not shown).

As described above, provided herein are novel methods of amplification of CB HSCs/HPCs, based on combining HSC- and HPC-expansion conditions, that yielded an average of up to $2\times10^7$ cRBC/CD34$^+$ cells (FIGS. 23A-G). To determine which of the HPC− expansion cytokines (SCF, FLT3-L, IL3, BMP4, IL11, and Epo) are required for the pulse-induced expansion, experiments in which individual and combination of cytokines were systematically omitted were performed. The inventors showed that cells produced in erythroid culture could be frozen and thawed at multiple time point during the procedure with minimal effects on yield. Cells were frozen at different time points to expedite these experiments.

In addition to measuring the yield of cRBCs, the cultures were monitored weekly by colony assays to assess the erythroid and myeloid output and by HPLC to assess the type of hemoglobin produced. The 86mmune-phenotype of the cells in the culture were monitored weekly to determine if cells growing in these conditions for extended period of times had characteristics of HSC, CMP, MEP, or BFUE. The identification was confirmed by performing RNA-sequencing experiments and comparing the profiles with published profiles of hematopoietic stem and progenitor cells.

Because there were no known major surface antigen changes between orthochromatic erythroblasts and enucleated cells, it was also determined whether nucleated erythroblasts can be used as reagent red blood cells.

Enucleation.

The first reported method to induce enucleation of cultured erythroblasts relied on a feeder layer (Giarratana et al., *Nat. Biotechnol.* 23: 69-74, 2005). More recently, Miharada et al. (*Nat. Biotechnol.* 24:1255-1256, 2006) developed culture conditions in which enucleation occurred without feeder. Both approaches yielded similar enucleation rates (data not shown). Importantly, these results suggested that it was possible to obtain close to 100% enucleation with either protocol when PB cells were cultured with the Olivier procedure, but that the enucleation rate was lower when the erythroblasts expansion procedure was used or when iPSCs were the source of the cells.

Generation of iPSCs from with Rare Red Cell Phenotypes.

iPSCs with the red blood cell phenotypes identified in Table 1.4 were produced. iPSCs were differentiated into CD34$^+$ cells using a chemically-defined EB formation system that was modified from the spin-EB method (Ng et al., Blood 106:1601-1603, 2005). The same liquid culture methods could generally be used to expand CD34+ hematopoietic cells regardless of their sources (Olivier et al., *Stem Cell Transl. Med.* 1:604-614, 2012). CD34+CD38− hematopoietic cells were used as the source of cells and plasmid nucleofection was used because it was performed in GMP conditions using an electroporation buffer that was made entirely of inorganic reagents and was easily made under GMP conditions. The iPSCs were grown in E8 medium on vitronectin (Chen et al., *Nat. Methods* 8:424-429, 2011). All of the components of the culture system were commercially available in USP or GMP grade.

The quality of the iPSCs was validated using a protocol which included fluorescence-activated cell sorting (FACS) analysis for expression of SSEA-3, SSEA-4, TRA-1-60, and TRA-1-80, and demonstration of pluripotency by teratoma formation in NSG mice and by embryoid body (EB) formation.

The major difference between PB and iPSC-derived cRBCs was that the latter cells had an embryonic/fetal phenotype and are a renewal cell source. Because many antigens were not developmentally regulated, this might not have preclude the use of iPSCs for the production cRBCs for use as reagent cRBCs or for transfusion. About $10^4$ cRBCs per PSC-derived CD34+ cells were produced using the Olivier procedure (FIGS. 23C-E) and more than $1.5 \times 10^5$ CD34+ cells could be generated per 6-well plate of ESCs (about $5 \times 10^6$ cells) using a differentiation system based on co-culture with FHB-hTert cells (Olivier et al., *Exp. Hematol.* 34:1635-1642, 2006; Qiu et al., *Exp. Hematol.* 33L: 1450-1458, 2005; and Olivier et al., *Stem Cell Transl. Med.* 1:604-614, 2012). Using similar PSC-derived CD34+ cells, very large amounts of primitive basophilic erythroblasts expressing a mixture of embryonic and fetal Hb were generated using the erythroblast expansion procedure (FIG. 23G). This result was confirmed by the existence of erythroblasts that can be expanded expands nearly indefinitely in the mouse yolk-sac (England et al., *Blood* 117:2708-2717, 2011). Either the Olivier or the erythroblast-expansion approaches could therefore yield more than $10^9$ cRBCs per plate of PSCs.

Alternatively, erythroid progenitors could be immortalized either by transduction with Sox2, c-Myc, and anti-p53 (Huang et al., *Mol. Ther.* 22:452-463, 2014) or via transduction with Tal1 and HPV16-E6/E7 cells (Kurita et al., *PLoS One* 8: e59890, 2013). Both methods immortalized erythroid progenitors in a manner that preserved their ability to terminally differentiate.

Methods to differentiate iPSCs with more adult phenotypes have also been developed (Peraki et al., *Mol. Cell Biol.* 37(19): e00183-17, 2017).

Generation of O—Rh-null iPSCs. Group O, Rh-null cells, which have been dubbed "universal cells" for transfusion, were useful as reagent RBCs because they could be used to rule out the presence of any Rh related antibody in the serum of the patient, and could also be useful as universal donor cells for transfusion.

The main Rh antigens are D, C, E, c, and e, which are encoded by two adjacent gene loci, RHD (which codes for the D antigen and whose absence results in the Rh negative phenotype) and the RHCE gene (which codes for the C, E, c, and e antigens). RBCs can be Rh-null because they lack expression of both the RhD and RhCE, or because they lack expression of the RHAG gene, which encodes a protein that forms a complex with the product of the RHD and RHCE genes. It has recently been shown that RhAG is important for cation balance in RBCs. RBCs from individuals that lack expression of RhAG exhibit stomatocytosis and have cation defects. Hence, Rh-null cells that carry deletions of RhAG are not useful as reagents or for transfusion. Patients with deletions of both the RHCE and RHD also have Rh-null red cells, but express RhAG protein in reduced amounts. These are extremely rare and the defect, if any, of the red blood cells has not been studied. Rh-null RBCs, which lacked RhCE and RhD, but had functional RhAG, were generated.

Site-specific mutagenesis in iPSCs was performed using the CRISPR/cas9 technology to disrupt expression of the RHCE genes in group O, RhD− iPSCs. Donors with this group O RhD negative phenotype were readily available. To disrupt expression of RHCE, guide RNA were designed that targeted the first or second exon of the RHCE gene and were screened for clones in which repair by non-homologous-end-joining had resulted in the introduction of a stop codon. iPSCs were first transduced with an inducible Cas9 (e.g., a doxycycline-inducible Cas9) and guide RNA vectors and successfully transduced clones were selected using antibiotics. Expression of the Cas9 protein was then induced with an agent (e.g., doxycycline) and clones in which mutations were introduced were screened by PCR.

Maturation and Physical Characterization of cRBCs.

The morphology and maturation of cRBCs was determined by Giemsa staining. Synthesis of Hb was assessed by high performance liquid chromatography (HPLC). The maturation state of cRBCs was also monitored by measurement of levels of CD235a, CD36, and/or CD71 expression by flow cytometry. Glucose-6-phosphate dehydrogenase (G6PD) and pyruvate kinase (PK) levels were measured as described in (Jansen et al., *Am. J. Hematol.* 20: 203-215, 1985).

Membrane deformability and protein linkage to the cytoskeleton were measured (Dahl et al., *Blood* 103:1131-1136, 2004; and Dahl et al., *Blood* 101:1194-1199, 2003). These studies included membrane deformability measured by micropipette aspiration and measurement of the linkage of integral proteins to the cytoskeleton by fluorescent image microdeformation (FIMD). G6PD levels and PK levels were similar to those seen in young erythrocytes, and that the FIMD experiments provided insights into membrane and storage stability.

Commercial red cell reagents have a 4-6 week shelf life, however, the actual outdate is 67 days from the day blood is withdrawn from the donor. Storage stability measurements determined the "outdate" of the cRBC product. Stability was assessed using routine blood bank tests and maintenance of antigenicity was measured every 5-7 days.

Commercial reagent red cells were provided as 2-4% suspensions in buffered preservative solution. Two storage solutions were tested. cRBCs were suspended at 2-4% concentration in Immucor manufacturer diluent, which was provided with each set of panel cells received (and available in excess quantities in the reference laboratory). This diluent solution contained adenine and adenosine to retard hemolysis and loss of antigenicity, and chloramphenicol (0.25 mg/ml), neomycin sulfate (0.1 mg/ml), and gentamycin sulfate (0.05 mg/ml) to mitigate bacterial contamination. Cells were also suspended in Alsever's Solution (Sigma) which permitted storage of RBCs for approximately 10 weeks and was composed of an equal volume of 2.05% dextrose, 0.8% sodium citrate, 0.055% citric acid, and 0.42% sodium chloride. cRBCs and primary RBCs from the donor as control were stored at 1-10° C., with measurement of hemolysis as free hemoglobin and pH, and the cells were observed for morphology and performance every 5-7 days.

Additional RBC storage solutions and additives, including those found to improve donor RBC storage (SAGM, MAP) were described in Fung et al., AABB Technical Manual, Eighteenth Edition, p 138.

Equivalent performance was defined as not more than one grade difference (e.g., 3+ vs. 4+) in agglutination reactions and no unexpected reactivity. Minimal hemolysis (<5%) was seen at 6 weeks, and pH was maintained between pH 5-6. The presence of a bacteriostatic agent was needed to prevent bacterial contamination. Storage in dextrose offered additional longevity. The pH of storage medium was reported to affect the rate of antigen deterioration, specifically low pH and low ionic strength.

Phenotypic and Genotypic Characterization of cRBCs.

The expression of clinically relevant RBC antigens was determined by genetic polymorphisms in genes that were often regulated during differentiation. Comparison of blood group antigen expression on cRBCs compared to primary RBCs from rare blood donors provided indications on which cell sources were appropriate for the reagent cRBCs application and for transfusion. Enucleation rates in culture varied significantly between sources of cells. Culture methods were one of the major determinants of overall cell yield. Antigen profiles of enucleated cRBCs were compared with that of basophilic and orthochromatic erythroblasts to determine if red cell precursors could be used as reagent RBCs. Blood group antigens were encoded throughout the human genome and many antigens were present in protein complexes.

Figure 24:
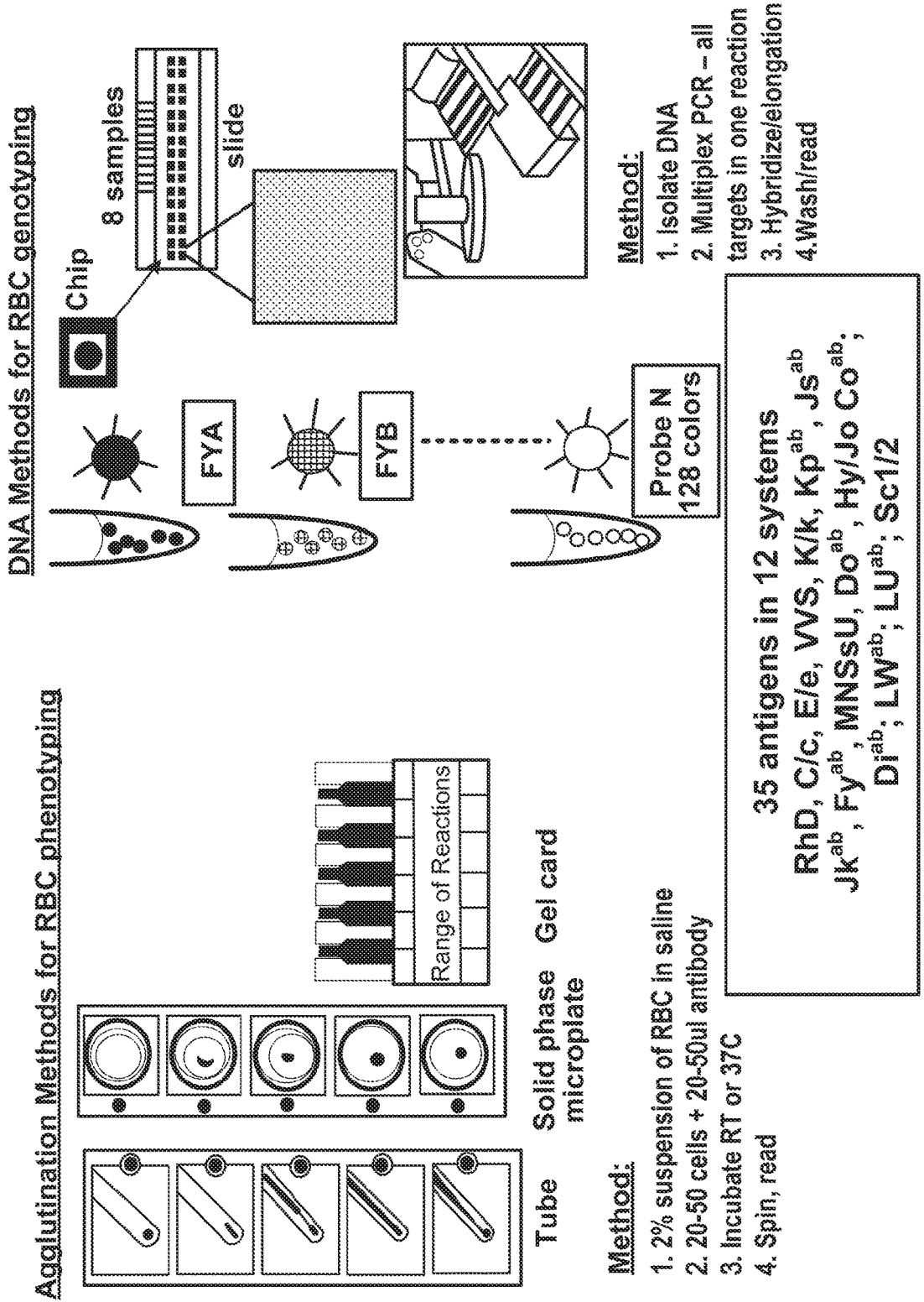
FIG. 24. Schematic summary of exemplary methods that can be used to type cRBCs and erythroid precursors.

The cRBCs produced as described above in Example 2 were compared with native cells from the donors which were stored frozen in liquid nitrogen by routinely used methods. Experiments are performed with enucleated cells and with precursors. FIG. 24 summarized the serologic and molecular FDA-licensed methods and techniques that were used to characterize the cRBCs, as well as laboratory developed tests (LDTs) using serologic reagents and molecular methods including gene sequencing.

Serologic Typing for Blood Group Antigens.

Testing was performed by standard tube methods with commercial reagents and polyclonal and single source sera from our collections. Supernatant fluids containing monoclonal antibodies that were specific for the blood groups in Table 2 were also used.

TABLE 2

Blood Group Systems for Testing Genetic Changes

| System name | # of antigens | Gene names | chromosomal. location |
|---|---|---|---|
| ABO | 4 | ABO | 9q34.2 |
| MNS | 46 | GYPA, GYPB | 4q31.21 |
| Rh | 52 | RHD, RHCE | 1p36.11 |
| Lutheran | 20 | LU, BCAM | 19q13.32 |
| Kell | 34 | KEL | 7q34 |
| Duffy | 5 | FY, DARC | 1q23.2 |
| Kidd | 3 | JK, SLC14A1 | 18q12.3 |
| Diego | 22 | DI, SLC4A1 | 17q21.31 |
| Yt | 2 | YT, ACHE | 7q22.1 |
| Scianna | 7 | SC, ERMAP | 1p34.2 |
| Dombrock | 8 | DO, ART4 | 12p12.3 |
| Colton | 4 | CO, AQP1 | 7p14.3 |
| Landsteiner-Wiener | 3 | LW, ICAM4 | 19p13.2 |
| RhAG | 4 | RHAG | 6p12.3 |
| JR | 1 | JR, ABCG2 | 4q22.1 |
| LAN | 1 | LAN, ABCB6 | 2q36 |

Genotyping for Blood Group Antigens.

In addition to serologic typing, the antigen type of the original RBCs and cRBCs were tested by genotyping which also provided information on chromosomal loss or genetic changes. Genotyping was also required for antigen specificities that were difficult or impossible to characterize by serology alone. DNA was extracted and human erythrocyte antigen (HEA) genotyping for 35 antigens in 12 different systems, as well as RHD genotyping of the original sample and the recombinant cRBCs, was performed. High resolution RH genotyping for altered Rh proteins was performed as described in Jansen et al., Transfusion 53(4): 741-746, 2012. Genotyping was monitored for chromosomal loss in culture across a large number of blood group loci.

FACS and Western Blot Detection of Antigen, Glycosylation, and Protein Membrane Structural Changes.

Flow cytometry and quantitative Western blot was performed to more precisely monitor antigen expression levels of glycophorin A-GPA (MN), glycophorin B-GPB (SsU), Band 3 (Diego), Rh, RhAG, GLUT1, Kell, Duffy, CD59, CD47, CD71, and Colton AQP1 (aquaporin-1). Changes in antigen, glycosylation, and protein expression profiles and epitopes was monitored and mapped. These techniques were used when the standard typing methods provided clues (over or under expression, abnormal reactivity) that new antigens might be present on cRBCs.

Poly-Agglutination.

RBCs were monitored for poly-agglutination associated with alteration of carbohydrate modifications. Normal human sera had naturally occurring antibodies to carbohydrate epitopes associated with the common blood group antigens (anti-A, anti-B) but also had antibodies to other carbohydrate containing structures that occurred in nature (anti-T, anti-Tn). Pools of normal human sera were incubated with the cRBCs and were observed for agglutination by macro- and microscopic methods.

Compatibility Testing.

cRBCs were tested for cross-match compatibility in the same manner as original cells against normal human serum and sera from patients with auto- and allo-antibodies with known specificity.

Screening for Neo Antigens.

A concern with cRBCs, particularly those produced from iPSCs, was that they might express fetal or abnormal proteins or epitopes that might be antigenic. These neo-antigens were unlikely to be detected by testing with blood group antibodies, but might be detected by screening with a large number of human sera from patients and donors who might have encountered these neo-antigens and made natural antibodies.

These important experiments allowed us to determine if cRBCs and erythroid precursors produced by extensive expansion of PB and iPSC-derived CD34$^+$ expressed the same antigen profiles as RBCs produced in vivo.

Minor changes were detected by studying mRNA expression by RNA-sequencing or microarray analysis. Exposure of neo-epitopes on cRBCs also revealed by testing with antibodies to structural components of the underlying RBC cytoskeleton not normally exposed at the cell surface (e.g., spectrin, ankyrin, 4.1, and 4.2).

All of the compositions and/or methods disclosed and claimed herein can be made and executed without undue experimentation in light of the present disclosure. While the compositions and methods of this disclosure have been described in terms of embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

VIII. REFERENCES

The following references, to the extent that they provide exemplary procedural or other details supplementary to those set forth herein, are specifically incorporated herein by reference.

CA2516123
EP 0273085
U.S. Pat. No. 5,811,130
U.S. Pat. No. 9,169,462.
U.S. Pat. No. 9,200,253
U.S. Pat. No. 9,255,248
U.S. Patent Publication 2014/0068797
WO2015032340
WO2015118780
WO2016085934
Baichwal and Sugden, In: *Gene Transfer*, Kucherlapati (Ed), NY, Plenum Press, 117-148, 1986.
Benvenisty and Neshif, *Proc. Natl. Acad. Sci. USA*, 83:9551-9555, 1986.
Bikard et al., *Nucleic Acids Res.* 41(15): 7429-7437, 2013.
Byrne et al., Methods Enzymo; 546:119-38, 2014.
Casas et al., Transfusion, 55, 1388-93, 2015.
Chang et al., PLoS ONE 6, e25761, 2011.
Chen et al., Transfusion 46, 766-772, 2006.
Chen and Okayama, *Mol. Cell Biol.*, 7:2745-2752, 1987.
Cherif-Zahar et al., Proc Natl Acad Sci USA 87, 6243-6247, 1990.
Chou et al., Proc Natl Acad Sci USA 109, 17573-17578, 2012.
Chou and Friedman, Immunohematology 28, 27-30, 2012c.
Chou et al., Blood 122, 1062-1071, 2013.
Chou et al., Br J Haematol 159, 394-404, 2012b.
Chou et al., Blood 132(11):1198-1207, 2018.
Coffin, In: *Virology*, Fields et al. (Eds.), Raven Press, N.Y., 1437-1500, 1990.
Couch et al., *Am. Rev. Resp. Dis.,* 88:394-403, 1963.
Coupar et al., *Gene,* 68:1-10, 1988.
Daniels et al., Transfusion 38, 951-958, 1998.
De Jager et al., *Semin. Nucl. Med.* 23(2), 165-179, 1993.
Denomme, (Bethesda: AABB), pp. 317-336, 2014.
Donnelly et al., *J. Gen. Virol.* 82, 1027-1041, 2001.
Doolittle and Ben-Zeev, *Methods Mol. Biol.,* 109, 215-237, 1999.
Dubensky et al., *Proc. Natl. Acad. Sci. USA,* 81:7529-7533, 1984.
Fechheimer et al., *Proc Natl. Acad. Sci. USA,* 84:8463-8467, 1987.
Flegel et al., Transfusion 46, 1334-1342, 2006.
Ferkol et al., *FASEB J.,* 7:1081-1091, 1993.
Fraley et al., *Proc Natl. Acad. Sci. USA,* 76:3348-3352, 1979
Friedmann, *Science,* 244:1275-1281, 1989.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.,* 6:1733-1739, 1987.
Gomez-Foix et al., *J. Biol. Chem.,* 267:25129-25134, 1992.
Gopal, *Mol. Cell Biol.,* 5:1188-1190, 1985.
Graham and Prevec, In: *Methods in Molecular Biology: Gene Transfer and Expression Protocol*, Murray (Ed.), Humana Press, Clifton, N.J., 7:109-128, 1991.
Graham and van der Eb, *Virology*, 52:456-467, 1973.
Graham et al., *J. Gen. Virol.,* 36:59-72, 1977.
Grunhaus and Horwitz, *Seminar in Virology*, 3:237-252, 1992.
Gubin et al., Blood 96, 2621-2627, 2000.
Gulbis and Galand, *Hum. Pathol.* 24(12), 1271-1285, 1993.
Harland and Weintraub, *J. Cell Biol.,* 101:1094-1099, 1985.
Hermonat and Muzycska, *Proc. Nat'l Acad. Sci. USA,* 81:6466-6470, 1984.
Hersdorffer et al., *DNA Cell Biol.,* 9:713-723, 1990.
Herz and Gerard, *Proc. Nat'l. Acad. Sci. USA* 90:2812-2816, 1993.
Hipsky et al., Vox Sang 102, 167-170, 2012.
Horwich et al., *J. Virol.,* 64:642-650, 1990.
Hsu et al., Cell 157, 1262-1278, 2013.
Jinek et al., Science 337, 816-821, 2012.
Jones and Shenk, Cell, 13:181-188, 1978.
Kaneda et al., *Science,* 243:375-378, 1989.
Karlsson et al., *EMBO J.,* 5:2377-2385, 1986.
Kaneda et al., *Science,* 243:375-378, 1989.
Kato et al., *J Biol Chem.,* 266(6):3361-3364, 1991.
Klein et al., *Nature,* 327:70-73, 1987.
Ko and Prives, Genes & development 10, 1054-1072, 1996.
Koury and Bondurant, Science 248, 378-381, 1990.
Le Gal La Salle et al., *Science,* 259:988-990, 1993.
Levrero et al., *Gene,* 101:195-202, 1991.
Liang et al., PLoS Genet 11, e1005526, 2015.
Lomas-Francis et al., Immunohematology 26, 71-78, 2010.
Mali et al., Science 339, 823-826, 2013a.
Mali et al., *Nat Methods* 10, 957-963, 2013b.
Mali et al., *Nat. Biotechnol.* 31:833-838, 2013c.
Mann et al., *Cell,* 33:153-159, 1983.
Markowitz et al., *J. Virol.,* 62:1120-1124, 1988.
Nakamura et al., In: *Enzyme Immunoassays: Heterogeneous and Homogeneous Systems*, Chapter 27, 1987.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta,* 721:185-190, 1982.
Noizat-Pirenne and Tournamille, Transfus Clin Biol 18, 527-535, 2011.
Paluru et al., Stem cell research 12, 441-451, 2013.
Paskind et al., *Virology,* 67:242-248, 1975.
Perales et al., *Proc. Natl. Acad. Sci. USA,* 91(9):4086-4090, 1994.
Potter et al., *Proc. Natl. Acad. Sci. USA,* 81:7161-7165, 1984.
Racher et al., *Biotech. Techniques,* 9:169-174, 1995.
Ran et al., Nat Protocols, 8:2281-308, 2013.
Renan, *Radiother. Oncol.,* 19:197-218, 1990.
Rich et al., *Hum. Gene Ther.,* 4:461-476, 1993.
Ridgeway, In: *Vectors: A survey of molecular cloning vectors and their uses*, Stoneham: Butterworth, 467-492, 1988.
Rippe et al., *Mol. Cell Biol.,* 10:689-695, 1990.

Rosenfeld et al., *Cell*, 68:143-155, 1992.
Rosenfeld et al., *Science*, 252:431-434, 1991.
Roux et al., *Proc. Natl. Acad. Sci. USA*, 86:9079-9083, 1989.
Stratford-Perricaudet and Perricaudet, In: *Human Gene Transfer*, Cohen-Haguenauer and Boiron (Eds.), John Libbey Eurotext, France, 51-61, 1991.
Stratford-Perricaudet et al., *Hum. Gene. Ther.*, 1:241-256, 1990.
Top et al., *J. Infect. Dis.*, 124:155-160, 1971.
Tur-Kaspa et al., *Mol. Cell Biol.*, 6:716-718, 1986.
Varmus et al., *Cell*, 25:23-36, 1981.
Vege et al., On RhCe Responsible For Expression Of Some E Epitopes Transfusion 52, 34A supplement. Abstract, 2012.
Vichinsky et al., N Engl J Med 322, 1617-1621, 1990.
Vichinsky et al., Transfusion 41, 1086-1092, 2001.
Wagner et al., *Proc. Natl. Acad. Sci. USA*, 87(9):3410-3414, 1990.
Wagner et al., Blood 100, 306-311, 2002.
Wang et al., Comparative analysis of human ex vivo-generated platelets vs. megakaryocyte-generated platelets in mice: A cautionary tale. Blood, 2015.
Welch et al., Blood 104, 3136-3147, 2004.
Westhoff et al., RHCE*ceTI encodes partial c and partial e and is often in cis to RHD*DIVa. Transfusion, 2012.
Westhoff et al., Transfusion 50, 1303-1311, 2010.
Wong et al., *Gene*, 10:87-94, 1980.
Wu and Wu, *Biochemistry*, 27:887-892, 1988.
Wu and Wu, *J. Biol. Chem.*, 262:4429-4432, 1987.
Wu and Wu, *Adv. Drug Delivery Rev.*, 12:159-167, 1993.
Yang et al., *Proc. Natl. Acad. Sci. USA*, 87:9568-9572, 1990.
Yawn et al., *Jama* 312, 1033-1048, 2014.
Zelenin et al., *FEBS Lett.*, 280:94-96, 1991.

What is claimed:

1. A plurality of antigenically distinct engineered red blood cells (RBCs), wherein said plurality of RBCs exhibit distinct blood antigen group profiles, including at least two rare blood antigen groups, wherein:
   (a) said plurality of RBCs are produced from induced pluripotent stem cells using CRISPR to insert, delete or disrupt a coding sequence for one or more blood antigens;
   (b) said plurality of RBCs comprise two or more of the following blood antigen group profiles: Rh null, D –/–, U/S/s antigen negative (glycophorin B null), RHCE negative, positive for low prevalence RhD antigens, Dombrok (Do) null, and Lutheran null; or
   (c) said plurality of RBCs further comprise one or more of Kell positive, Kidd positive, Duffy positive and MNS antigen positive.

2. The plurality of antigenically distinct engineered RBCs of claim 1, wherein said plurality of RBCs exhibit at least three, four, five, six, seven, eight, nine, ten or fifteen distinct blood antigen groups.

3. The plurality of antigenically distinct engineered RBCs of claim 1, wherein said plurality of RBCs are immortalized from naturally-occurring isolated RBCs.

4. The plurality of antigenically distinct engineered RBCs of claim 3, wherein said plurality of RBCs are immortalized by transfecting a naturally-occurring RBC with a construct expressing a transforming oncoprotein.

5. The plurality of antigenically distinct engineered RBCs of claim 1, wherein said plurality of RBCs are produced from induced pluripotent stem cells.

6. The plurality of antigenically distinct engineered RBCs of claim 1, wherein said plurality of RBCs are produced from induced pluripotent stem cells using CRISPR to insert, delete or disrupt a coding sequence for one or more blood antigens.

7. The plurality of antigenically distinct engineered RBCs of claim 1, wherein said plurality of RBCs comprise two or more of the following blood antigen group profiles: Rh null, D –/–, U/S/s antigen negative (glycophorin B null), RHCE negative, positive for low prevalence RhD antigens, Dombrok (Do) null, and Lutheran null.

8. The plurality of antigenically distinct engineered RBCs of claim 6, wherein said plurality of RBCs further comprise one or more of Kell positive, Kidd positive, Duffy positive and MNS antigen positive.

9. The plurality of antigenically distinct engineered RBCs of claim 1, wherein said plurality of RBCs comprise three, four, five or all six blood antigen group profiles.

10. A recombinant red blood cell, wherein the recombinant red blood cell is characterized by the absence of at least one or more cell surface antigens on its surface selected from the group consisting of: a C antigen, an E antigen, a c antigen, an e antigen, a U antigen, an S antigen, an s antigen, an hrB antigen, a Lua antigen, a Lub antigen and a CD47 antigen, and wherein:
   (a) the recombinant red blood cell is characterized by the absence of at least ten of the one or more cell surface antigens; or
   (b) the recombinant red blood cell is characterized by the absence of at least eight of the one or more cell surface antigens; or
   (c) the recombinant red blood cell is characterized by the absence of at least four of the one or more cell surface antigens; or
   (d) the recombinant red blood cell is characterized by the absence of at least two of the one or more cell surface antigens; or
   (e) the recombinant red blood cell is further characterized by the absence of a D antigen on its cell surface; or
   (f) wherein the recombinant red blood cell is further characterized by the presence of a D antigen on its cell surface; or
   (g) the recombinant red blood cell is further characterized by the presence of a Go(a) antigen on its cell surface; or
   (h) the recombinant red blood cell is further characterized by the presence of a DAK antigen on its cell surface; or
   (i) the recombinant red blood cell is characterized by the absence of a Doa antigen and a Dob antigen on its cell surface.

11. The recombinant red blood cell of claim 10, wherein the recombinant red blood cell is characterized by the absence of at least ten of the one or more cell surface antigens.

12. The recombinant red blood cell of claim 10, wherein the recombinant red blood cell is characterized by the absence of at least eight of the one or more cell surface antigens.

13. The recombinant red blood cell of claim 10, wherein the recombinant red blood cell is characterized by the absence of at least four of the one or more cell surface antigens.

14. The recombinant red blood cell of claim 10, wherein the recombinant red blood cell is characterized by the absence of at least two of the one or more cell surface antigens.

15. The recombinant red blood cell of claim 10, wherein the recombinant red blood cell is further characterized by the absence of a D antigen on its cell surface.

16. The recombinant red blood cell of claim 10, wherein the recombinant red blood cell is further characterized by the presence of a D antigen on its cell surface.

17. The recombinant red blood cell of claim 10, wherein the recombinant red blood cell is further characterized by the presence of a Go(a) antigen on its cell surface.

18. The recombinant red blood cell of claim 10, wherein the recombinant red blood cell is further characterized by the presence of a DAK antigen on its cell surface.

19. The recombinant red blood cell of claim 10, wherein the recombinant red blood cell is characterized by the absence of a Doa antigen and a Dob antigen on its cell surface.

20. A kit comprising:
   a solid support;
   a first reagent red blood cell characterized by the presence of one or more cell surface antigens on its surface; and
   a second reagent red blood cell characterized by the absence of at least one of the one or more cell surface antigens on its surface;
   wherein:
   the one or more cell surface antigens are selected from the group consisting of: a C antigen, an E antigen, a c antigen, an e antigen, a U antigen, an S antigen, an s antigen, an hrB antigen, a Lua antigen, a Lub antigen and a CD47 antigen, and wherein:
   (a) the recombinant red blood cell is characterized by the absence of at least ten of the one or more cell surface antigens; or
   (b) the recombinant red blood cell is characterized by the absence of at least eight of the one or more cell surface antigens; or (c) the recombinant red blood cell is characterized by the absence of at least four of the one or more cell surface antigens; or
(d) the recombinant red blood cell is characterized by the absence of at least two of the one or more cell surface antigens; or
(e) the recombinant red blood cell is further characterized by the absence of a D antigen on its cell surface; or
(f) wherein the recombinant red blood cell is further characterized by the presence of a D antigen on its cell surface; or
(g) the recombinant red blood cell is further characterized by the presence of a Go(a) antigen on its cell surface; or
(h) the recombinant red blood cell is further characterized by the presence of a DAK antigen on its cell surface; or
(i) the recombinant red blood cell is characterized by the absence of a Doa antigen and a Dob antigen on its cell surface; and
(j) the first reagent red blood cell and the second reagent red blood cell have the same surface phenotype, except for the at least one cell surface antigen.

* * * * *